United States Patent
Poll et al.

(10) Patent No.: US 9,050,037 B2
(45) Date of Patent: Jun. 9, 2015

(54) VIEW OPTIMIZER AND STABILIZER FOR USE WITH SURGICAL SCOPES

(75) Inventors: Wayne L. Poll, New Albany, OH (US); Matthew J. Huddleston, Galena, OH (US); Caroline M. Crisafulli, Columbus, OH (US); Adam Landis, Reynoldsburg, OH (US); Gregory Drach, Liberty Township, OH (US)

(73) Assignee: Minimally Invasive Devices, Inc., Columbus, OH (US)

(*) Notice: Subject to any disclaimer, the term of this patent is extended or adjusted under 35 U.S.C. 154(b) by 777 days.

(21) Appl. No.: 12/635,632

(22) Filed: Dec. 10, 2009

(65) Prior Publication Data
US 2010/0168520 A1    Jul. 1, 2010

Related U.S. Application Data

(60) Provisional application No. 61/121,514, filed on Dec. 10, 2008, provisional application No. 61/170,864, filed on Apr. 20, 2009.

(51) Int. Cl.
| A61B 1/06 | (2006.01) |
| A61B 1/12 | (2006.01) |
| A61B 1/00 | (2006.01) |
| A61B 1/313 | (2006.01) |

(Continued)

(52) U.S. Cl.
CPC .............. *A61B 1/127* (2013.01); *A61B 1/00091* (2013.01); *A61B 1/00135* (2013.01); *A61B 1/126* (2013.01); *A61B 1/3132* (2013.01); *A61B 17/3474* (2013.01); *A61B 2017/347* (2013.01); *A61M 13/003* (2013.01); *A61M 2202/0225* (2013.01); *A61M 2205/3344* (2013.01)

(58) Field of Classification Search
USPC .................. 600/105, 127, 129, 153–159, 169
See application file for complete search history.

(56) References Cited

U.S. PATENT DOCUMENTS

| 3,373,736 A | 3/1968 | Fiore et al. |
| D230,727 S | 3/1974 | Richman |
| 4,207,874 A | 6/1980 | Choy |

(Continued)

FOREIGN PATENT DOCUMENTS

| EP | 0664101 A1 | 7/1995 |
| EP | 1188415 A2 | 3/2002 |

(Continued)

OTHER PUBLICATIONS

PCT Notification of Transmittal of the International Search Report and the Written Opinion of the International Searching Authority; PCT/US2009/067590, Jul. 22, 2010.

(Continued)

*Primary Examiner* — Matthew J Kasztejna
(74) *Attorney, Agent, or Firm* — Shay Glenn LLP

(57) ABSTRACT

The present application discloses several devices for maintaining visualization with a surgical scope. The embodiments of the device are adapted to shield, defog or clean the lens of the surgical scope while the surgical scope is being used to perform a surgical procedure within a patient's body. In some embodiments, the view optimizer is provided in multiple parts enabling separation of one or more operator control features from engagement with the surgical scope. In some embodiments, the view optimizer features stabilization means for securement and positioning with the surgical scope.

10 Claims, 35 Drawing Sheets

(51) Int. Cl.
*A61B 17/34* (2006.01)
*A61M 13/00* (2006.01)

(56) References Cited

U.S. PATENT DOCUMENTS

| | | | |
|---|---|---|---|
| 4,279,246 A | 7/1981 | Chikama | |
| 4,281,646 A | 8/1981 | Kinoshita | |
| D277,408 S | 1/1985 | Kubokawa et al. | |
| D277,505 S | 2/1985 | Kubokawa et al. | |
| 4,497,550 A | 2/1985 | Ouchi et al. | |
| 4,537,209 A | 8/1985 | Sasa | |
| D280,929 S | 10/1985 | Lystager | |
| 4,548,197 A | 10/1985 | Kinoshita | |
| 4,552,130 A | 11/1985 | Kinoshita | |
| D284,028 S | 5/1986 | Seager | |
| 4,598,698 A * | 7/1986 | Siegmund | 600/131 |
| 4,616,169 A | 10/1986 | Proffitt | |
| 4,617,013 A | 10/1986 | Betz | |
| 4,633,855 A | 1/1987 | Baba | |
| 4,637,814 A | 1/1987 | Leiboff | |
| 4,646,722 A | 3/1987 | Silverstein et al. | |
| 4,735,603 A | 4/1988 | Goodson et al. | |
| 4,741,326 A | 5/1988 | Sidall et al. | |
| 4,748,970 A | 6/1988 | Nakajima | |
| 4,760,838 A | 8/1988 | Fukuda | |
| 4,773,413 A | 9/1988 | Hussein et al. | |
| 4,794,911 A | 1/1989 | Okada | |
| 4,800,869 A | 1/1989 | Nakajima | |
| 4,877,016 A | 10/1989 | Kantor et al. | |
| 4,941,872 A | 7/1990 | Felix et al. | |
| 4,973,321 A | 11/1990 | Michelson | |
| 4,991,565 A | 2/1991 | Takahashi et al. | |
| 4,998,527 A * | 3/1991 | Meyer | 600/104 |
| 5,009,655 A | 4/1991 | Daignault, Jr. et al. | |
| 5,019,054 A | 5/1991 | Clement et al. | |
| 5,027,791 A | 7/1991 | Takahashi | |
| 5,050,585 A | 9/1991 | Takahashi | |
| 5,133,336 A | 7/1992 | Savitt et al. | |
| 5,144,942 A | 9/1992 | Decarie et al. | |
| 5,147,292 A | 9/1992 | Kullas et al. | |
| 5,163,927 A | 11/1992 | Woker et al. | |
| 5,167,220 A | 12/1992 | Brown | |
| 5,201,908 A | 4/1993 | Jones | |
| 5,207,213 A | 5/1993 | Auhll et al. | |
| 5,225,001 A | 7/1993 | Manni et al. | |
| 5,279,549 A | 1/1994 | Ranford | |
| D346,023 S | 4/1994 | Stewart, Sr. | |
| 5,306,272 A * | 4/1994 | Cohen et al. | 606/1 |
| 5,312,400 A | 5/1994 | Bales et al. | |
| 5,313,934 A * | 5/1994 | Wiita et al. | 600/109 |
| 5,320,091 A * | 6/1994 | Grossi et al. | 600/104 |
| 5,328,458 A * | 7/1994 | Sekino et al. | 604/23 |
| 5,336,170 A | 8/1994 | Salerno et al. | |
| 5,339,800 A | 8/1994 | Wiita et al. | |
| 5,359,991 A | 11/1994 | Takahashi et al. | |
| 5,364,407 A | 11/1994 | Poll | |
| 5,386,817 A | 2/1995 | Jones | |
| 5,392,766 A | 2/1995 | Masterson et al. | |
| 5,400,767 A | 3/1995 | Murdoch | |
| 5,448,891 A | 9/1995 | Nakagiri et al. | |
| 5,448,990 A | 9/1995 | De Faria Correa | |
| 5,464,008 A | 11/1995 | Kim | |
| 5,468,240 A * | 11/1995 | Gentelia et al. | 606/42 |
| D369,862 S | 5/1996 | Stewart, Jr. | |
| 5,514,084 A | 5/1996 | Fisher | |
| 5,518,502 A | 5/1996 | Kaplan et al. | |
| 5,562,600 A | 10/1996 | Matsuno | |
| 5,563,737 A | 10/1996 | Kamrat | |
| 5,569,157 A | 10/1996 | Nakazawa et al. | |
| 5,575,753 A | 11/1996 | Yabe et al. | |
| 5,575,756 A * | 11/1996 | Karasawa et al. | 600/157 |
| 5,605,532 A | 2/1997 | Schermerhorn | |
| 5,630,795 A | 5/1997 | Kuramoto et al. | |
| 5,637,075 A | 6/1997 | Kikawada | |
| 5,647,840 A | 7/1997 | D'Amelio et al. | |
| 5,697,888 A * | 12/1997 | Kobayashi et al. | 600/159 |
| 5,746,695 A | 5/1998 | Yasui et al. | |
| 5,788,628 A | 8/1998 | Matsuno et al. | |
| 5,865,730 A | 2/1999 | Fox et al. | |
| 5,868,663 A | 2/1999 | Katsurada et al. | |
| 5,869,107 A | 2/1999 | Shimizu et al. | |
| 5,894,369 A | 4/1999 | Akiba et al. | |
| 5,922,105 A | 7/1999 | Fujii et al. | |
| 5,954,637 A | 9/1999 | Francis | |
| 5,957,888 A | 9/1999 | Hinchliffe | |
| 5,989,183 A | 11/1999 | Reisdorf et al. | |
| 6,017,333 A * | 1/2000 | Bailey | 604/264 |
| 6,040,053 A | 3/2000 | Scholz et al. | |
| 6,071,606 A | 6/2000 | Yamazaki et al. | |
| D428,487 S | 7/2000 | Renner et al. | |
| 6,096,026 A | 8/2000 | Schultz | |
| 6,110,103 A | 8/2000 | Donofrio | |
| 6,110,259 A | 8/2000 | Schultz et al. | |
| 6,126,592 A | 10/2000 | Proch et al. | |
| 6,149,659 A | 11/2000 | Ahmed | |
| 6,156,409 A | 12/2000 | Doushita et al. | |
| 6,176,825 B1 | 1/2001 | Chin et al. | |
| 6,234,635 B1 | 5/2001 | Seitzinger et al. | |
| 6,282,442 B1 | 8/2001 | DeStefano et al. | |
| 6,299,592 B1 | 10/2001 | Zander | |
| 6,306,932 B1 | 10/2001 | Yamamoto et al. | |
| 6,354,992 B1 * | 3/2002 | Kato | 600/157 |
| 6,361,492 B1 | 3/2002 | Santilli | |
| 6,383,134 B1 | 5/2002 | Santilli | |
| 6,409,657 B1 | 6/2002 | Kawano | |
| 6,425,535 B1 | 7/2002 | Akiba | |
| 6,447,446 B1 * | 9/2002 | Smith et al. | 600/157 |
| 6,582,357 B2 | 6/2003 | Ouchi et al. | |
| 6,589,316 B1 | 7/2003 | Schultz et al. | |
| D481,126 S | 10/2003 | Hayamizu | |
| 6,645,197 B2 | 11/2003 | Garrison et al. | |
| D484,594 S | 12/2003 | Hayamizu | |
| D486,910 S | 2/2004 | Hayamizu et al. | |
| 6,695,772 B1 | 2/2004 | Bon et al. | |
| 6,699,185 B2 | 3/2004 | Gminder et al. | |
| 6,712,479 B1 | 3/2004 | Seitzinger et al. | |
| 6,712,757 B2 * | 3/2004 | Becker et al. | 600/121 |
| 6,712,759 B2 * | 3/2004 | Muller | 600/156 |
| 6,752,755 B2 | 6/2004 | Akiba | |
| 6,755,782 B2 | 6/2004 | Ogawa | |
| D493,529 S | 7/2004 | Hayamizu et al. | |
| 6,764,445 B2 | 7/2004 | Ramans et al. | |
| 6,780,516 B2 | 8/2004 | Chen | |
| 6,783,845 B2 | 8/2004 | Zhang et al. | |
| D498,846 S | 11/2004 | Hayamizu et al. | |
| 6,814,697 B2 | 11/2004 | Ouchi | |
| 6,857,436 B2 | 2/2005 | Labib et al. | |
| 6,882,236 B2 | 4/2005 | Dinn et al. | |
| 6,889,400 B2 | 5/2005 | Kawazoe et al. | |
| 6,921,362 B2 | 7/2005 | Ouchi | |
| 6,921,380 B1 | 7/2005 | Epstein et al. | |
| 6,977,053 B2 | 12/2005 | Mukasa et al. | |
| 6,984,204 B2 | 1/2006 | Akiba | |
| 6,989,183 B2 | 1/2006 | McKillip | |
| 7,074,180 B2 | 7/2006 | Bertolero et al. | |
| 7,080,641 B2 | 7/2006 | Gomez | |
| 7,150,713 B2 * | 12/2006 | Shener et al. | 600/156 |
| D534,655 S | 1/2007 | Iranyi et al. | |
| D535,743 S | 1/2007 | Williams | |
| 7,169,167 B2 * | 1/2007 | Chu | 606/205 |
| 7,198,599 B2 * | 4/2007 | Goto et al. | 600/154 |
| 7,223,231 B2 | 5/2007 | Akiba | |
| 7,250,028 B2 | 7/2007 | Julian et al. | |
| 7,270,670 B1 | 9/2007 | Yencho | |
| 7,335,159 B2 * | 2/2008 | Banik et al. | 600/156 |
| 7,341,556 B2 | 3/2008 | Shalman | |
| D573,711 S | 7/2008 | Johnson et al. | |
| 7,413,543 B2 * | 8/2008 | Banik et al. | 600/129 |
| D600,807 S | 9/2009 | Dienst et al. | |
| D613,403 S | 4/2010 | Poll et al. | |
| 7,803,109 B2 | 9/2010 | Gomez | |
| 7,927,271 B2 * | 4/2011 | Dimitriou et al. | 600/106 |
| 8,047,215 B1 * | 11/2011 | Sasaki | 134/95.2 |
| 8,062,214 B2 * | 11/2011 | Shener et al. | 600/159 |

(56) References Cited

U.S. PATENT DOCUMENTS

| | | | |
|---|---|---|---|
| 8,075,481 B2 | 12/2011 | Park et al. | |
| 8,096,944 B2 | 1/2012 | Harrel | |
| 8,167,790 B2 * | 5/2012 | Kucklick et al. | 600/114 |
| 8,226,549 B2 * | 7/2012 | Kumar et al. | 600/156 |
| 8,419,624 B2 | 4/2013 | James et al. | |
| 8,545,395 B2 * | 10/2013 | Akahoshi et al. | 600/104 |
| 2001/0011162 A1 | 8/2001 | Epstein | |
| 2002/0022762 A1 | 2/2002 | Beane et al. | |
| 2002/0058858 A1 | 5/2002 | Ogura et al. | |
| 2002/0072652 A1 | 6/2002 | Berci et al. | |
| 2002/0091304 A1 | 7/2002 | Ogura et al. | |
| 2002/0193806 A1 | 12/2002 | Moenning et al. | |
| 2003/0200738 A1 | 10/2003 | Booth | |
| 2004/0034339 A1 | 2/2004 | Stoller et al. | |
| 2004/0059363 A1 | 3/2004 | Alvarez et al. | |
| 2004/0082915 A1 | 4/2004 | Kadan | |
| 2004/0204671 A1 | 10/2004 | Stubbs et al. | |
| 2005/0043683 A1 | 2/2005 | Ravo | |
| 2005/0059981 A1 | 3/2005 | Poll | |
| 2005/0065405 A1 | 3/2005 | Hasegawa | |
| 2005/0075538 A1 * | 4/2005 | Banik et al. | 600/141 |
| 2005/0113797 A1 | 5/2005 | Ott et al. | |
| 2005/0119528 A1 | 6/2005 | Weinberg | |
| 2005/0137529 A1 | 6/2005 | Mantell | |
| 2005/0154355 A1 | 7/2005 | Gross et al. | |
| 2005/0159765 A1 | 7/2005 | Moutafis et al. | |
| 2005/0171467 A1 | 8/2005 | Landman | |
| 2005/0171528 A1 | 8/2005 | Sartor et al. | |
| 2005/0203342 A1 | 9/2005 | Kucklick et al. | |
| 2005/0234301 A1 | 10/2005 | Gomez | |
| 2005/0261553 A1 | 11/2005 | Swain et al. | |
| 2006/0020165 A1 * | 1/2006 | Adams | 600/121 |
| 2006/0041186 A1 | 2/2006 | Vancaillie | |
| 2006/0047184 A1 * | 3/2006 | Banik et al. | 600/156 |
| 2006/0052661 A1 | 3/2006 | Gannot et al. | |
| 2006/0069306 A1 | 3/2006 | Banik et al. | |
| 2006/0252993 A1 | 11/2006 | Freed et al. | |
| 2006/0270910 A1 | 11/2006 | Davis | |
| 2007/0203474 A1 | 8/2007 | Ryan et al. | |
| 2007/0282253 A1 | 12/2007 | Sasaki | |
| 2007/0289449 A1 | 12/2007 | Roberts et al. | |
| 2007/0299310 A1 | 12/2007 | Phillips | |
| 2008/0021277 A1 | 1/2008 | Stefanchik et al. | |
| 2008/0051631 A1 | 2/2008 | Dejima et al. | |
| 2008/0081948 A1 | 4/2008 | Weisenburgh et al. | |
| 2008/0086704 A1 | 4/2008 | Aravamudan | |
| 2008/0108871 A1 | 5/2008 | Mohr | |
| 2008/0161646 A1 | 7/2008 | Gomez | |
| 2008/0188715 A1 | 8/2008 | Fujimoto | |
| 2008/0200765 A1 | 8/2008 | Mondschein | |
| 2008/0208128 A1 | 8/2008 | Guo et al. | |
| 2008/0249362 A1 | 10/2008 | Jiang et al. | |
| 2008/0319266 A1 | 12/2008 | Poll et al. | |
| 2009/0018602 A1 | 1/2009 | Mitelberg et al. | |
| 2009/0113644 A1 | 5/2009 | Heck | |
| 2009/0215018 A1 | 8/2009 | Edmondson et al. | |
| 2009/0253962 A1 | 10/2009 | Fernandez et al. | |
| 2009/0253965 A1 | 10/2009 | Miyamoto | |
| 2010/0198014 A1 | 8/2010 | Poll et al. | |
| 2012/0022331 A1 | 1/2012 | Poll et al. | |
| 2012/0165610 A1 | 6/2012 | Poll et al. | |
| 2012/0184897 A1 | 7/2012 | Poll | |
| 2012/0197084 A1 | 8/2012 | Drach et al. | |
| 2012/0310147 A1 | 12/2012 | Poll et al. | |

FOREIGN PATENT DOCUMENTS

| | | |
|---|---|---|
| JP | 59-203534 | 11/1984 |
| JP | 61-168328 | 7/1986 |
| JP | 05-199979 | 8/1993 |
| JP | 09-135804 | 5/1997 |
| JP | 2000-225093 | 8/2000 |
| JP | 2005-110978 | 4/2005 |
| WO | WO92/10969 A1 | 7/1992 |
| WO | WO92/22238 A1 | 12/1992 |
| WO | WO2005/009227 A1 | 2/2005 |
| WO | WO2006/014814 A1 | 2/2006 |
| WO | WO2008/030256 A1 | 3/2008 |
| WO | WO2008/077080 A2 | 6/2008 |
| WO | WO2008/128142 A2 | 10/2008 |
| WO | WO2008/130582 A2 | 10/2008 |
| WO | WO2009/073577 A2 | 6/2009 |
| WO | WO2010/042913 A2 | 4/2010 |
| WO | WO2010/042915 A2 | 4/2010 |
| WO | WO2011/041387 A1 | 4/2011 |
| WO | WO2011/044448 A2 | 4/2011 |

OTHER PUBLICATIONS

International Preliminary Report on Patentability for International Application No. PCT/US09/67590 dated Apr. 7, 2011.

Ott, Douglas E.; Chapter 1. Pneumoperitoneum: Production, management, effects and consequences; in Prevention & Management of Laparoendoscopic Surgical Complications, 1st Ed.; 6 pgs.; Jan. 1999 (retrieved from: http://laparoscopy.blogs.com/prevention_management/2006/02/chapter_1_pneum.html on Oct. 7, 2013).

Poll et al.; Design U.S. Appl. 29/329,224 entitled "Manifold Coupling," filed Dec. 10, 2008 (now abandoned).

Poll et al.; Design U.S. Appl. No. 29/329,225 entitled "Sheath Manifold For Maintaining Surgical Scope Visualization," filed Dec. 10, 2008 (now abandoned).

Poll et al.; Design U.S. Appl. No. 29/329,221 entitled "Handle For Maintaining Surgical Scope Visualization," filed Dec. 10, 2008 (now abandoned).

Poll et al.; Design U.S. Appl. No. 29/335,699 entitled "Surgical Scope Stabilizer," filed Apr. 20, 2009 (now abandoned).

Farley et al.; Double-blind, prospective, randomized study of warmed, humidified carbon dioxide insufflation vs standard carbon dioxide for patients undergoing lararoscopic cholecystectomy; Arch Surg; 139; pp. 739-744; Jul. 2004.

Hashimoto et al.; Development of a fogless scope and its analysis using infrared radiation pyrometer; Surg Endosc; 11(8); pp. 805-808; Aug. 1997.

Ohdaira et al.; Antifogging effects of a socket-type device with the superhydrophilic, titanium dioxide coated glass for laparoscope; Surg endosc; 21(2); pp. 333-338; Dec. 2007.

Poll et al.; U.S. Appl. No. 14/308,644 entitled "Sheath for hand-held and robotic laparoscopes," filed Jun. 18, 2014.

Poll et al.; U.S. Appl. No. 14/490,501 entitled "Systems and methods for optimizing and maintaining visualization of a surgical field during the use of surgical scopes," filed Sep. 18, 2014.

* cited by examiner

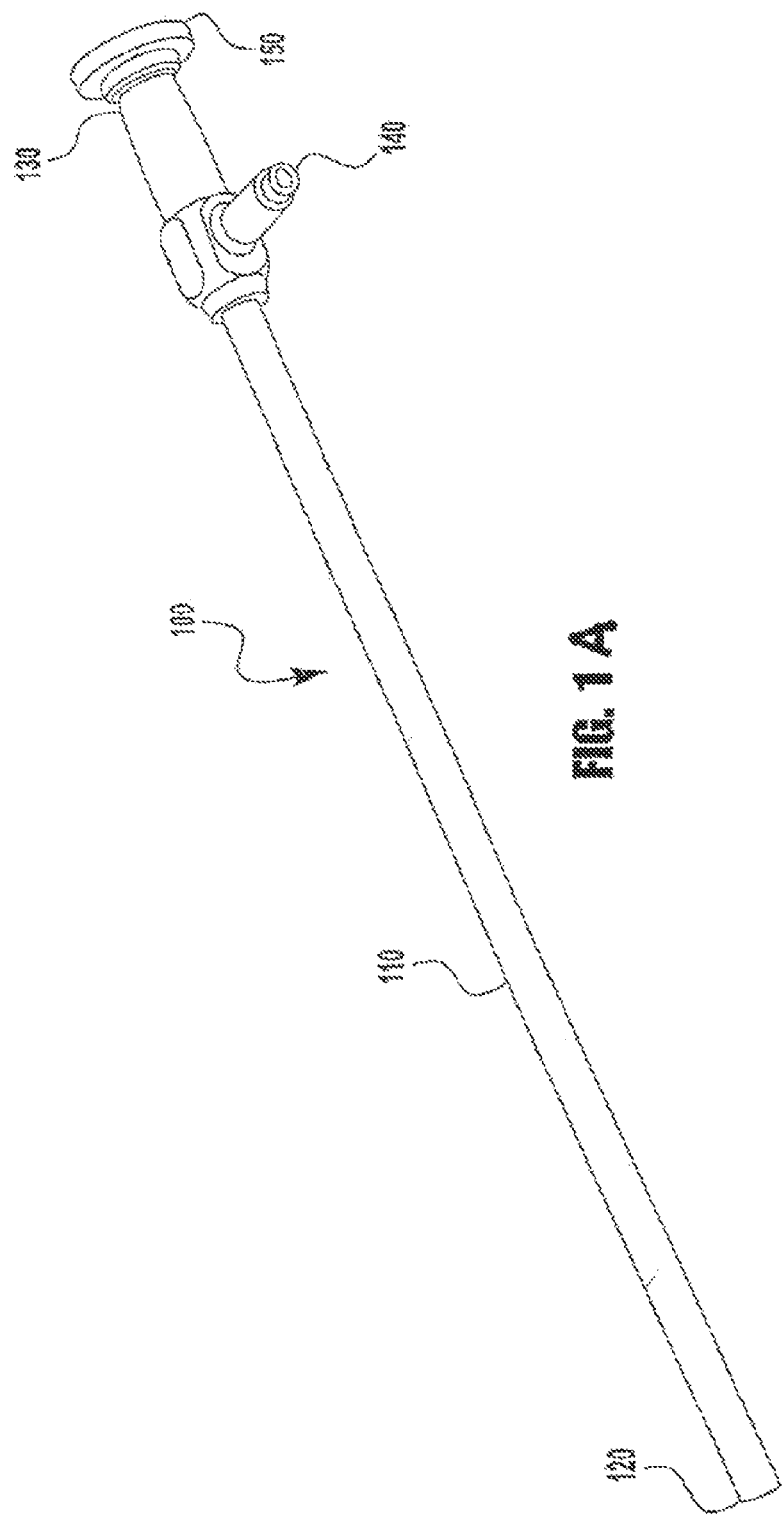

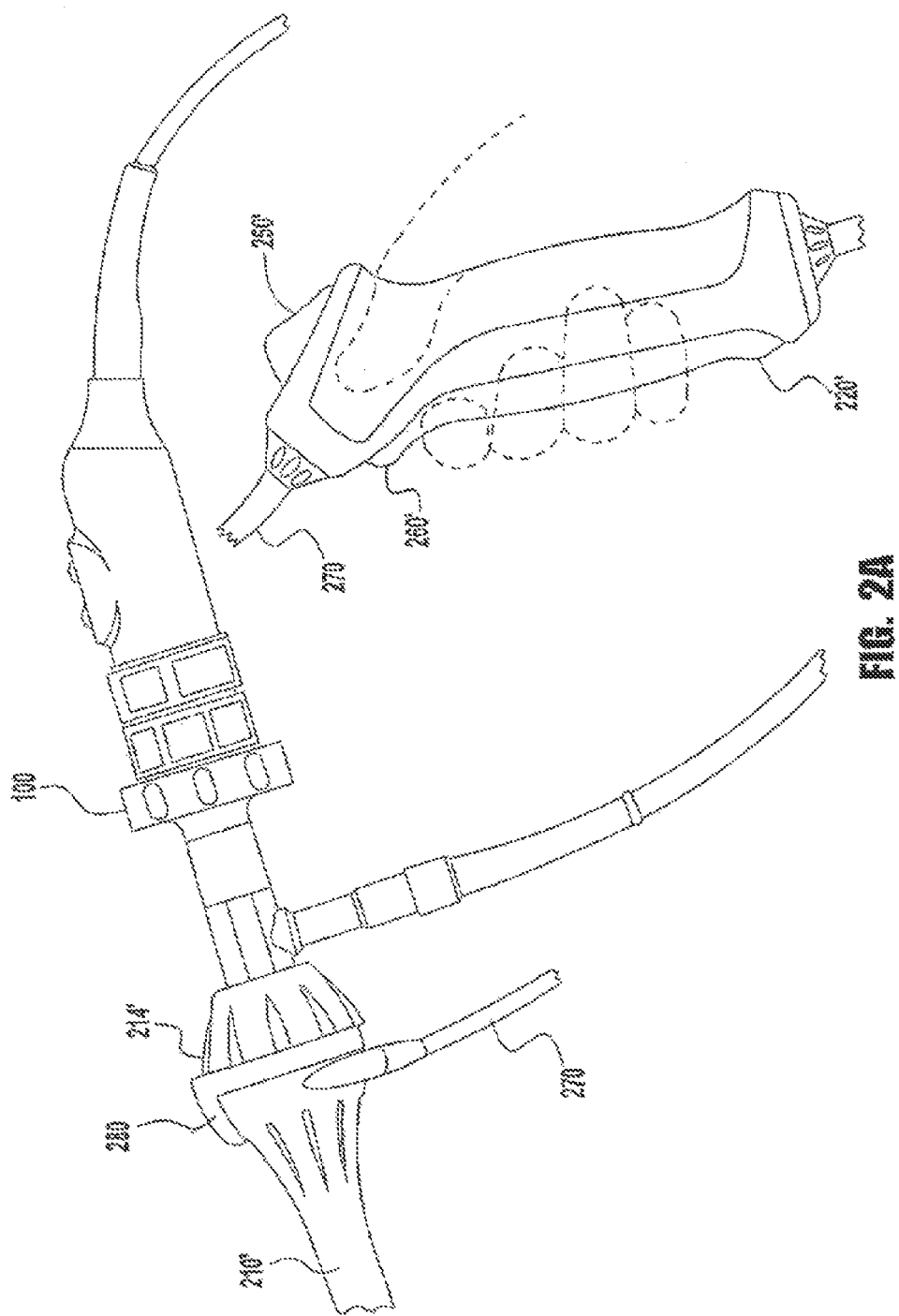

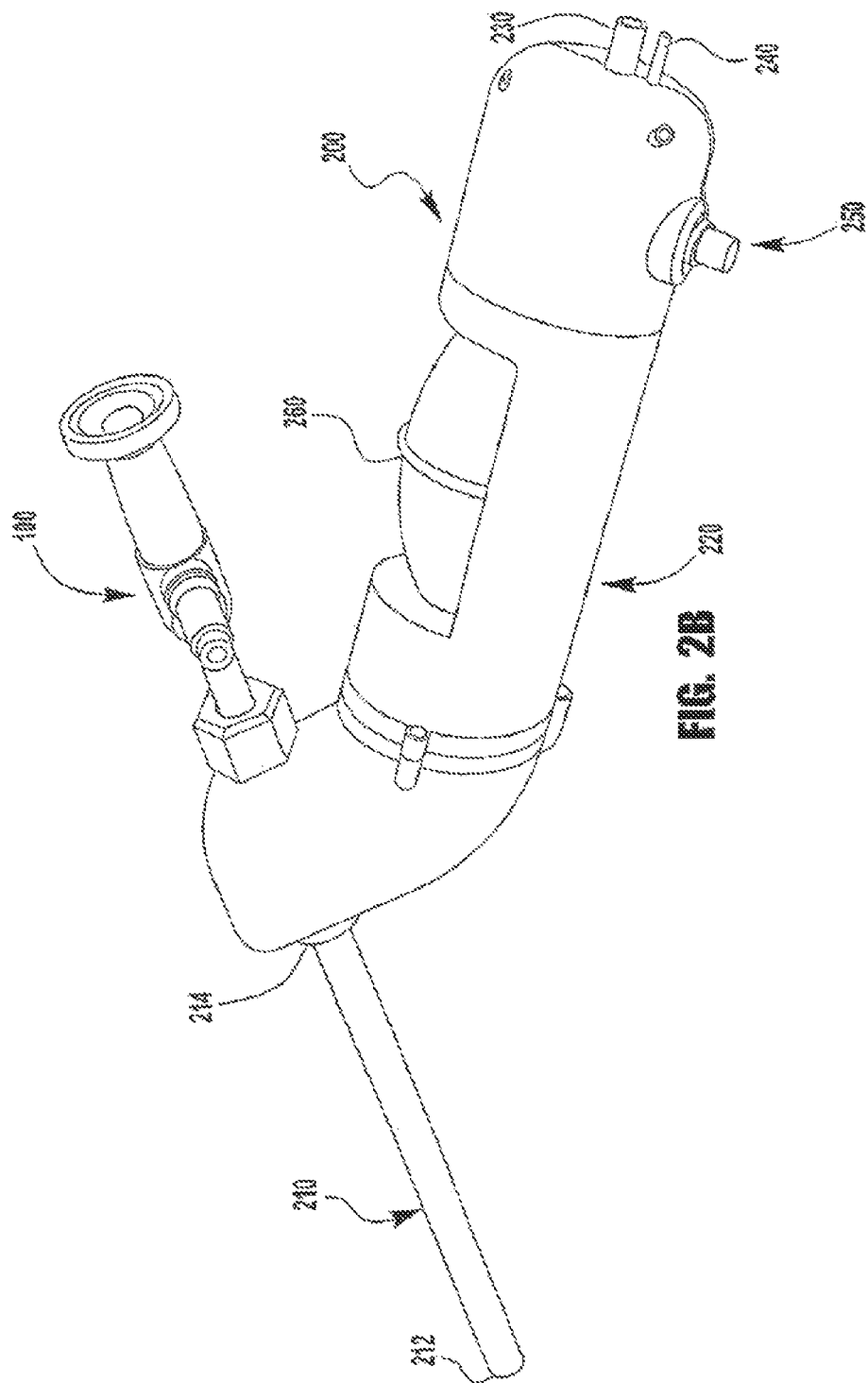

220

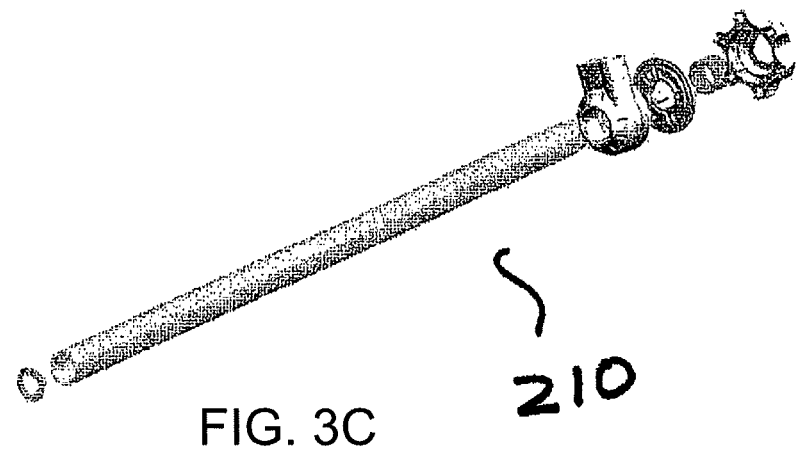
FIG. 3C     210
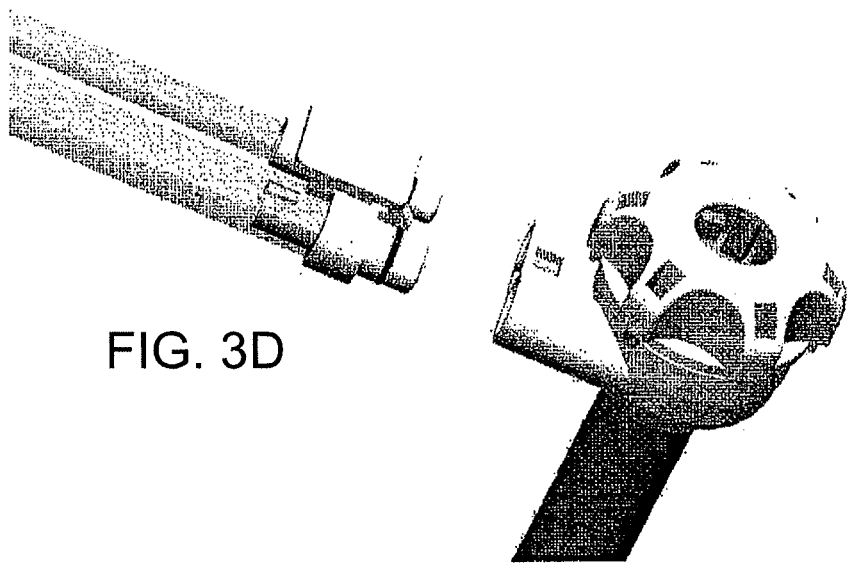
FIG. 3D

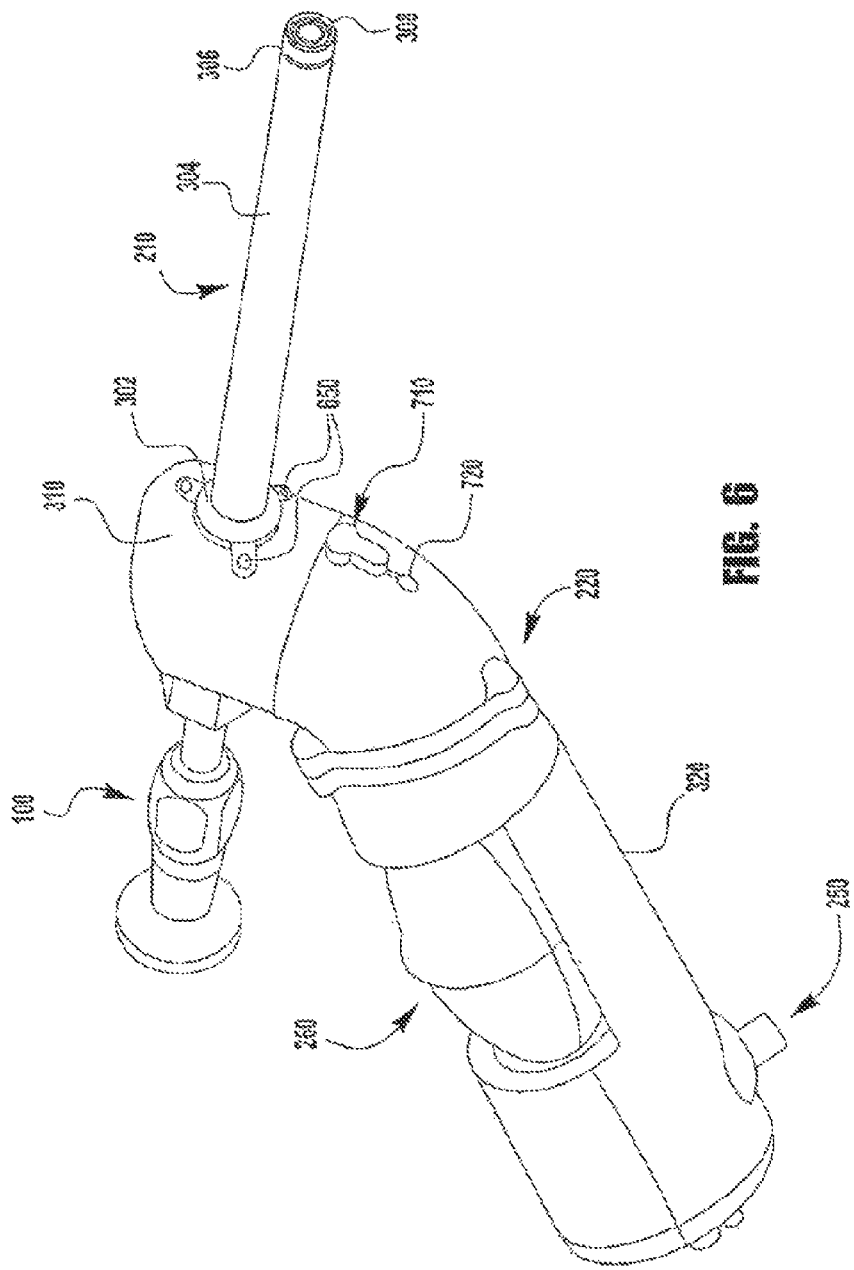

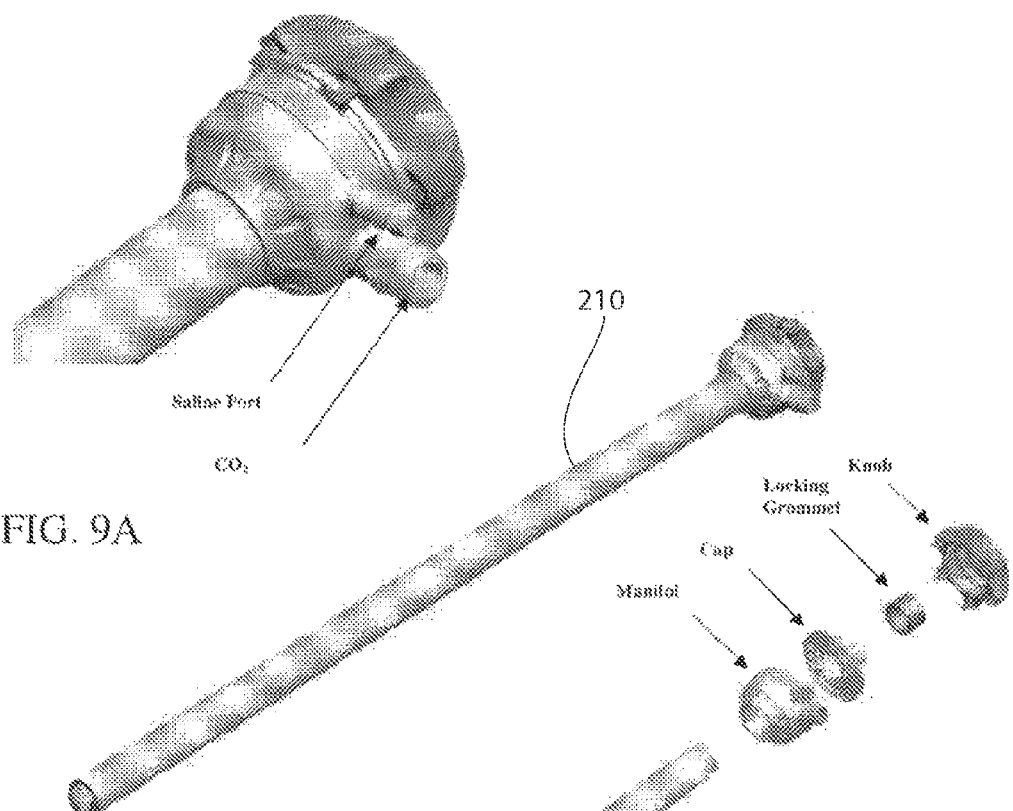
FIG. 9A
FIG. 9B
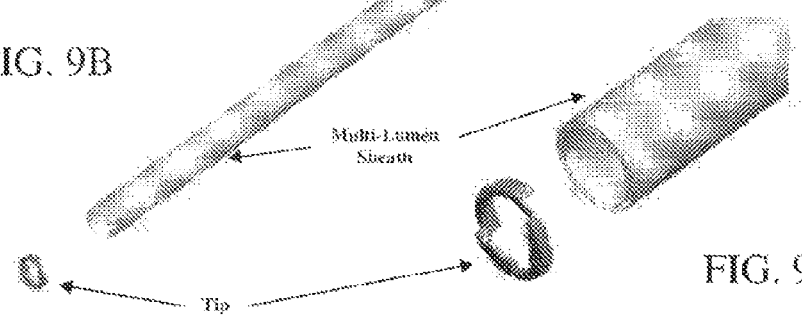
FIG. 9C

VIEW OPTIMIZER AND STABILIZER FOR USE WITH SURGICAL SCOPES

CROSS REFERENCE TO RELATED APPLICATIONS

This application is related to U.S. Utility Application Ser. No. 11/765,340, filed Jun. 19, 2007 and to PCT Application Ser. No. PCT/US2008/067426, filed Jun. 9, 2008, the entirety of which applications are incorporated by reference herein.

PRIORITY CLAIM

This application claims priority to U.S. Provisional Application Ser. Nos. 61/121,514 filed on Dec. 10, 2008 and 61/170,864 filed on Apr. 20, 2009, the entirety of which applications are incorporated by reference herein.

TECHNICAL FIELD

The present application relates generally to various embodiments of a device for maintaining visualization with surgical scopes. More particularly, this application relates to various embodiments of a view optimizer adapted to shield, clean and defog or clean the lens of a surgical scope, such as a laparoscope, while the surgical scope is being used to perform a surgical procedure within a cavity of a patient's body.

BACKGROUND OF THE INVENTION

Minimally invasive surgical procedures utilizing surgical scopes are desirable because they often provide one or more of the following advantages: reduced blood loss; reduced post-operative patient discomfort; shortened recovery and hospitalization time; smaller incisions; and reduced exposure of internal organs to possible contaminants.

Generally, minimally invasive surgeries utilize scopes, such as laparoscopes, that permit remote visualization of a surgical site within a patient's body while the surgical procedure is being performed. During a laparoscopic procedure, the patient's abdominal or pelvic cavity is accessed through two or more relatively small incisions rather than through a single large incision that is typical in a conventional surgery. Surgical scopes, such as laparoscopes, usually consist in part of a rigid or relatively rigid rod or shaft having an objective lens at one end and an eyepiece and/or integrated visual display at the other. The scope may also be connected to a remote visual display device or a video camera to record surgical procedures.

In laparoscopic surgeries, the abdomen is typically inflated with a gas through the use of an insufflator, to distend the abdominal space by elevating the abdominal wall above the internal organs and thereby create a sufficient working and viewing space for the surgeon. Carbon dioxide is usually used for insufflation, though other suitable gases may also be used. Conventional insufflators are adapted to cycle on and off to maintain a preset and suitable pressure within the patient's body cavity.

The local environment within a patient's abdominal space is generally rather warm and humid, and the use of devices such as harmonic scalpels and other cutting and coagulating devices generate mist, smoke, and other debris that is released into the surgical field and often becomes suspended throughout the expanded abdominal space. Additionally, blood, bodily fluids, pieces of tissue, fat or other bodily material may come in contact with or even attach to the lens. As a result of these conditions, visualization through the scope can be significantly diminished. Typically, the only solution to fogging and debris collection on the lens is removal of the scope from the body cavity and defogging or cleaning the lens by wiping it with a cloth, warming the scope tip, or utilizing another defogging method. The need to remove the scope to defog and remove debris from the lens is inconvenient for the scope operator and the surgeon and can interrupt and undesirably prolong surgical procedures.

SUMMARY

Embodiments of a device for maintaining visualization with a surgical scope are provided. The embodiments of the device are adapted to shield, defog or clean the lens of the surgical scope while the surgical scope is being used to perform a surgical procedure within a patient's body. Some embodiments include features for stabilizing the scope and its position relative to the view optimizer and for locking the view optimizer to a surgical scope.

Additional features and advantages of the invention will be set forth in part in the description which follows, and in part will be obvious from the description, or may be learned by practice of the invention. The features and advantages of the invention will be realized and attained by means of the elements and combinations particularly pointed out herein.

It is to be understood that both the foregoing general description and the following detailed description are exemplary and explanatory only and are not restrictive of the invention.

The accompanying drawings, which are incorporated in and constitute a part of this specification, illustrate several embodiments of the invention, and together with the description, serve to explain the principles of the invention.

BRIEF DESCRIPTION OF THE DRAWINGS

The present invention may be more readily understood by reference to the following drawings wherein:

FIG. 1A is a perspective view of a laparoscope;

FIG. 2A is a perspective view of an exemplary embodiment of the view optimizer showing the lens guard and flow controller as separate parts interconnected with tubing;

FIG. 2B shows a perspective view of another exemplary embodiment of the view optimizer showing the lens guard and the flow controller with integrated construction;

FIGS. 3A, 3B, 3C and 3D show in four panels exploded perspective views of the flow controller and the lens guard of the view optimizer of FIG. 2C;

FIG. 6 shows an alternate perspective view of the view optimizer of FIG. 2B;

FIG. 9A shows an perspective view of the lens guard of the view optimizer of FIG. 2C and FIGS. 3A-3D;

FIG. 9C shows a magnified perspective view of the tip and exhaust ring of the guard tube of the lens guard of the view optimizer of FIG. 2C and FIGS. 3A-3D;

DETAILED DESCRIPTION OF THE INVENTION

Figure 1B:
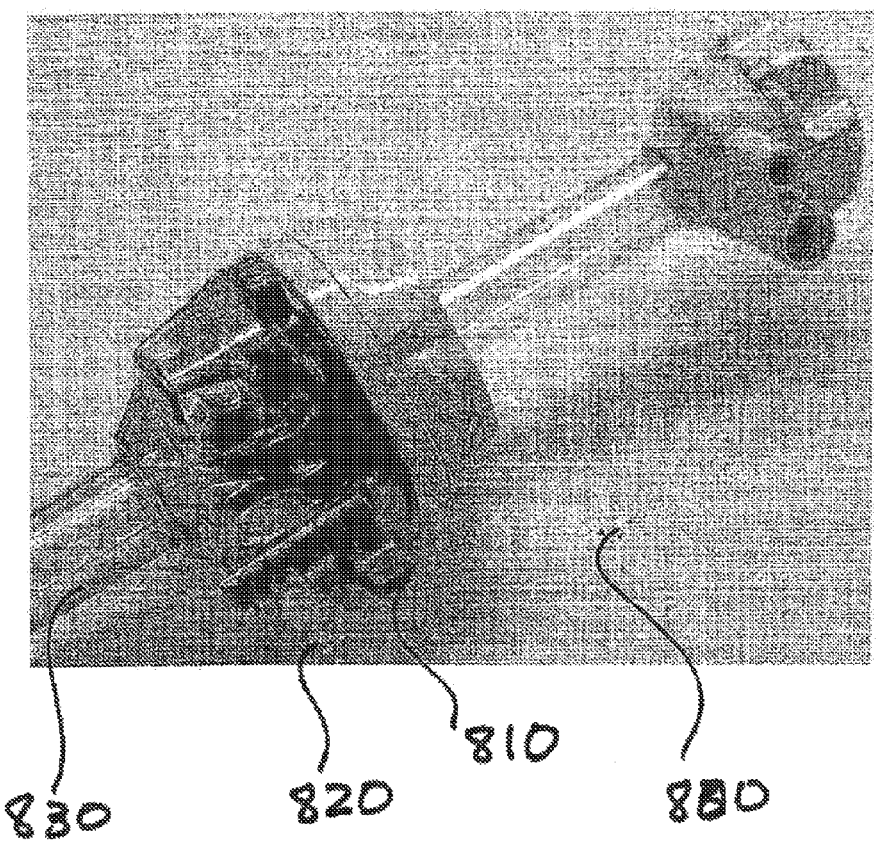
FIG. 1B is a perspective view of a trocar.

The present invention will now be described with occasional reference to specific embodiments of the invention. This invention may, however, be embodied in different forms and should not be construed as limited to the embodiments set forth herein. Rather, these embodiments are provided so that this disclosure will fully convey the scope of the invention to those skilled in the art.

Except as otherwise specifically defined herein, all terms used herein have the same meaning as commonly understood by one of ordinary skill in the art to which this invention belongs. The terminology used in the description of the invention herein is for describing particular embodiments only, and is not intended to be limiting of the invention. As used in the description of the invention and the appended claims, the singular forms "a," "an," and "the" are intended to include the plural forms as well, unless the context clearly indicates otherwise.

Unless otherwise indicated, all numbers expressing quantities, properties, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values to the extent that such are set forth in the specific examples are reported as precisely as possible. Any numerical values, however, inherently contain certain errors necessarily resulting from error found in their respective measurements.

Described herein are various embodiments of a device for use with surgical scopes. In some embodiments, this application relates to various embodiments of view optimizer devices of varying constructions for use with laparoscopes, the view optimizer device being adapted to shield, defog or clean the lens of the laparoscope while the laparoscope is being used to perform a surgical procedure within a patient's body, thereby enhancing patient safety by maintaining clear and stable visualization of the surgical field. In certain embodiments disclosed herein the devices are adapted to connect with the insufflation circuit and irrigation systems resident in the standard surgical suite, diverting only a small fraction of the flow from these systems to provide device functionality and requiring no power source. The devices function to prevent fogging and deflect and remove from the lens of the surgical scope solid and aerosolized surgical debris, including blood, smoke, saline, tissue and other materials and debris in the surgical field. These functions are achieved through means that include intermittent or continuous flow of gas, typically $CO_2$, across the distal end, delivery by manual or automated means of a saline flush or a $CO_2$ burst over the lens, and venting through either a conventional trocar or other means incorporated in the inventive devices. The device functions are achieved without the need for withdrawal of the surgical scope from the surgical trocar so as to enable maintenance if the surgical image. Though the various device embodiments are referred to herein as a view optimizer, and though the various device component parts and functions have likewise been given descriptors herein, it will be appreciated that such descriptor designations are not intended to and do not limit in any way the device's and component's use and operation for a variety of purposes as further described herein in addition to controlling, improving and maintaining and improving desirable visualization of a laparoscopic surgical field.

Conventional Devices

Referring to FIG. 1A, a perspective view of an exemplary, conventional laparoscope 100 is shown. The laparoscope 100 has an elongated cylindrical main body 110 having a distal end 120 and an imaging end 130. The main body 110 of the laparoscope may be either rigid or flexible, depending on the procedure the laparoscope is being used to perform, as well as the type of laparoscope being utilized. An objective lens (not shown in FIG. 1A) is disposed within the distal end 120 of the main body 110, the objective lens being generally transverse to the longitudinal axis of the main body 100. Generally, laparoscope 100 includes an illumination system, which can be any type of suitable illumination system, such as a network of fiber optic cables, housed within the main body 110 of laparoscope 100 for illuminating the surgical site being imaged by the operative lens of the laparoscope. Laparoscope 100 includes an illuminator connector 140 for the connection of an external light source, which supplies the illumination system with illuminating light.

The imaging end 130 of the main body 110 of the laparoscope 100 includes an eyepiece 150. Conventional laparoscopes include an image transmission system (not shown in FIG. 1A), which can be selected from any type of suitable image transmission systems, such as a system of lens, lens rods or other optical components, housed within the main body 110 of the laparoscope for transmitting the image viewed by the objective lens to the eyepiece 150, thus allowing the scope operator to view within the patient's abdominal cavity. It is well known in the art that a video camera or other visual display device can be operatively connected to the eyepiece 150 or other portion of the laparoscope 100 to convert the optical signal into a video signal, which is ultimately processed by a video processing means to produce a video image on a monitor or for storage on magnetic tape or other storage media.

Referring now to FIG. 1B, a perspective view of an exemplary, conventional trocar 800 is shown. Trocar systems are surgical devices used to obtain access to a body cavity to perform various surgical procedures, such as, for example, laparoscopic surgery or arthroscopic surgery.

It should be understood that the laparoscope device is typically used in conjunction with a trocar which directs access of the scope to the laparoscopic surgical field. It should be further understood that conventional trocars are, by design, adapted with cannulas that have a diameter suitable to receive conventional scopes, and that any attachments to a conventional surgical scope, such as the view optimizer device and embodiments described herein, will be sized to fit over a portion of a conventional scope and capable of being inserted into the cannula of a conventional trocar. And it will be appreciated that in its various embodiments, the view optimizer of the present application can be used in connection with a variety of trocars and with a variety of laparoscopes and other surgical scopes of varying construction wherein the trocar is adapted to receive a scope within a cannula or like tube.

It is well known in the art that trocar systems typically include, among various optional features, a pointed rod-like device or obdurator fitted into a tube-like device or cannula and a port and a stopcock for permitting the introduction and venting of a pressurized fluid through the cannula for insufflating a body cavity when providing a pneumoperitoneum. In use, a pointed end of the obdurator projects out an end of a cannula and is used to penetrate the outer tissue of the body cavity. After the tissue is penetrated and the body cavity is accessed by the trocar system, the obdurator is then withdrawn while the cannula is retained in the cavity. The body cavity can then be accessed by surgical instruments via the cannula to perform various surgical procedures, or the cannula can simply be used as a drainage outlet. The trocar illustrated in FIG. 1B has a stopcock valve 810 for opening and closing a port 820. The valve may be operated by hand, for example, by a surgeon or a surgical assistant, and moved between two or more positions to control the flow of fluid, such as gas, through the cannula 830 and thus between the surgical suite and the surgical field within the patient's body cavity.

It should be understood that the laparoscope and trocar devices discussed above are representative of conventional scopes such as laparoscopes and trocars. It should be further understood that conventional trocars are, by design, adapted with cannulas that have a diameter suitable to receive conventional scopes, and that any attachments to a conventional surgical scope, such as the view optimizer device and embodiments described herein, will be sized to fit over a portion of a conventional scope and capable of being inserted into the cannula of a conventional trocar. And it will be appreciated that in its various embodiments, the view optimizer device of the present application can be used in connection with a variety of trocars and with a variety of laparoscopes or other surgical scopes of varying constructions wherein the trocar is adapted to receive a scope within a cannula or like tube.

View Optimizing Devices—General Construction

Figure 2C:
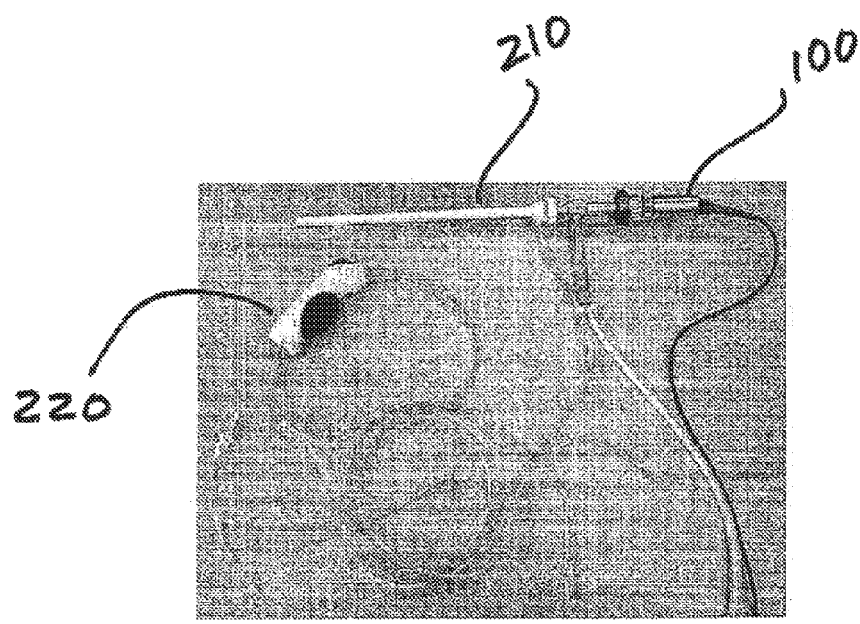
FIG. 2C is a photograph of yet another exemplary embodiment of the view optimizer showing the lens guard and flow controller as separate parts which are interconnected with tubing, where with the lens guard is engaged with a conventional laparoscope and is connected via tubing with the flow controller and the flow controller is connected to additional tubing for interconnection with sources of saline and $CO_2$ and a conventional insufflator trocar.

Referring now to FIG. 2A and FIG. 2C show exemplary embodiments of the view optimizer 200 of the present application having multi part construction, and FIG. 2B shows an exemplary embodiment having unitary construction. As shown in FIGS. 2A and 2B and 2C, the view optimizer 200 generally includes a lens guard 210 and a flow controller 220 (shown, respectively without and with prime ("'") designation). The lens guard 210 of the illustrated embodiment is adapted to receive a portion of the laparoscope 100, most particularly the distal end 120 thereof, and a portion of the main body 110 of the laparoscope. The lens guard 210 of the illustrated embodiment is in the form of a substantially continuous cylindrical sheath or tube that encloses a significant portion of the body of the laparoscope 100. It will be appreciated that in alternate embodiments, the lens guard 210 may be discontinuous, such that it may be formed of an open lattice or matrix that does not fully enclose the body of the laparoscope. As will be described further herein, the common structural features of the various embodiments of the lens guard 210 will be adapted to allow communication between the lens guard 210 of the view optimizer 200 at the distal end 120 of the laparoscope, on the one hand, and the flow controller 220 of the view optimizer 200 on the body 110 of the laparoscope near its imaging end 130, on the other hand, so as to provide for the functions of the view optimizer. Referring generally to the depicted devices, the view optimizer 200 is adapted to deliver to the objective lens of the laparoscope at least one fluid selected from, for example, a liquid, such as water or saline or a surfactant or other liquid, and a gas, such as $CO_2$ or air, to prevent the contact of material with the objective lens of the laparoscope or to defog or clean the objective lens of the laparoscope without the need to remove the laparoscope from the surgical field.

In accordance with some embodiments, the fluid delivered to the objective lens is a gas, in some embodiments, the gas is medical grade $CO_2$. The gas that is delivered to the objective lens of the laparoscope 100 by the view optimizer 200 is supplied by a conventional insufflator. Of course, it should be understood that the view optimizer 200 of this application could be supplied with gas via another external source other than an insufflator, or could include a gas supply device incorporated within or provided with the view optimizer 200, or by combinations of gas sources. Conventional insufflators are designed to insufflate a patient's abdominal cavity until a pre-determined suitable pressure for the operative procedure is reached. Once this pre-determined pressure is reached, conventional insufflators are designed to cease insufflating the cavity. Typical insufflators are designed to resume insufflation once the pressure in the cavity drops below the pre-determined pressure due to the leakage of gas through the trocars being used, through incisions in the patient's body cavity, or by some other means. In this manner, conventional insufflators typically continuously cycle between an insufflation state and a static state while being utilized during an operative procedure to maintain a pre-determined pressure within the patient's abdominal cavity.

Referring now to FIG. 2A, the lens guard 210' of the illustrated embodiment of the view optimizer 200 is an elongated, hollow cylindrical tube. The lens guard 210' has a distal end 212' and a proximal end 214'. The distal end 212' of the lens guard 210' is adapted to surround the distal end 120 of the laparoscope 100. According to the illustrated embodiment, the distal end 212' of the lens guard 210' does not cover or fully enclose the distal end 120 of the laparoscope. It will be appreciated that in some alternate embodiments, a lens guard 210' may include structure that fully encloses the distal end 120 of the laparoscope, and as such is formed of a material that permits visualization. The proximal end 214' of the lens guard 210' is joined to the flow controller 220' of the view optimizer 200. The flow controller 220' of the view optimizer 200 of the illustrated embodiment is adapted to support and enclose components of the view optimizer 200. The flow controller 220' of the of the view optimizer 200 supplies the lens guard 210' with gas and/or liquid via one or more of conduits that connect to lens guard 210'. The flow controller 220' receives gas and/or liquid from one or more exterior sources via air inlet 230 and liquid inlet 240 and delivers the gas and/or liquid to the lens guard 210'. The flow controller 220' of the illustrated embodiment includes a gas/liquid flow actuator/regulator 250' for the actuation and/or regulation of the flow of gas and/or liquid to the lens guard 210'. The flow controller 220' of the illustrated embodiment includes a burst flow actuator/regulator 260' for the actuation and/or regulation of the delivery of a burst or bolus of gas and/or liquid to the lens guard 210', as described herein.

FIG. 2B shows the lens guard 210 and the flow controller 220 of the view optimizer 200 joined together as a unitary construction. It should be understood that the lens guard 210 and the flow controller 220 could be provided as two or more separate pieces that are used remotely from one another and not joined together as a unitary construction. FIG. 2A shows a side view of another exemplary embodiment of the view optimizer 200 of the present application. In this embodiment, the view optimizer 200 is in two separate pieces (as previously noted, the prime designation, e.g. 210', is used to reference features that are common between the embodiments depicted in FIG. 2A and FIG. 2B and FIG. 2C). The lens guard 210' is attached at its proximal end 214 to the laparoscope 100, and comprises a vent actuator 280, and a fluid conduit 270 that is in communication with the flow controller 220' (connection not shown). The flow controller 220' is depicted as an ergonomic device to be grasped in an operator's hand, with a flow actuator/regulator 250' adapted to be depressed by the operator's thumb, and a burst flow actuator/regulator 260' adapted to be depressed by the flexion of the operator's fingers, to deliver the flow of gas or liquid from one or more inlet sources (not shown) through the fluid conduit 270, for delivery to the objective lens of the scope through distal end 212 of the lens guard 210. In the depicted embodiment, the vent actuator 280 is under the control of the scope operator, and may be adjusted as needed to assist in maintaining visualization.

Of course it will be understood that in yet other alternate embodiments, one or more of the actuators may be eliminated, and their locations may be switched, or all actuators may be located on the flow controller 220' or may be located at yet another controller, such as a separate foot activated controller (not shown). In yet other embodiments, the lens guard 210 and 210' and the flow controller 220 and 220' could be provided as two or more separate pieces that are assembled for use. And it will further be appreciated that the two or more separate pieces that comprise the view optimizer 200 may comprise a lens guard 210/210' that is separate from the flow controller 220/220' and the lens guard and flow controllers are interconnected by one or more conduits for providing fluid flow. Once such embodiment is depicted in FIG. 2C, for example.

While the lens guard 210 and 210' and the flow controller 220 and 220' of the illustrated embodiments are formed from plastic, other suitable materials, such as metal or a composite material, or combinations of these could also be used.

According to some embodiments, the view optimizer 200 is adapted to deliver a stream of fluid to the objective lens of the laparoscope so as to create a current passing over the face of the lens that transports moisture located on or near the lens away from the lens, thus preventing moisture from adhering to the lens. In additional embodiments, the view optimizer 200 delivers a stream of fluid to the objective lens at a temperature that is adapted to help ensure that the temperature of the objective lens does not fall to a point that is at or below the dew point temperature within the patient's abdominal cavity, thus preventing condensation from forming on the lens. Finally, in yet additional embodiments, the view optimizer 200 is adapted to deliver a stream of generally anhydrous fluid to the objective lens. In such embodiments, the generally anhydrous fluid serves to attract and absorb moisture particles located on or near the lens and carry the moisture away from the lens with the flow of fluid. In some embodiments, the fluid is medical grade $CO_2$. Medical grade $CO_2$ for use with conventional insufflators is typically 99% pure, that is, no more than 1% of the gas is other than $CO_2$, and such medical grade $CO_2$ generally has a maximum moisture content of 25 parts per million by volume.

It should be understood that additional embodiments of the view optimizer 200 may perform only one of the above-described functions or any combination of these functions. Based on testing that was conducted in connection with the view optimizer 200 of the illustrated embodiment, when the temperature within the patient's abdomen was approximately 102.9° F. and the relative humidity within the patient's abdomen was 76%, the delivery of a stream of fluid to the objective lens of the laparoscope 100 at a flow rate of equal to or greater than 0.07 liters per minute proved to be effective for defogging the lens (and/or preventing the fogging of the lens). It should be understood, however, that a variety of different flow rates will be effective for defogging the lens depending on the temperature and the moisture content of the gas being supplied by the insufflator and the temperature and relative humidity of the patient's abdomen as well as other variables. As a way of illustrating the defogging effects of the view optimizer 200 according to one embodiment, the information regarding the dew point temperature of the objective lens of the laparoscope was collected when the view optimizer 200 was located within the patient's abdominal cavity.

According to some embodiments, the view optimizer 200 is adapted to deliver a stream of one or more fluids across the objective lens of the laparoscope 100 to deflect blood, bodily fluids, pieces of tissue, fat or other bodily material that come within the vicinity of the objective lens. The stream of fluid may be either continuous or intermittent. In addition, according to some embodiments, the view optimizer 200 is adapted to deliver a burst or bolus of gas and/or liquid to the objective lens of the laparoscope when the scope operator desires. This burst or bolus of gas and/or liquid serves, at least in part, to facilitate removal of blood, bodily fluids, pieces of tissue, fat or other bodily material on the objective lens. In this manner, the scope operator can deliver a burst of gas or liquid to the objective lens to remove a piece of material or droplet of liquid, which was otherwise unable to be removed from the objective lens. It should be understood that additional embodiments of the view optimizer 200 may perform only one of the above-described functions or any combination of these functions.

According to various embodiments, the view optimizer 200 delivers gas to the lens of the laparoscope so as to provide a guard or shield to deflect liquid and particulate debris and prevent it from contacting the lens. According to some embodiments, the gas delivery is intermittent. According to other embodiments, such as the embodiment illustrated in any one of FIG. 2A-2C, the flow of gas is essentially continuous. As such, the flow of gas during operation of the view optimizer 200 flows constantly, with delays of flow that are of a duration not greater than 5 seconds. Accordingly, in various embodiments wherein the flow of gas is essentially continuous, delays in flow are of a duration that is not greater than about 0.2, 0.4, 0.6, 0.8, 1.0, 2, 3, 4, or 5 seconds.

As is further described herein, the embodiment of the view optimizer 200 illustrated in any one of FIG. 2A-2C is supplied with gas by the insufflator comprises one or more of a variety of means to permit an essentially uninterrupted supply of gas to be directed across the objective lens of the laparoscope 100. Accordingly, the illustrated embodiment includes a leakage or venting of gas from the body cavity so as to ensure continuous gas flow from the insufflator. This leak allows gas to exit the patient's abdominal cavity as necessary to ensure that the insufflator remains substantially in an insufflation state, thus supplying the view optimizer 200 with a generally continuous supply of gas.

As previously described, the lens guard 210 is an elongated, cylindrical tube. However, it should be understood that that the lens guard 210 is not limited to this shape and configuration and other suitable shapes and configurations could also be used in additional embodiments. Examples of additional constructions have been previously described. Examples of additional cross-sectional shapes that could be used for the lens guard 210 include, but are not limited to, rectangular, triangular, oval, etc. The lens guard 210 can have any shape or configuration which allows it to surround the distal tip 120 of the laparoscope 100.

Additional embodiments of the view optimizer 200 may include a lens guard which has an angled portion to correspond with scopes with angled portions, such as 45° or 30° angled scopes. The lens guard 210 of the illustrated embodiment is substantially rigid. However, it should be understood that additional embodiments of the view optimizer may include a flexible lens guard, which is adapted for use with a flexible scope. For example, the lens guard 210 of the embodiment illustrated in FIG. 2A is fashioned from plastic, but other suitable materials such as metal or a composite material or combinations of these could also be used.

While the view optimizer 200 of the illustrated embodiment includes a lens guard 210 that surrounds and encloses the entire length of the laparoscope 100, it should be understood that the lens guard 210 of the view optimizer 200 could have any shape, construction or configuration that allows it to deliver gas and/or liquid to the objective lens of the laparoscope 100. For example, in alternative embodiments the lens guard 210 could be formed of one or more channels, tubes or conduits adapted to deliver gas and/or liquid to the objective lens of the laparoscope 100. The channels, tubes or conduits of such embodiments of the lens guard 210 could be supported by a rigid or flexible framework. The channels, tubes or conduits of such embodiments could also be fastened to the laparoscope 100 itself, either removably or permanently, by one or more fasteners, such as straps, ties, adhesives, clips, etc. In such embodiments, additional methods of sealing the interface between the view optimizer 200 and the trocar may be employed. For example, the portion of the view optimizer 200 that interfaces with the trocar may be a member that serves to form a seal with the trocar while the portion of the view optimizer 200 that is inserted into the patient's body cavity and delivers gas and/or liquid to the objective lens of the laparoscope could be one or more channel, tube or conduit and/or a rigid or flexible framework In addition, the lens guard 210 of additional embodiments could be adapted to surround and enclose only portions of the laparoscope 100, leaving other portions of the laparoscope 100 open and free from enclosure.

View Optimizer Stabilization: Scope Stabilizer

Figure 4A:
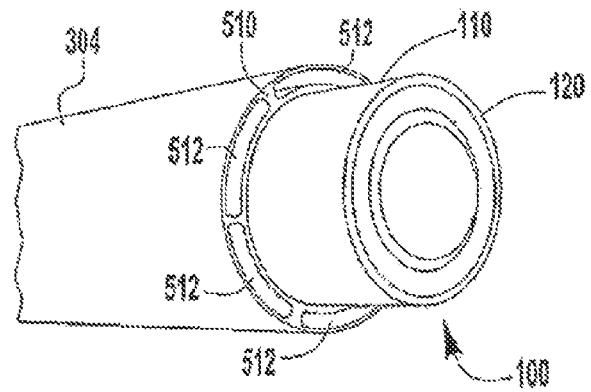
FIG. 4A shows a magnified perspective view of the guard tube of the lens guard of a view optimizer with a conventional laparoscope inserted therethrough.
Figure 4B:
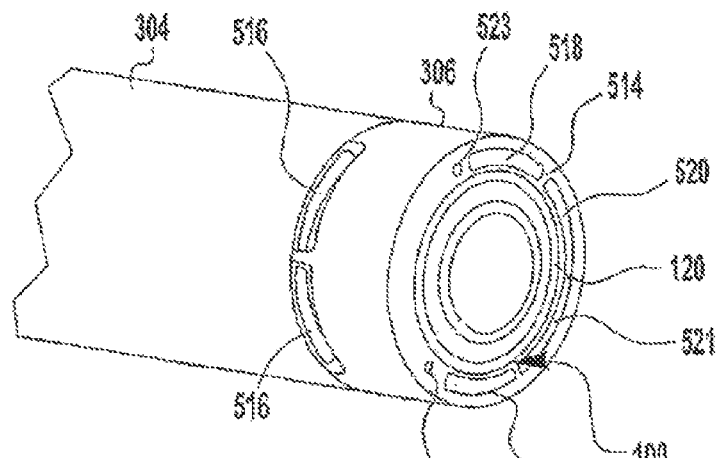
FIG. 4B shows a magnified perspective view of the guard tube and exhaust ring of the lens guard of a view optimizer.
Figure 4C:
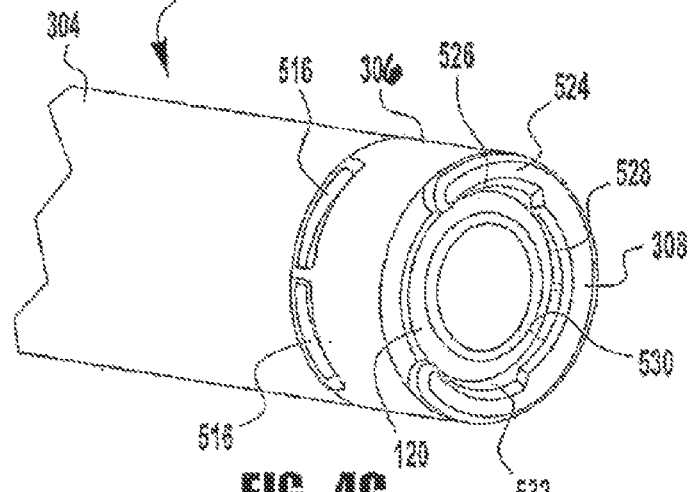
FIG. 4C shows a magnified perspective view of the guard tube, exhaust ring and end ring of the lens guard of a view optimizer.
Figure 4D:
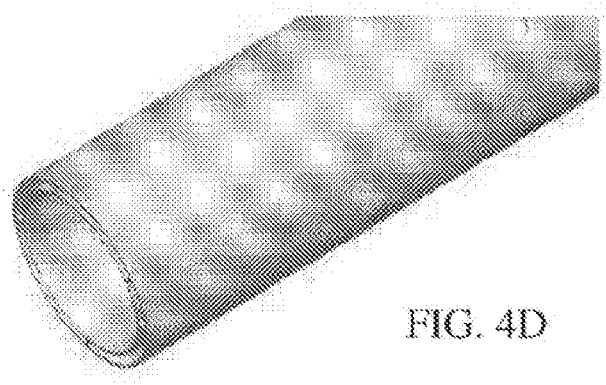
FIG. 4D shows a magnified perspective view of a guard tube and exhaust ring of the lens guard of the view optimizer of FIGS. 3A-3D adapted for use with a surgical scope having a 0° tip.
Figure 4E:
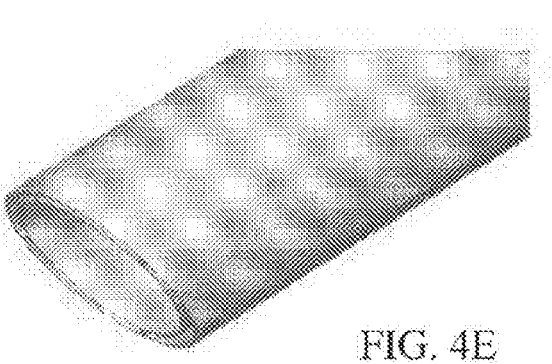
FIG. 4E shows a magnified perspective view of a guard tube and exhaust ring of the lens guard of the view optimizer of FIGS. 3A-3D adapted for use with a surgical scope having a 30° tip.
Figure 4F:
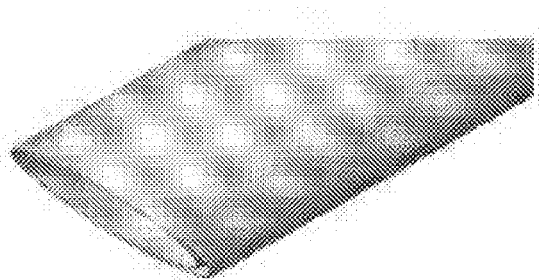
FIG. 4F shows a magnified perspective view of a guard tube and exhaust ring of the lens guard of the view optimizer of FIGS. 3A-3D adapted for use with a surgical scope having a 45° tip.
Figure 4G:
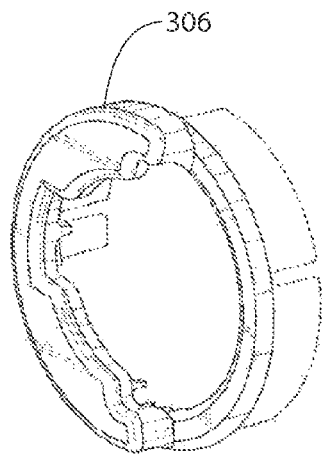
FIGS. 4G, 4H and 4I show a front perspective, rear plan and rear perspective views of an embodiment of the lens guard exhaust ring.
Figure 4H:
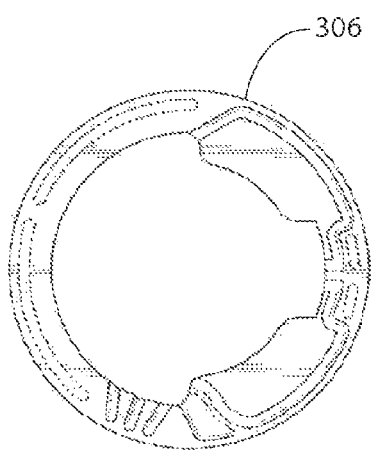
Figure 4I:
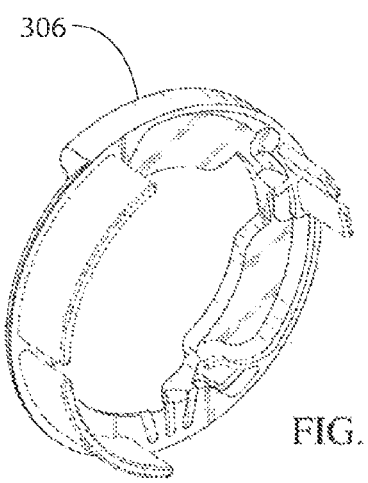
Figure 4J:
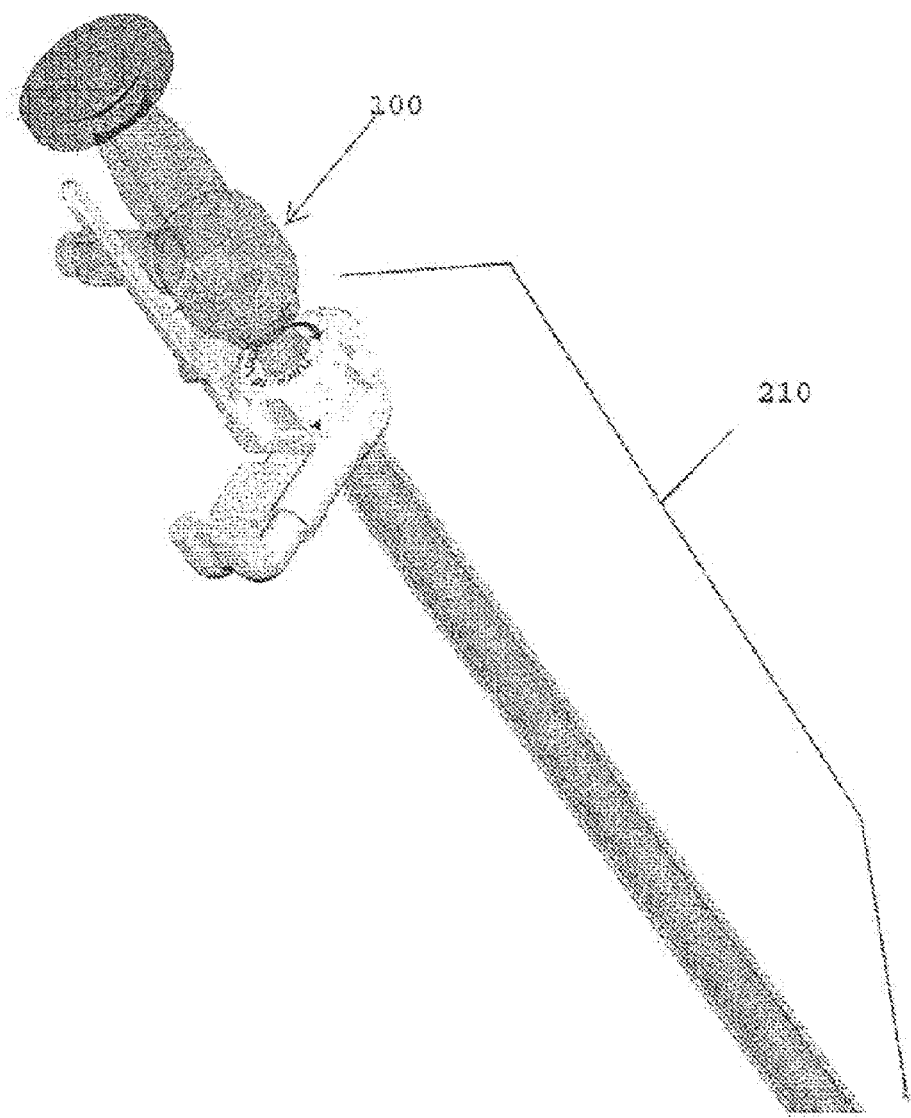
FIG. 4J shows an alternate side view of the lens guard depicted in FIG. 2C and FIG. 4K.
Figure 4K:
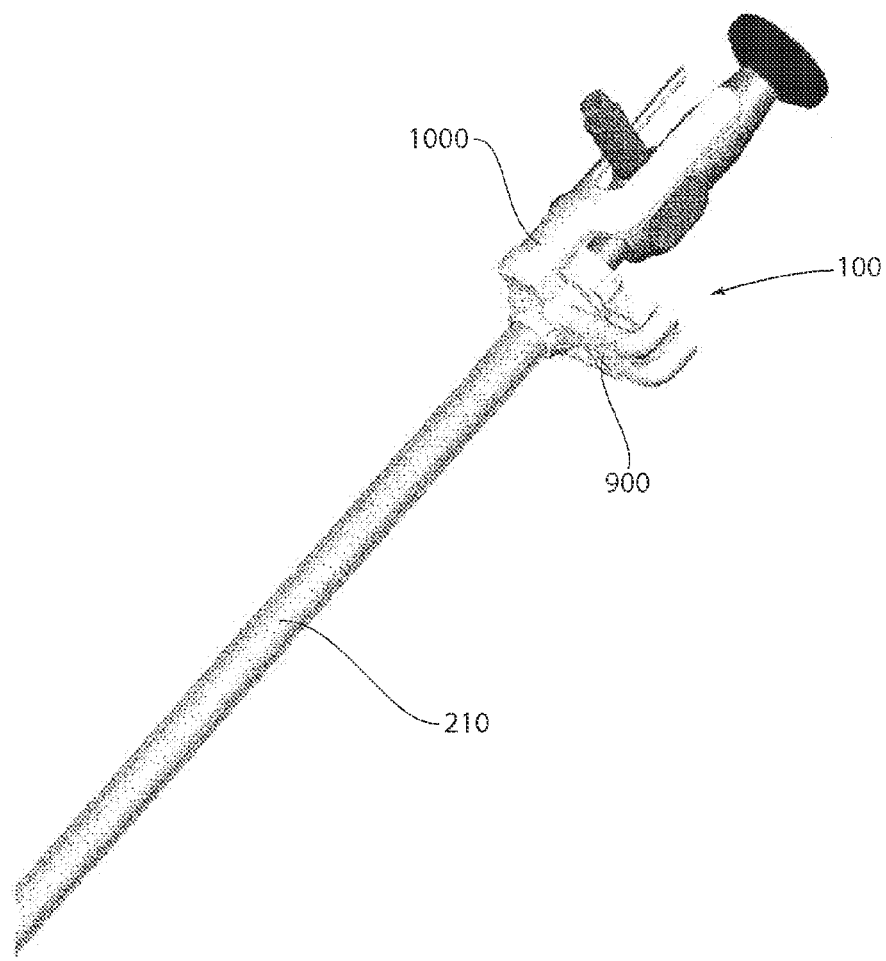
FIG. 4K shows a side perspective view of the lens guard depicted in FIG. 2C upper panel.
Figure 10:
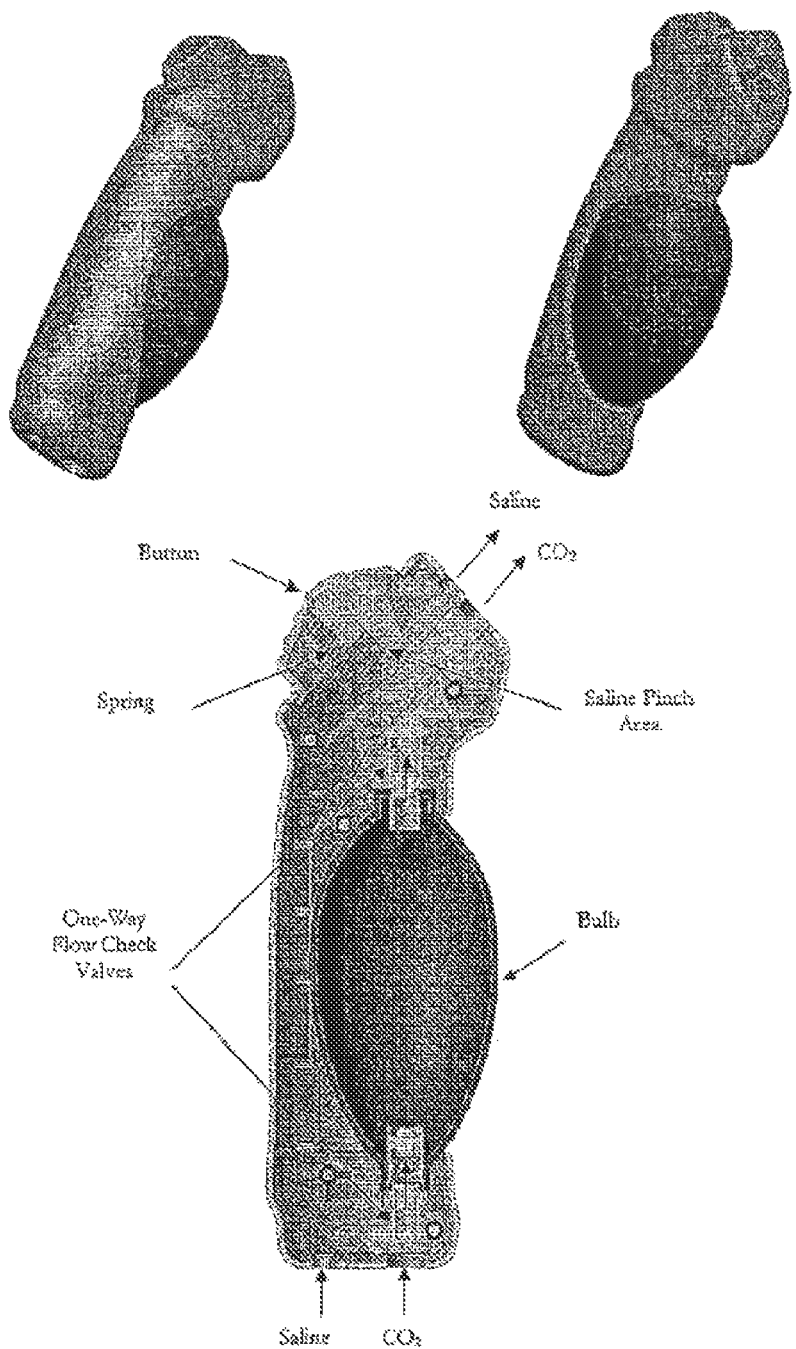
FIG. 10 shows alternate perspective views of the flow controller of the view optimizer of FIG. 2C and FIGS. 3A-3D and a cutaway view of the flow controller of the view optimizer of FIG. 2C, detailing the mechanisms for actuation of liquid flow and bolus flow of FIG. 2C and FIGS. 3A-3D.

Referring again to FIG. 2C, upper panel, the depicted exemplary embodiment of the view optimizer is a two-part design, comprising a lens guard that engages with a scope and a flow controller that is used to control and modulate various functions of the view optimizer. As depicted, the flow controller and the lens guard are in communication with one another via tubing elements that are in turn adapted to be in communication with one or more of water, gas and other sources. FIGS. 10, 4J and 4K, respectively, show perspective views of the flow controller 220 and lens guard 210 components shown in FIG. 2C. In its various embodiments, the view optimizer 200 is adapted to deliver to the objective lens of the laparoscope at least one fluid selected from, for example, a liquid, such as water or saline or a surfactant or other liquid, and a gas, such as $CO_2$ or air, to prevent the contact of material with the objective lens of the laparoscope or to defog or clean the objective lens of the laparoscope without the need to remove the laparoscope from the surgical field.

Referring now to FIG. 4J, the lens guard 210 of the illustrated embodiment is adapted to receive a portion of the laparoscope 100, most particularly the distal end 120 thereof, and a portion of the main body 110 of the laparoscope. The lens guard 210 can have any shape or configuration which allows it to surround the distal tip 120 of the laparoscope 100. Additional embodiments of the view optimizer 200 may include a lens guard which has an angled portion to correspond with scopes with angled portions, such as 45° or 30° angled scopes. For example, the lens guard 210 may be provided in a sheath configuration that has a zero angle or flat distal end 212 that corresponds with a non-angled scope. And in other embodiments, the lens guard 210 may be provided in a sheath configuration that has an angle other than zero at its distal end 212, where such angle corresponds to angled surgical scopes having standard angles of 45° or 30°, or, as will be appreciated by one of skill in the art, the tip may correspond to some other angle as may exist in the scope art. FIG. 4D-4F shows some embodiments of alternate tip configurations. FIGS. 4G-4I show different views of an embodiment of a lens guard tip. Thus, it will be appreciated that in accordance with the various possible lens guard 210 configurations that can be provided, any angle of scope can be accommodated simply by varying the angle of the distal end 212 of the lens guard 200.

Figure 15A:
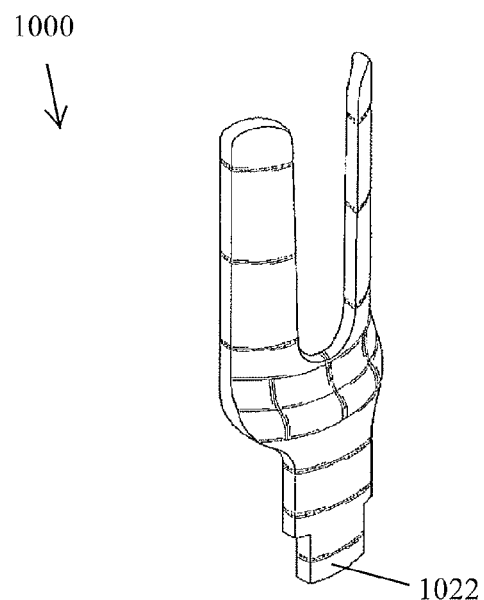
FIG. 15A shows a front perspective view of a surgical scope stabilizer.
Figure 15B:
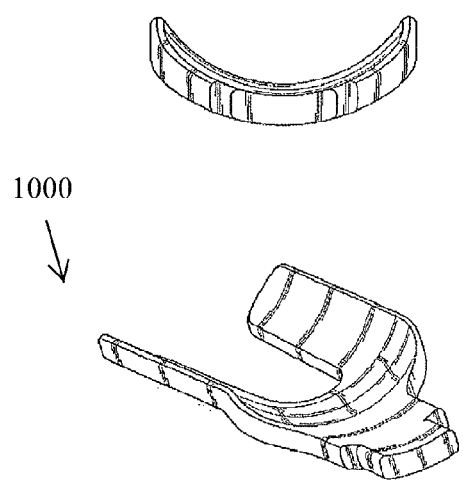
FIG. 15B upper panel is a bottom side view thereof; lower panel is a bottom perspective view thereof.
Figure 15C:
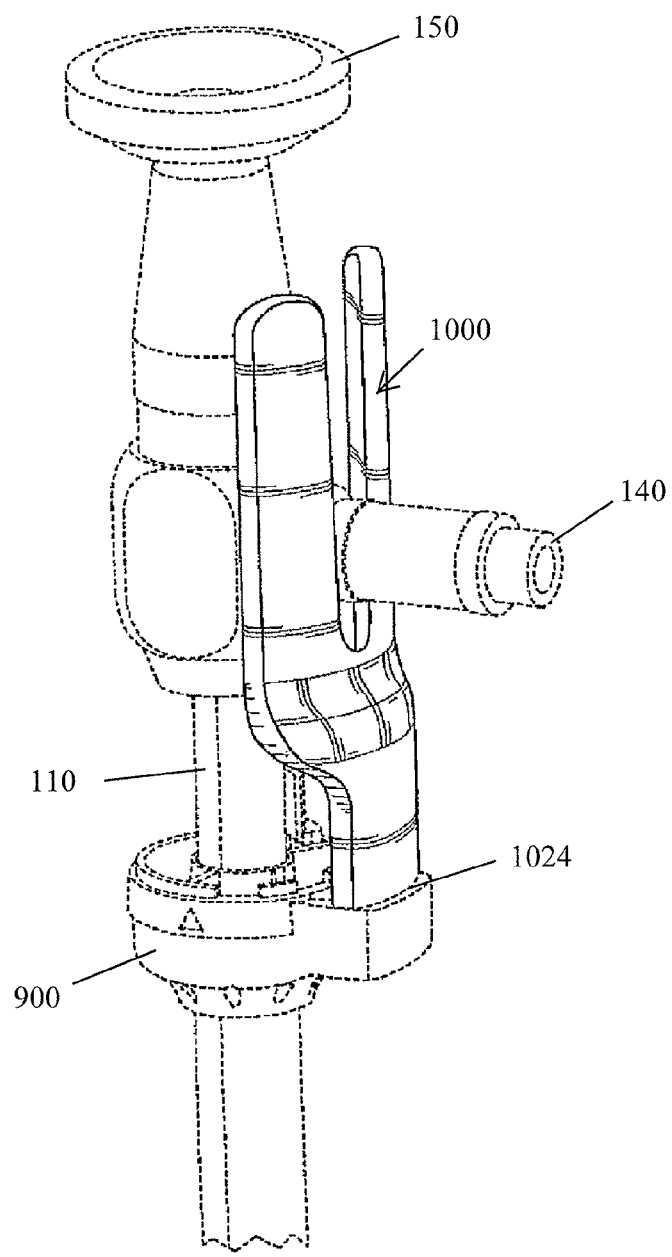
FIG. 15C is a front perspective view of a surgical scope stabilizer in the environment of a sheath manifold and surgical scope.

With respect to those lens guard 210 embodiments that have an angle other than zero at their distal end 211 for receiving variously angled scopes, proper alignment of the scope with the lens guard 210 is of importance to ensure proper function of the view optimizer 200 and to avoid disruption or fracture of the tip of the lens guard 210. Accordingly, a scope stabilizer is provided that serves the dual purpose of proper alignment of the scope when inserted into the lens guard 210 and maintenance and stabilization of that alignment during use. Referring again to FIGS. 4J and 4K, the scope stabilizer 1000 is shown engaged with the manifold 900 portion of the lens guard 210. The depicted scope stabilizer 1000 has a generally Y or fork-shaped configuration that has a proximal end for engagement with the lens guard 210 and a distal end for initially receiving and guiding a scope into position. The stabilizer 1000 has with two opposing parallel extension arms that are merged into a central base at the proximal end and extend to their tips the distal end and form a channel there between that is adapted to receive the illuminator connector 140 portion of the scope. The channel serves to guide the scope as it is inserted into proper engagements with the lens guard 210, and the arms forming the channel maintain the scope in proper position throughout the use of the view optimizer 200. FIGS. 15A-15C show various views of the scope stabilizer 1000, and FIG. 15C shows the scope stabilizer 1000 engaged with the lens guard 210 and an exemplary scope that is depicted in phantom (broken lines).

It will be understood that while the depicted embodiment of the scope stabilizer 1000 is constructed as a separate piece that is removably engageable with the manifold 900 of the lens guard 210, other embodiments are possible. Thus, the scope stabilizer 1000 may be formed in combination with one or more components of the lens guard 210, and as such, may be integrated with the manifold 900, or with some other component of the lens guard 210. It will also be understood that as a separate component, the scope stabilizer 1000 may be removably engageable by a variety of attachment means. As depicted, the scope stabilizer 1000 engages with the manifold 900 via a tab 1022 at its proximal end that inserts into a slot 1024 in the manifold 900. A variety of other means of attachment that are known in the art may be used, some of which may preclude removable engagement: such attachment or fasteners can include, but are not limited to, any type of screws or bolts, anchors, rivets, cotter pins, clips, snaps, straps, ties, adhesives, weldments, and the like.

As previously described, engagement of a scope with the lens guard 210 involves insertion of the scope through the lens guard 210 with proper orientation of the scope tip and the lens guard 210 tip. The disclosed scope stabilizer 1000 functions to guide and maintain stable orientation of the scope with the lens guard 210. Additional features of the lens guard 210 also operate to achieve and maintain stable engagement between an engaged scope and the lens guard 210. Referring again to FIG. 4K, the lens guard 210 includes structures that achieve and maintain engagement between the scope and the lens guard 210.

View Optimizer Construction

Referring now to FIGS. 3A-3D and FIG. 3E the view optimizer 200 will now be described with more particularity. In some embodiments, such as shown in FIG. 2A and FIG. 2C, and as shown in FIGS. 3A-3D, the view optimizer 200 is formed of discrete components that are interconnected, typically with tubing for transporting fluid. FIGS. 3A-3D in four panels show an exploded view of the device of FIG. 2C, which includes a hand held flow controller 220 connectable to a lens guard 210 via two or more tubing conduits. The various features and functionalities of devices according to this construction may be resident on one or both of the flow controller 220 and lens guard 210 components. That is, the controls for flow of liquid or gas, and delivery of a bolus or burst, as well as control of venting may be actuated from one or both components according to the various aspects of the disclosure herein. Moreover, the device components may be formed of one or multiple subcomponents as shown and described herein, such components and subcomponents being inter-connectable using connections and fastener means known in the art and as described variously herein.

Figure 3A:
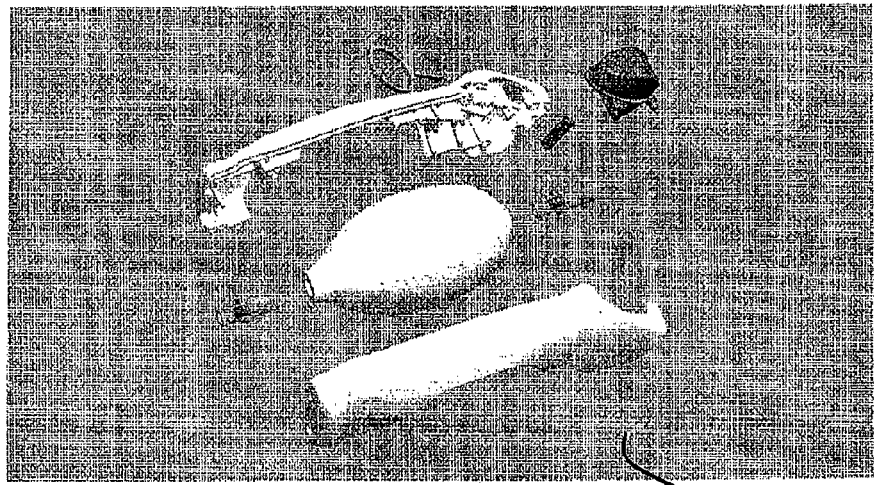
Figure 3B:
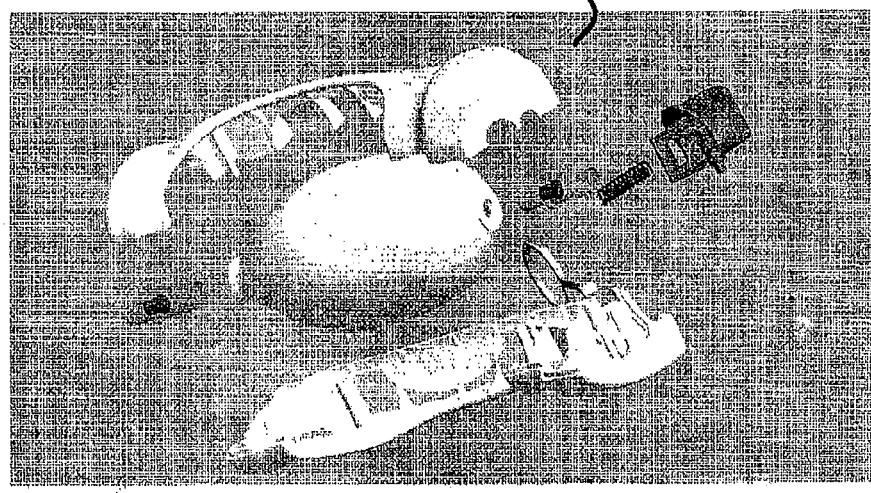
Figure 3E:
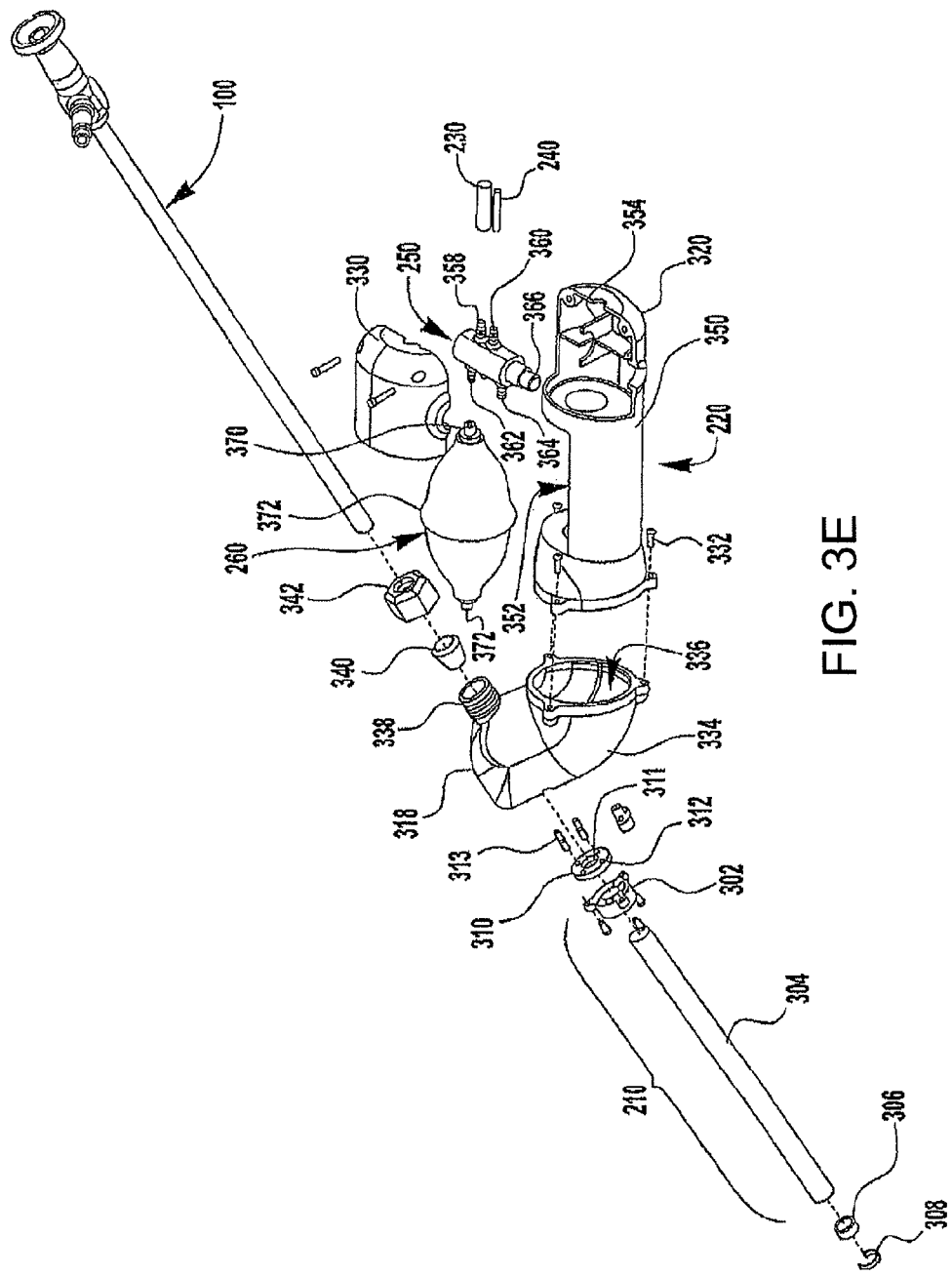
FIG. 3E shows an exploded perspective view of the view optimizer of FIG. 2B.

In other embodiments, such as shown in FIG. 2B, and as shown in FIG. 3E, the view optimizer 200 is of unitary construction, and the various features and functionalities of devices according to this construction may be resident on one or both of the flow controller 220 and lens guard 210 components. That is, the controls for flow of liquid or gas, and delivery of a bolus or burst, as well as control of venting may be actuated from one or both components according to the various aspects of the disclosure herein. Moreover, the device components may be formed of one or multiple subcomponents as shown and described herein, such components and subcomponents being inter-connectable using connections and fastener means known in the art and as described variously herein.

The view optimizers illustrated in FIGS. 3A-3D are shown with distal end 212 configurations that are zero angle. In accordance with the description provided herein, the view optimizer 200 could be alternately configured to be provided in one or more of an array of configurations. For example, referring to FIGS. 4D-4F, the lens guard 210 may be provided in a sheath configuration that has a zero angle or flat distal end 212 that corresponds with a non-angled scope (FIG. 4D). And in other embodiments, the lens guard 210 may be provided in a sheath configuration that has an angle other than zero at its distal end 212, where such angle corresponds to angled surgical scopes having standard angles of 45° (as shown in FIG. 4E) or 30° (as shown in FIG. 4E), or, as will be appreciated by one of skill in the art, the tip may correspond to some other angle as may exist in the scope art. Thus, it will be appreciated that in accordance with the various possible lens guard 210 configurations that can be provided, any angle of scope can be accommodated simply by varying the angle of the distal end 212 of the lens guard 200.

Figure 9B:
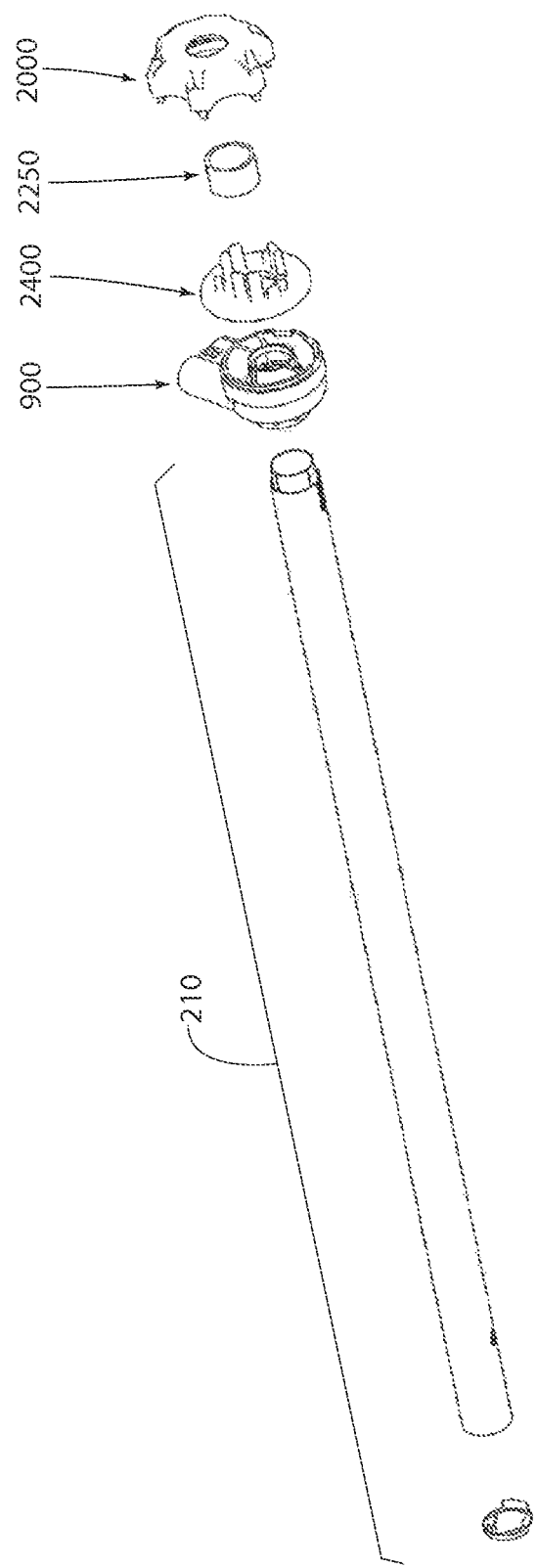
FIG. 9B and FIG. 9B' show an exploded perspective view of the lens guard of the view optimizer of FIG. 2C and FIGS. 3A-3D.

It will be further appreciated that the components of the lens guard 210 may be in multiple parts as described with respect to several of the illustrated embodiments as shown in FIG. 3E and FIG. 4A-C herein, or the lens guard 210 may alternatively be formed from fewer pieces such as depicted in FIG. 4D-F, and in FIG. 9, or in a single piece. According to embodiments of the lens guard 210 that are formed of two or multiple pieces, the discrete pieces may be connected by any one or combination of fastening means, such as, for example, tongue and groove, threaded, snap fit, or other fastening means as described herein or more generally known in the art.

The illustrated embodiments of the view optimizer 200 are adapted to deliver a generally continuous flow of gas to the objective lens of a laparoscope 100 via end ring 308 of the lens guard 210 for the cleaning and/or defogging of the lens and to deliver a flow of liquid to the objective lens of the laparoscope 100 when the operator desires. It should be understood that additional embodiments of the view optimizer 200 may be adapted to deliver a generally continuous flow of only liquid to the objective lens of the laparoscope 200 or both liquid and gas simultaneously. In addition, additional embodiments of the view optimizer 200 may be adapted to not deliver a continuous flow of gas and/or liquid but, rather, be adapted to only deliver a flow of gas and/or liquid upon the activation of an actuation device.

The illustrated embodiment of the view optimizer 200 is also adapted to deliver a burst or bolus of gas to the objective lens of the laparoscope upon the activation of a burst actuator/regulator 260. It should be understood that additional embodiments of the view optimizer may be adapted to deliver a burst or bolus of liquid to the objective lens of the laparoscope 200. It should also be understood that additional embodiments of the view optimizer may be provided without this burst function.

Finally, the illustrated embodiment of the view optimizer 200 is adapted to create a controlled leak of the gases from within the patients abdominal cavity to ensure that the insufflator does not turn off during a surgical procedure or to diminish the frequency of such stoppages of the insufflator. It should be understood that all embodiments of the view optimizer do not include such a controlled leak function. In addition, yet additional embodiments of the view optimizer 200 may create a steady leak, which is not controllable by the operator.

View Optimizing Devices—Lens Guard Distal End Construction

Referring again to FIG. 3E, the lens guard 210 of the illustrated embodiment includes an adapter ring 302, a guard tube 304, an exhaust ring 306, and an end ring 308. FIG. 4A-4C provide additional detail regarding the tip of the lens guard 210. Referring first to FIG. 4A, the guard tube 304 is shown with more particularity (the exhaust ring 306 and end ring 308 of the lens guard 210 are not present in FIG. 4A to better illustrate the construction of the guard tube 304). As shown in FIG. 4A, the guard tube 304 is a hollow, cylindrical tube adapted to surround the laparoscope 100. The guard tube 304 has an outer wall 510 that defines a hollow space. Also as shown in FIG. 4A, channels 512 are defined within the outer wall 510 and extend the length of the guard tube 304. The channels 512 are adapted to allow for the travel of gas and/or fluid along the length of the guard tube 318. The guard tube 304 depicted in the figures includes six channels 512, each having one or more functions. However, it should be understood that additional embodiments of the view optimizer may include any number of channels 512 defined within the guard tube 304, such as, for example, a single channel for multiple functions, or two or more channels each having distinct functions. The channels 512 may have a variety of sizes, shapes and configurations that allow for the passage of gas and/or liquid. The guard tube 318 of the illustrated embodiment shown in FIG. 5 has two channels 512 for the passage of exhaust gas from the interior of the patient's body cavity, and is suitable for providing a controlled leak. The illustrated embodiment also includes two channels dedicated to delivery of gas from the insufflator to the objective lens of the laparoscope 100, and one channel for the passage of the liquid to the objective lens of the laparoscope. Additional embodiments of the view optimizer 200 may include guard tubes 304 that have any number of channels 512 dedicated to any combination of gas for delivery to the objective lens of the laparoscope, liquid for delivery to the objective lens of the laparoscope, and/or exhaust gas. As mentioned previously, various additional embodiments of the view optimizer 200 may utilize both gas and liquid or only one of gas or liquid for delivery to the objective lens of the laparoscope. In some embodiments, the view optimizer may lack exhaust channels. Generally, depending on the intended functionality of the lens guard, the one or multiple channels 512 of the guard tube 304 will be suitably adapted.

Referring now to FIG. 4B, the guard tube 304 and exhaust ring 306 of the lens guard 210 are shown in use with a laparoscope 100 (the end ring 308 of the lens guard 210 is not shown in FIG. 4B to better illustrate the construction of the exhaust ring 306). The exhaust ring 306 is a hollow, cylindrical piece adapted to surround and enclose a portion of the laparoscope 100. As shown in FIG. 4B, the guard tube 304 and the exhaust ring 306 of the view optimizer 200 are attached together. The guard tube 304 and the exhaust ring 306 can be attached together in a variety of different ways, such as by adhesives, screws, tabs and slots, etc. In addition, the guard tube 304 and exhaust ring 306 could be formed together as a unitary construction.

The exhaust ring 306 has an outer wall 514 which defines a hollow space. Exhaust vents 516 are defined within the outer wall 514 of the exhaust ring 306. As shown in FIG. 4B, the guard tube 304 and the exhaust ring 306 abut against one another when the lens guard 210 is assembled. The exhaust vents 516 defined within the outer wall 514 of the exhaust ring 306 are adapted to form openings into two of the channels 512 of the guard tube 304 that are dedicated to the passage of exhaust gas from within the patient's body cavity in conjunction with the leak function of the view optimizer 200 of the illustrated embodiment. The pressure within the patient's body cavity is greater than the pressure within the channels 512 of the guard tube 304. Accordingly, gas from within the patient's body cavity will enter the exhaust vents 516 and travel through the channels 512 defined within the guard tube 304 out of and away from the patient's body cavity. While the embodiment of the exhaust ring 306 illustrated in FIG. 4B includes two exhaust vents 516, additional embodiments of the view optimizer 200 may include exhaust rings 306 with any number of exhaust vents. The exhaust vents 516 may have any shape, size and configuration which allows gas to enter the guard tube 304 or some other portion of the view optimizer 200. As discussed above, additional embodiments of the view optimizer 200 may lack a controlled leak function, thus, such embodiments of the view optimizer 200 will not include exhaust vents 516.

Referring again to FIG. 4B, channels 518, 520, 521 and 522 are defined within the outer wall 514 of the exhaust ring 306 and extend through the length of the exhaust ring 306. The channels are adapted to allow for the travel of either gas and/or liquid along the length of the exhaust ring 306. When the lens guard 210 is assembled, each of the channels 518, 520, 521 and 522 of the exhaust ring 306 align with a channel 512 of the guard tube 304 to allow for the passage of gas and/or liquid therethrough. While the exhaust ring 306 of the illustrated embodiment includes four channels, additional embodiments of the view optimizer may include exhaust rings 306 with any number of channels.

As depicted, channel 518 of the exhaust ring 306 of the illustrated embodiment is adapted for the passage of liquid for delivering to the objective lens of the laparoscope 100. Channels 520, 521 are adapted for the passage of gas for delivery to the objective lens of the laparoscope 100. Channel 522 of the exhaust ring 306 of the illustrated embodiments is not operative to allow for the passage of either gas and/or liquid. However, in additional embodiments, channel 522 could be functional. Channel 522 could act as an exhaust channel for both fluid and gas. While the exhaust ring 306 includes four channels, it should be understood that additional embodiments of the exhaust ring 306 may include any number of channels. The channels 518, 520, 521 and 522 may have a variety of sizes, shapes and configurations. The channels 518, 520, 521 and 522 can have any size, shape and configuration that allows for the passage of gas and/or liquid. As mentioned previously, various additional embodiments of the view optimizer 200 may utilize both gas and liquid or one of gas or liquid for delivery to the objective lens of the laparoscope for cleaning and/or defogging. Accordingly, such factors will determine the usage and number of channels as well as the construction, size, shape and configuration of the end ring 308 of additional embodiments of the view optimizer 200.

As shown in FIG. 4B, the exhaust ring 306 includes fastener openings 523 for use in the attachment of the end ring 308. As shown in FIG. 4C, the exhaust ring 306 and the end ring 308 of the view optimizer 200 are attached together. The exhaust ring 306 and the end ring 308 of the illustrated embodiment are attached together by projections (not shown) which extend from the end ring 308 and are received within the fastener openings 523 of the exhaust ring 306. However, it should be understood that the end ring 308 and the exhaust ring 306 can be attached together in a variety of different ways, such as by adhesives, screws, tabs and slots, etc. In addition, the end ring 308 and exhaust ring 306 could be formed together as a unitary construction.

Referring now to FIG. 4C the guard tube 304, exhaust ring 306 and end ring 308 are shown in use with a laparoscope 100. The end ring 308 is attached to the exhaust ring 306 and extends beyond the end of the laparoscope 100. This extension of the end ring 308 beyond the distal end 120 of the laparoscope 100 facilitates delivery of fluid to the lens, as further described herein, and helps to shield the objective lens from contacting objects or tissue, either within the patient's body cavity or outside of it, such as within the passageway within a trocar, that may soil, smudge, smear or adhere to the objective lens of the laparoscope. For example, conventional trocars include a seal assembly that consists of a plurality of flaps that create a seal with objects that are inserted through the trocar. These flaps of the trocar seal can become soiled with blood, bodily fluids, pieces of tissue, fat or other bodily material during an operative procedure. The extension of the end ring 308 beyond the distal end 120 of the laparoscope 100 serves to contact these flaps prior to the laparoscope 100 as the laparoscope 100 and view optimizer 200 are being inserted through the trocar, thereby deflecting the soiled flaps away from contacting the objective lens of the laparoscope 100, and thus, preventing any blood, bodily material or other matter that is on the flaps from contacting and/or dirtying the objective lens. Likewise, the extension of the end ring 308 beyond the distal end 120 of the laparoscope also serves to deflect objects, such as internal organs or other tissue or fat, from contacting the objective lens of the laparoscope 200 when within the patient's body cavity.

According to various embodiments, the end ring 308 portion of the view optimizer 200 may extend beyond the end of the laparoscope from about 0 mm to about 7 mm, Accordingly, in various embodiments, the end ring 308 portion of the view optimizer 200 may extend beyond the end of the laparoscope from about 0, 0.5, 1, 1.5, 2, 2.5, 3, 3.5, 4, 4.5, 5, 5.5, 6, 6.5, 7 mm or more. It should be understood that additional embodiments of the view optimizer 200 may not include an end ring 308 or other structure that extends beyond the distal end 120 of the laparoscope 100.

The end ring 308 is adapted to partially enclose the distal end 120 of the laparoscope 100. The end ring 308 has a main wall 524. Passageways 526, 528, 530 and 532 are defined within the main wall 524 of the end ring 308. Passageways 526, 528, 530 and 532 are adapted to direct the flow of gas and/or liquid exiting the channels 518, 520, 521 of the exhaust ring 306 across the operative lens of the distal end 120 of the laparoscope. The passageways 526, 528, 530 and 532 of the illustrated embodiment of the view optimizer 200 direct at least a portion of the flow of gas and/or liquid across the face of the objective lens. In the sheath assembly 200 of the illustrated embodiment, passageway 526 is adapted to direct the flow of liquid from channel 518 of the exhaust ring 306 across the objective lens of the laparoscope 100. Channels 528, 530 of the illustrated embodiment are adapted to direct the flow of the gas from channels 520, 521 of the exhaust ring 306 across the objective lens of the laparoscope 100 to deflect gas and liquid from the lens, defog the objective lens as well as to remove moisture or material from the surface of the objective lens. Channels 528, 530 are also adapted to direct at least a portion of the gas from channels 520, 521 in a path that projects forward from the objective lens (as viewed in FIG. 4C) at an angle relative to the objective lens. The flow of the gas that is directed forward from the distal end 120 of the laparoscope further serves to deflect away smoke, particulate, blood, bodily fluid, moisture, tissue, fat, or other material within the patient's body cavity from contacting the objective lens of the laparoscope 100. Accordingly, as the laparoscope 100 is inserted into the patient's body cavity and/or moved within the cavity, this forwardly projecting flow of gas serves to deflect away blood or other material that approaches the objective lens.

It should be understood that additional embodiments of the view optimizer 200 could direct all of the gas and/or liquid across the objective lens in a path that is generally parallel to the objective lens or could direct all of the gas and/or liquid in a path projecting forward and away from the distal end 120 of the laparoscope at an angle relative to the objective lens, or could direct all or a portion of the gas and/or liquid in a path projecting toward the distal end 120 of the laparoscope 100 at an angle relative to the objective lens, or any combination of parallel flow and angled flow.

Embodiments of the view optimizer 200 may provide for the delivery of gas and/or liquid in a path having any angle relative to the objective lens between 0° and 90° or between 0° and −90°, wherein the negative designation refers to paths directed toward the lens. In some embodiments, fins or louvers are provided to direct the flow of the gas and/or liquid in a variety of different paths each having a different angle relative to the objective lens, thereby, creating a fanned out flow of gas and/or liquid. According to various embodiments, the length of extension of the end ring 308 portion of the view optimizer 200 that extends beyond the end of the laparoscope from about 0 mm to about 7 mm may comprise one or more passageways that deliver a fluid stream at one or a range of positions along the length of the end ring 308. According to such embodiments, the passageways may be positioned at the base of the end ring 308, near to the lens of the scope, or at the distal end of the end ring 308, farthest away from the lens, or at one or more locations in between. And according to such various embodiments, the passageways may be configured to direct a narrow stream of fluid, or may be configured to direct a fan of fluid at various angles.

It will be appreciated then that a stream of fluid may be directed from one or multiple channels, and that each stream may be directed within a range of possible paths from parallel to perpendicular relative to the lens, and that each such flow path may be parallel or perpendicular to or transect at some angle in between the path of another stream, and that in some embodiments each such flow path may be directed towards the channel from which another stream of fluid is emitted. Accordingly, in some embodiments, a stream of fluid in the form of gas may be directed towards the channel from which another stream of gas is emitted, or a stream of fluid in the form of gas may be directed towards the channel from which another stream of liquid is emitted, or a stream of fluid in the form of liquid may be directed towards the channel from which another stream of liquid is emitted, or a stream of fluid in the form of gas may be directed towards the channel from which another stream of gas is emitted.

The embodiment depicted in FIG. 4C is configured with an end ring 308 that extends about 2 mm from the end of the laparoscope and is configured to deliver a fan of air at an angle of about 30°, thus the distance of the flow path nearest the lens at the point of the passageway is about 0 mm and the distance of the flow path nearest the lens at the opposite side of the lens is about 8 mm from the lens. Variation of the length of the end ring, distance of the passageway from the lens, angle or angles of flow may vary, such that the distance of the nearest flow path from the lens may range from 0 mm to more than 15 mm, and in some embodiments the flow path may be directed at an angle toward the lens.

The end ring 308 of additional embodiments an have a variety of sizes, shapes and configurations. The end ring 308, can have any size, shape or configuration that allows it to direct gas and/or liquid across the face of the objective lens of the laparoscope. While the end ring 308 of the illustrated embodiment only partially encircles the distal end 120 of the laparoscope 100, it should be understood that additional embodiments of the view optimizer 200 may include an end ring 308 that completely encircles the distal end 102 of the laparoscope 100. As mentioned previously, various additional embodiments of the view optimizer 200 may utilize both gas and liquid or one of gas or liquid for delivery to the objective lens of the laparoscope for cleaning and/or defogging. In addition, additional embodiments of the view optimizer 200 may not include a controlled leak function. Accordingly, such factors will affect the construction, size, shape and configuration of the end ring 308 of additional embodiments of the view optimizer 200.

Figure 5A:
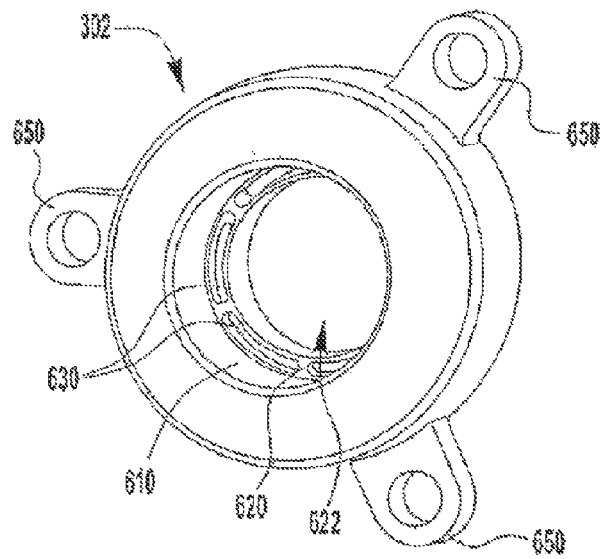
FIG. 5A shows a magnified front perspective view of the adapter ring of the lens guard of the view optimizer of FIG. 2B.
Figure 5B:
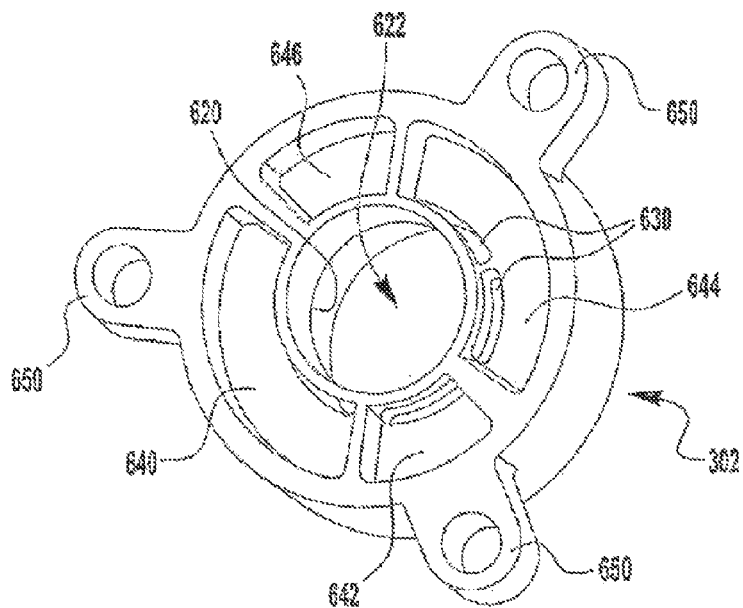
FIG. 5B shows a magnified rear perspective view of the adapter ring of the lens guard of the view optimizer of FIG. 2B.
Figure 7:
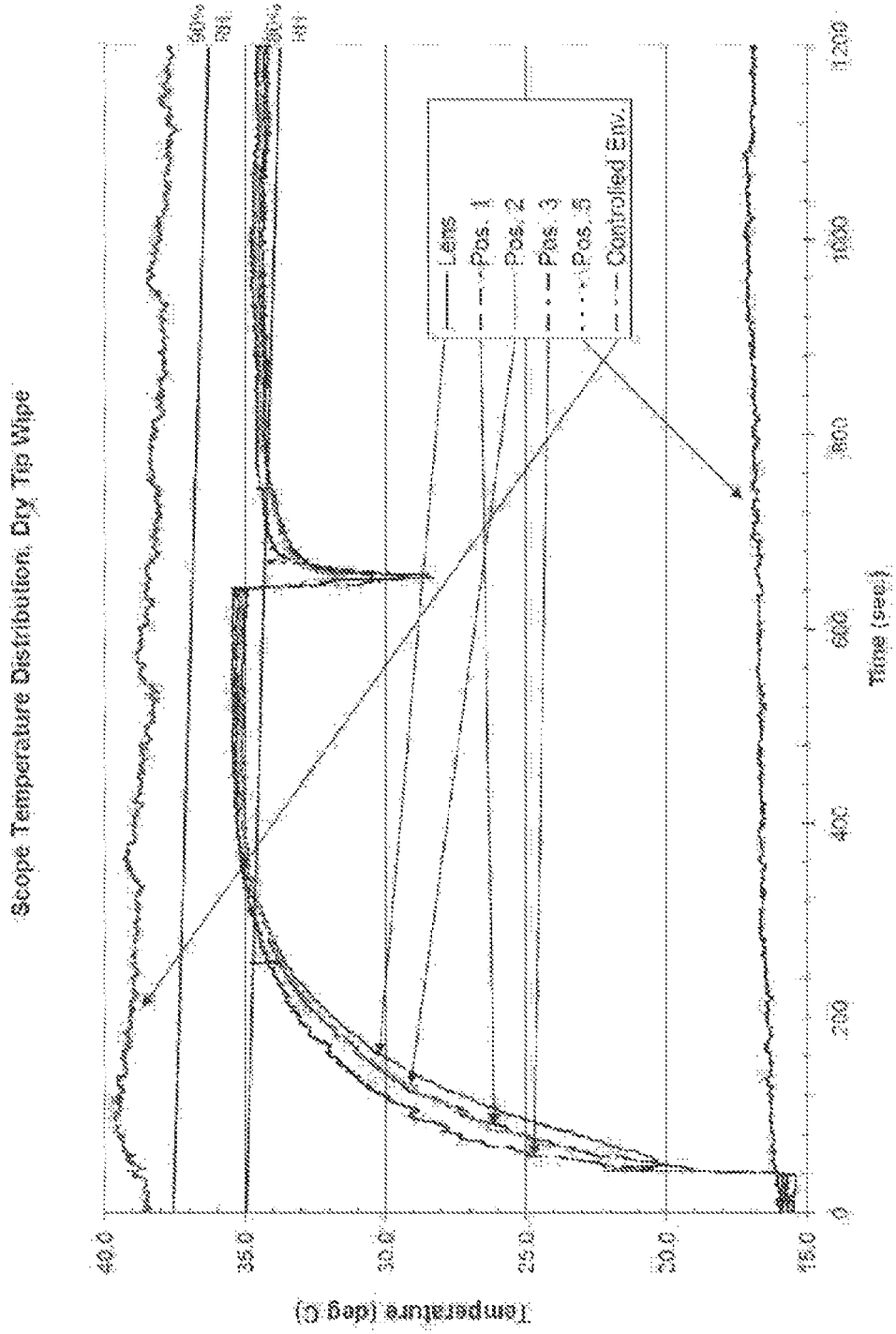
FIG. 7 shows results of analysis of humidity and fogging.

Referring again to FIG. 3E, an adapter ring 302 is located at the proximal end 214 of the lens guard 210 to permit connection of the lens guard 210 to the flow controller 220. The adapter ring 302 is adapted to mount the lens guard 210 to the main body. The adapter ring 302 can have any size, shape or configuration that allows it to mount the lens guard 210 to the flow controller 220. In addition, as mentioned previously, the lens guard 210 and flow controller 220 of additional embodiments may be formed as a unitary piece or may also be located remotely from one another and not directly connected to one another. FIG. 5A-C shows greater detail with respect to the attachment of the lens guard 210 and the flow controller 220. As shown in FIG. 5A, the adapter ring 302 has a generally cylindrical shape with a guard tube opening 610 defined through it. The guard tube opening 610 is adapted to receive the guard tube 304. The guard tube opening 610 of the adapter ring has an inner rim 620. When the guard tube 304 is inserted into the adapter ring, the guard tube 304 abuts against the inner rim 620. In this manner, the inner rim 620 helps to properly locate the guard tube 304 within the adapter ring 302 and prevents the guard tube 304 from passing completely through the adapter ring 302. Several channels 630 are defined within the inner rim 620 of the adapter ring and pass through the length of the adapter ring 302. The adapter ring 302 of the illustrated embodiment of the view optimizer has six channels 630 to coincide with the six channels 512 of the guard tube 304. When the guard tube 304 is secured within the adapter ring 302, the channels 512 of the guard tube 304 align with the channels 630 of the adapter ring, to allow for gas and/or liquid to flow from the channels 512 of the guard tube to the coinciding channels 630 of the adapter ring 302 and vice versa.

While the adapter ring 302 of the illustrated embodiment includes six channels 630, it should be understood that additional embodiments of the adapter ring 302 may include any number of channels 630. The channels 630 may have a variety of sizes, shapes and configurations. The channels 630 can have any size, shape and configuration that allows for the passage of gas and/or liquid. As mentioned previously, various additional embodiments of the view optimizer 200 may utilize both gas and liquid or one of gas or liquid for delivery to the objective lens of the laparoscope for cleaning and/or defogging. Accordingly, such factors will determine the usage and number of channels 630 as well as the construction, size, shape and configuration of the adapter ring 302 of additional embodiments of the view optimizer 200.

As shown in FIG. 5A, a laparoscope opening 622 is defined within the inner rim 620 of the adapter ring. The laparoscope opening 622 is adapted to receive the laparoscope 100 and allow for the laparoscope 100 to enter the guard tube 304. The laparoscope opening 622 may be any size, shape or configuration that allows for the receipt of the laparoscope 100.

Referring now to FIG. 5B, a rear perspective view of the adapter ring 302 is shown. As shown in FIG. 5B, the laparoscope opening 622 extends through the adapter ring 302. Also as shown in FIG. 5B, the channels 630 defined within the adapter ring 302 extend to the rear of the adapter ring 302 and open into arcuate shaped openings 640, 642, 644 and 646 defined within the rear surface of the adapter ring 302. As can be seen in FIG. 5B, two of the channels 630 connect with opening 640, one channel 630 connects with opening 642, two of the channels 630 connect with opening 644 and one of the channels 630 connects with opening 646. In this manner, one pair of the channels 630 are jointly connected to opening 640 and one pair of the channels are jointly connected to opening 644. Accordingly, the gas and/or liquid traveling through such channels 630 will jointly flow through openings 640 and 644. Also, any gas and/or liquid which enters openings 640 or 644, will flow into the pair of channels 630 connected with opening 640 or 644. Consequently, this allows for one source of gas and/or liquid to be divided into the flow of gas and/or liquid through a pair of channels 630 of the adapter ring and, consequently, a pair of channels 512 of the guard tube 304.

In the illustrated embodiment of the view optimizer 200, opening 640 is adapted to receive gas for delivery to the objective lens of the laparoscope 100 through the lens guard 210, opening 642 is adapted to receive liquid for delivery to the objective lens of the laparoscope 100 through the lens guard 210, and opening 644 is adapted for the passage of the exhaust gases leaving the patient's body cavity via exhaust vents 516 and passing through the lens guard 210. In the illustrated embodiment of the view optimizer 200, opening 646 is not operable to receive the flow of either gas or liquid, however in additional embodiments of the view optimizer 200, opening 646 may be functional. As mentioned previously, various additional embodiments of the view optimizer 200 may utilize both gas and liquid or one of gas or liquid for delivery to the objective lens of the laparoscope for cleaning and/or defogging. In addition, additional embodiments of the view optimizer may not include a controlled leak function. Accordingly, such factors will affect the construction, size, shape, configuration and functionality of the adapter ring 302, the channels 630 of the adapter ring 302, and the openings 640, 642, 644, and 646 of the adapter ring 302 of additional embodiments of the view optimizer 200.

Referring again to FIG. 3E, the view optimizer 200 includes a connection plate 310 that is adapted to abut the adapter ring 302. The connection plate 310 of the illustrated embodiment is a generally planar, circular disc with a central opening 311 defined through it, and is adapted to permit the laparoscope 100 to pass through the connection plate 310. The connection plate 310 also has four openings 312 defined through it radially outward from the central opening 311. The openings 312 are adapted to receive fluid connectors 313. While the connection plate 310 of the illustrated embodiment has four fluid connectors 313, additional embodiments of the connection plate 310 may have any number of fluid connectors 313. The connection plate 310 is adapted to abut against the adapter ring 302 and seal against the openings 640, 642, 644 and 646. Each of the four fluid connectors 313 mounted within the connection plate 310 coincides with one of the openings 640, 642, 644 and 646 of the adapter ring 302 described in connection with FIG. 5. Thus, fluid flowing through one of the fluid connectors 313 is free to pass through the connection plate 310 into one of the openings 640, 642, 644 and 646 of the adapter ring, through the channels 630 of the adapter ring, through one of the channels 512 of the guard tube, through one of the channels of the exhaust ring and through the end ring 308 for delivery to the objective lens. In addition, exhaust gas that enters the exhaust vents 516 may pass up the guard tube 304, through the adapter ring 302 and into one of the fluid connectors 313. Additional embodiments of the view optimizer may not include a connector plate 310 or fluid connectors 313.

Referring again to FIG. 5B, projecting outwardly from the adapter ring 302 are three fastener portions 650, each fastener portion 640 having a fastener opening defined therethrough. As shown in FIG. 6, the fastener portions 650 are utilized to mount the adapter ring 302 and, consequently, the lens guard 210 to the flow controller 220. Additional embodiments of the sheath assembly 200 may have any number of fastener portions 650. The adapter ring 302 of the illustrated embodiment is attached to the flow controller 220 with conventional screws, however, other suitable fasteners, such as adhesives, rivets, tab and slots, etc. could also be used. When the adapter ring 302 and lens guard 210 are mounted to the flow controller 220, the fluid connectors 313 project into the interior of the flow controller 220. Also, as mentioned previously, the lens guard 210 and the flow controller 220 may be formed as a one-piece construction in additional embodiments of the view optimizer 200 or may be located remotely from one another and not directly connected to one another. As a result, all embodiments of the view optimizer 200 may not include an adapter ring 302. It should be understood that additional embodiments of the view optimizer 200 may utilize various methods for mounting the lens guard 210 to the flow controller 220.

View Optimizing Devices—Flow Controller Construction

Referring again to FIG. 3E, the flow controller 220 will be described with more particularity. The flow controller 220 of the illustrated embodiment of the view optimizer 200 generally includes a base portion 318, a handle portion 320 and an end cap 330. The base portion 318, handle portion 320 and end cap 330 of the illustrated embodiment are adapted to surround and enclose other portions of the view optimizer 200. The base portion 318, handle portion 320 and end cap 330 of the illustrated embodiment are molded from plastic, however, other suitable materials can also be used. It should be understood that the base portion 318, handle portion 320 and end cap 330 of the view optimizer 200 are not limited to the size, shape or configuration set forth in FIGS. 3A-3D or FIG. 3E. The base portion 318, handle portion 320 and end cap 330 of the flow controller 220 of the view optimizer 200 can have any size, shape or configuration that can support and/or enclose other components of the view optimizer 200.

The base portion 318, handle portion 320 and end cap 330 are fastened together with a plurality of fasteners 332. The fasteners 332 of the illustrated embodiment are conventional screws, however, it should be understood that any suitable attachment means could be used. Examples of additional fasteners that can be used include, but are not limited to, any type of screws or bolts, anchors, rivets, cotter pins, clips, snaps, straps, ties, adhesives, weldments, etc. In addition, it should be understood that the flow controller 220 could be formed as one unitary piece in additional embodiments, and need not be provided as multiple pieces that are assembled together.

The base portion 318 of the flow controller 220 has an outer wall 334 that defines an interior cavity 336. The configuration of the interior cavity 336 of the base portion 318 is adapted to support and enclose other components of the view optimizer 200. A scope receiver portion 338 extends from the outer wall 334 of the base portion 318 and opens into the interior cavity 336 of the base portion 318. The scope receiver portion 338 is adapted to receive the laparoscope 100. The scope receiver portion 338 of the illustrated embodiment of the view optimizer is a cylindrically shaped, threaded channel. However, the scope receiver portion 338 is not limited to this shape or configuration and can have any shape or configuration that allows it to receive the laparoscope 100. The scope receiver portion 338 of the illustrated embodiment is adapted to receive a grommet 340 that has a cylindrical shape with a opening defined therethrough. The grommet 340 of the illustrated embodiment is rubber, however other suitable materials may also be used, such as plastic or a composite material. The threads of the scope receiver portion 338 are adapted to mate with the threads of a nut 342 which can be tightened onto the scope receiver portion 338. The nut 342 of the illustrated embodiment has an opening defined through it. A second opening (not shown in the figures) is defined within the bottom wall of the base portion 318 of the flow controller 220. This second opening is in communication with the lens guard 210 that is connected to the base portion 318 of the main body (as shown in FIG. 6).

When the view optimizer 200 is in use, the distal end 120 of the main body 110 of a laparoscope 100 is inserted, in turn, through the opening defined within the nut 342, the opening defined within the grommet 340, and the opening defined within the scope receiver portion 338 by the scope operator. The main body 100 of the laparoscope 100 is then passed through the scope receiver portion 338 and through the base portion 318 of the flow controller 220 into the lens guard 210. Once the distal end 120 of the laparoscope 100 reaches the desired position within the lens guard 210, the nut 342 can be tightened down onto the threads of the scope receiver portion 338. This tightening of the nut 342 forces the grommet 340 to be wedged between the surface of the scope receiver portion 338 and the laparoscope 100, thereby locating the laparoscope in the desired position relative to the flow controller 220 and the lens guard 210, and preventing both linear and rotational movement of the laparoscope relative to the flow controller 220 and the lens guard 210. However, one or both of linear or rotational movement may be allowed in alternative embodiments.

As illustrated in FIG. 3E, the handle portion 320 of the flow controller 220 has a main wall 350 that defines a partially enclosed space. The configuration of the handle portion 320 is adapted to support and enclose other components of the view optimizer 200. The partially enclosed space of the handle portion 320 abuts with the interior cavity 336 of the base portion 318 so the partially enclosed space of the handle portion 320 and the interior cavity 336 of the base portion 318 are in communication when the base portion 318 and the handle portion 320 are joined. Referring to the illustrated embodiment of FIG. 3E, a burst actuator compartment 352 and a gas/liquid actuator compartment 354 are defined within the main wall 350 of the handle portion 320. The burst actuator compartment 352 is adapted to hold the burst actuator 260 and the gas/liquid actuator compartment 354 is adapted to hold the gas/liquid actuator/regulator 250. The burst actuator compartment 352 and the gas/liquid actuator compartment 354 of the handle portion 320 are in communication with each other as well as being in communication with the interior cavity 336 of the base portion 318.

The handle portion 320 of the illustrated embodiment of the view optimizer includes an end cap 330 that is removably attached to the handle portion 320 of the flow controller 220. The end cap 330 is adapted to fully enclose the gas/liquid actuator compartment 354 of the handle portion 320. Additional embodiments of the view optimizer 200 are provided without such an end cap 330. As mentioned previously, additional embodiments of the view optimizer may include a one-piece flow controller 220 as opposed to the multi-piece flow controller 220 of the illustrated embodiment. The main body can have any shape or configuration that allows it to support and/or enclose other portions of the view optimizer 200.

The gas inlet 230 and the fluid inlet 240 of the flow controller 220 extend into the gas/liquid actuator compartment 354 of the handle portion 320 of the flow controller 220. The gas inlet 230 and the liquid inlet 240 of the illustrated embodiment of the view optimizer 200 are cylindrical tubes extending outwardly from the surface of the flow controller 220. The gas inlet 230 and liquid inlet 240 are formed from plastic, but a variety of suitable materials could also be used. It should be mentioned that additional shapes and configurations could be used for the gas inlet 230 and liquid inlet 240. The gas inlet 230 and the fluid inlet 240 of the flow controller 220 receive gas and liquid respectively from external sources. The gas inlet 230 and liquid inlet 240 can have any shape or configuration that allows for the connection of the view optimizer 200 to external gas and liquid sources.

It should be understood that additional embodiments of the view optimizer 200 may include gas and/or liquid sources that are located internally within the view optimizer 200 itself, thus eliminating the need for a means of connecting the view optimizer 200 to external sources of gas and/or liquid. In addition, it should also be understood that additional embodiments of the view optimizer utilize only gas or only liquid. Whether or not the view optimizer 200 utilizes gas, liquid, or both will determine whether a gas or liquid inlet is provided with various additional embodiments of the view optimizer 200.

The gas/liquid actuator/regulator 250 of the illustrated embodiment of the view optimizer is housed within the gas/liquid actuator compartment 354 of the handle portion 320 of the flow controller 220. The gas/liquid actuator/regulator 250 of the view optimizer 200 can be formed of one of a variety of actuation means. The gas/liquid actuator/regulator 250 of the illustrated embodiment of the view optimizer 200 is a control valve, namely, a manually controlled switching valve. It should be understood, however, that additional embodiments of the view optimizer 200 may include a variety of different types of gas/liquid actuator. Additional embodiments of the view optimizer 200 may include a variety of manually or electrically controlled valves or other device. The gas/liquid actuator/regulator 250 may be any valve or similar device that actuates and/or regulates the flow of the gas and/or liquid utilized by the view optimizer 200 for delivery to the objective lens of the laparoscope 100. The gas/liquid actuator/regulator 250 of the illustrated embodiment is formed from plastic; however, other suitable materials including metals and composites may also be used.

The gas/liquid actuator/regulator 250 of the embodiment of the view optimizer 200 illustrated in FIG. 3E includes a gas inlet 358, a liquid inlet 360, a gas outlet 362 and a liquid outlet 364. Referring to FIG. 3E, the gas inlet 230 of the flow controller 220 is connected to the gas inlet 358 of the gas/liquid actuator/regulator 250 and the liquid inlet 240 is connected to the liquid inlet 360. The embodiment of the gas/liquid actuator/regulator 250 illustrated in FIG. 3E includes an actuation switch 366. The actuation switch 366 of the illustrated embodiment is a push-button that can be selectively operated to actuate the gas/liquid actuator/regulator 250. However, it should be understood that a variety of different switches or other actuation devices can be utilized to perform this function, and the view optimizer 200 of this application is not limited to a push-button type switch. The actuation switch 366 can be any type of switch or actuation device that can serve to actuate the gas/liquid actuator.

The gas/liquid actuator/regulator 250 of the illustrated embodiment of the view optimizer 200 is operable to switch between two states, a gas flow state and a liquid flow state. In the gas flow state, gas from an external gas source, such as an insufflator in the case of the illustrated embodiment, flows through the gas inlet 230 of the flow controller 220, through the gas inlet 358 of the gas/liquid actuator/regulator 250, through the gas/liquid actuator/regulator 250 and out the gas outlet 362 of the gas/liquid actuator/regulator 250. When the gas/liquid actuator/regulator 250 is in the gas flow state, liquid is prevented from flowing through the gas/liquid actuator/regulator 250 and out of the liquid outlet 364. Conversely, when the gas/liquid actuator/regulator 250 is in the liquid flow state, liquid from an external source flows through the liquid inlet 240 of the flow controller 220, through the liquid inlet 360 of the gas/liquid actuator/regulator 250, through the gas/liquid actuator/regulator 250 and out the liquid outlet 364 of the gas/liquid actuator/regulator 250. When the gas/liquid actuator/regulator 250 is in the liquid flow state, gas is prevented from flowing through the gas/liquid actuator/regulator 250 and out of the gas outlet 362.

The gas/liquid actuator/regulator 250 of the illustrated embodiment is biased towards the gas flow state and delivers a generally continuous flow of gas when in the gas flow state. In this manner, the view optimizer 200 of the illustrated embodiment delivers a generally continuous flow of gas to the objective lens of the laparoscope 100 when the gas/liquid actuator/regulator 250 is in the gas flow state. The gas/liquid actuator/regulator 250 of the illustrated embodiment remains in the gas flow state with the view optimizer delivering a generally continuous flow of gas to the objective lens of the laparoscope until an operator switches the gas/liquid actuator/regulator 250 to the liquid flow state by pressing the actuation switch 366 of the gas/liquid actuator/regulator 250. When the gas/liquid actuator/regulator 250 of the illustrated embodiment is switched to the liquid flow state, gas is not permitted to flow through the gas/liquid actuator/regulator 250. The gas/liquid actuator/regulator 250 of the illustrated embodiment only remains in the liquid flow state for as long as the operator is holding the actuation switch 366. Once the operator releases the actuation switch 366, the gas/liquid actuator of the illustrated embodiment returns to the gas flow state. Additional embodiments of the gas actuator/regulator 250 could remain in the liquid flow state until an operator presses on the actuation switch 366. In additional embodiments of the view optimizer, the actuation switch 366 may allow for the flow of both liquid and gas simultaneously. In yet additional embodiments, the gas/liquid actuator/regulator 250 may be biased towards the liquid flow state. Additionally, some view optimizers contemplated by this detailed description may only utilize gas or liquid and the actuation switch 366 of such embodiments will only activate or deactivate the flow of gas or liquid not both and not switch between the flow of gas or liquid. And in still other embodiments, the apparatuses may include more than one actuation switch, each of which independently activates and deactivates the flow of a liquid or a gas, or combinations thereof.

As shown in FIG. 6, an exhaust valve 710 is mounted within the base portion 318 of the flow controller 220. The fluid connector 313 through which the exhaust gas from within the patient's abdominal cavity passes is connected to the exhaust valve 710 by a piece of or series of tubing (not shown). The exhaust valve 710 can be a variety of different valves or similar devices. The exhaust valve 71 0 can be any device that can be used to control the flow of the exhaust gases traveling through the view optimizer 200. The exhaust valve 710 is in communication with exhaust vent 720 defined within the base portion 318 of the flow controller 220, which is adapted to allow the exhaust gas to exit the view optimizer to the surroundings. The exhaust valve 71 0 is operable to adjust the flow rate of the exhaust gas exiting the view optimizer 200 via exhaust vent 720. The controlled leak created by gas entering the lens guard 210 via the exhaust vents 516 and exiting the view optimizer via exhaust vent 720 into the surroundings helps to ensure that the pressure within the patient's abdominal cavity remains below the pre-determined pressure that the insufflator is set to maintain the patient's abdominal cavity. This ensures that the insufflator will continuously insufflate the patient's abdominal cavity and will not shut off during a surgical procedure. Due to the fact that the insufflator is prevented from shutting off, the view optimizer 200 of the illustrated embodiment will be supplied with a generally continuous supply of gas for delivery to the objective lens of the laparoscope. The flow rate of the gas exiting the patient's abdominal cavity via exhaust vents 516 can be controlled via exhaust valve 710 to allow for the scope operator to create a desired amount of leakage from the patient's abdominal cavity, while not compromising the effectiveness of the insufflation. As stated previously, however, it should be understood that additional embodiments of the view optimizer 200 may not provide a controlled leak function and, thus, may not include exhaust vents 516, an exhaust ring 306, exhaust valve 710 or exhaust vent 720. In addition, the view optimizer 200 of this detailed description is not limited to the configuration set forth above with respect to the exhaust of gases from within the patient's abdominal cavity through the view optimizer, as additional embodiments of the view optimizer may include exhaust systems that are constructed differently.

The burst actuator/regulator 260 of the illustrated embodiment of the view optimizer 200 is housed within the burst actuator compartment 352 of the handle portion 320 of the flow controller 220. The burst actuator/regulator 260 of the view optimizer 200 can be formed of one of a variety of actuation means. As shown in FIG. 3E, the burst actuator/regulator 260 of the embodiment of the view optimizer 200 illustrated in FIG. 3E is a manually operated, pneumatic bulb. However, it should be understood that the burst actuator/regulator 260 can be a variety of different manually or electrically operated devices. The burst actuator/regulator 260 can be any device that allows for the actuation and/or regulation of the burst function of the view optimizer 200. The burst actuator/regulator 260 of the illustrated embodiment is formed from rubber, however other suitable materials may be used. The burst actuator/regulator 260 of the illustrated embodiment has an inlet 370 and an outlet 372. The burst actuator/regulator 260 of the illustrated embodiment is adapted to deliver a burst or bolus of gas and/or liquid to the objective lens of the laparoscope 100 when activated by an operator. It will be understood that in various other embodiments, the apparatuses may include more than one burst actuator, each of which is adapted to work independently to deliver a burs or bolus of a liquid or a gas, or combinations thereof.

Referring again to FIG. 3E, the gas outlet 362 of the gas/liquid actuator/regulator 250 of the illustrated embodiment of the view optimizer 200 is connected to the inlet 370 of the burst actuator/regulator 260. In the embodiment of the view optimizer 200 illustrated in FIG. 3E, the gas/liquid actuator/regulator 250 is connected directly to the inlet 370 of the burst actuator/regulator 260. In other embodiments of the view optimizer 200, the gas/liquid actuator/regulator 250 and the burst actuator/regulator 260 are connected indirectly with other intermediate parts being located between them, such as tubing or conduit. In addition, it should be understood that the gas/liquid actuator/regulator 250 and the burst actuator/regulator 260 need not be connected with one another in all embodiments of the view optimizer 200, as they may each receive gas and/or liquid from separate sources. Finally, it should be understood that all embodiments of the view optimizer 200 contemplated by this detailed description do not include both a gas/liquid actuator/regulator 250 and a burst actuator, as additional embodiments may be provided with only a gas/liquid actuator/regulator 250 or burst actuator/regulator 260.

The liquid outlet 364 of the gas/liquid actuator/regulator 250 is connected to one of the fluid connectors 313 of the connection plate by tubing (not shown) that travels through the internal cavity defined within the handle portion 220 and base portion 318 of the flow controller 220. Similarly, the outlet 372 of the burst actuator/regulator 260 is connected to one of the fluid connectors 313 of the connection plate 310 by tubing (not shown) which travels through the internal cavity defined within the handle portion 220 and base portion 318 of the flow controller 220. While tubing is used in some embodiments of the sheath assembly, other suitable methods could be used, such as any type of piping or conduit or flow channels defined within portions of the flow controller 220. The view optimizer of this detailed description is not limited with respect to the method which is used to connect the gas and/or liquid source to the lens guard 210 for delivery to the objective lens of the laparoscope 100.

When the gas/liquid actuator/regulator 250 is in the gas flow state, gas flows from the gas source into the gas inlet 230 of the flow controller 220, through the gas/liquid actuator/regulator 250, through the burst actuator/regulator 260, through a piece or series of tubing into a fluid connector 313 of the connector plate 310, through opening 640 of the adapter ring 302, through a pair of channels 630 of the adapter ring 302, through a pair of corresponding channels 512 of the guard tube 304, through channels 520, 521 of the exhaust ring 306, and is directed across the lens of the laparoscope 100 by passageways 528, 530 of the end ring 308.

As the illustrated embodiment of the view optimizer 200 is adapted to deliver a generally continuous flow of gas to the objective lens of the laparoscope 100, this cycling of the insufflator needs to be prevented. For this reason, the view optimizer 200 of the illustrated embodiment is provided with exhaust vents 516 located within the exhaust ring 306. When the laparoscope 100 and the view optimizer 200 are inserted into a patient's abdominal cavity during a surgical procedure, the exhaust vents 516 of the exhaust ring 306 are located within the patient's abdominal cavity. Insufflated gas present in the patient's abdominal cavity is able to enter the exhaust vents 516 and travel through a pair of the channels 512 of the guard tube 304, thus exiting the patient's abdominal cavity. Due to the pressure differential between the interior of the lens guard 210 and the patient's abdominal cavity, this exhaust gas travels through the channels 512 of the guard tube 304, through a pair of the channels 630 of the adapter ring 302, through opening 644 of the adapter ring and through one of the fluid connectors 313 located in the connection plate 310. The fluid connector 313 which the exhaust gas travels through projects into the base portion 318 of the flow controller 220.

As shown in FIG. 6, an exhaust valve 710 is mounted within the base portion 318 of the flow controller 220. The fluid connector 313 through which the exhaust gas from within the patient's abdominal cavity passes is connected to the exhaust valve 710 by a piece of or series of tubing (not shown). The exhaust valve 710 can be a variety of different valves or similar devices. The exhaust valve 710 can be any device that can be used to control the flow of the exhaust gases traveling through the view optimizer 200. The exhaust valve 710 is in communication with exhaust vent 720 defined within the base portion 318 of the flow controller 220, which is adapted to allow the exhaust gas to exit the view optimizer to the surroundings. The exhaust valve 710 is operable to adjust the flow rate of the exhaust gas exiting the view optimizer 200 via exhaust vent 720. The controlled leak created by gas entering the lens guard 210 via the exhaust vents 516 and exiting the view optimizer via exhaust vent 720 into the surroundings helps to ensure that the pressure within the patient's abdominal cavity remains below the pre-determined pressure that the insufflator is set to maintain the patient's abdominal cavity. This ensures that the insufflator will continuously insufflate the patient's abdominal cavity and will not shut off during a surgical procedure. Due to the fact that the insufflator is prevented from shutting off, the view optimizer 200 of the illustrated embodiment will be supplied with a generally continuous supply of gas for delivery to the objective lens of the laparoscope. The flow rate of the gas exiting the patients abdominal cavity via exhaust vents 516 can be controlled via exhaust valve 710 to allow for the scope operator to create a desired amount of leakage from the patient's abdominal cavity, while not compromising the effectiveness of the insufflation. As stated previously, however, it should be understood that additional embodiments of the view optimizer 200 may not provide a controlled leak function and, thus, may not include exhaust vents 516, an exhaust ring 306, exhaust valve 710 or exhaust valve 720. In addition, the view optimizer of this detailed description is not limited to the configuration set forth above with respect to the exhaust of gases from within the patients abdominal cavity through the view optimizer, as additional embodiments of the view optimizer may include exhaust systems that are constructed differently.

View Optimizing Devices—Alternate Construction

Referring to FIG. 9, an alternate embodiment of a lens guard is depicted and corresponds to the lens guard shown in FIG. 2C, FIGS. 3A-3D, and FIGS. 10, 12, 13 and 14. Referring to FIG. 10, an alternate embodiment of a flow controller is depicted and corresponds to the flow controller shown in FIG. 2C, FIGS. 3A-3D, and FIGS. 10, 12, 13 and 14. The device components shown in these various figures provide the same functionalities, namely delivery of continuous or intermittent fluid flow at the distal end of a surgical scope, venting, and delivery of actuated liquid and gas flow. The flow controller and lens guard components according to these illustrated and pictured embodiments are connected via one or more fluid flow conduits, as illustrated in the embodiments shown in FIG. 9, with engagement between the flow controller and lens guard achieved using tubing connections to a flow manifold structure on the lens guard. The manifold is adapted to receive fluid flow from one or more of liquid and gas sources that are interconnected with the flow controller through tubing and in fluid connection with actuators on the flow controller. FIG. 10 shows the attachment positions for liquid and gas conduits. FIG. 10 further illustrates an embodiment of an actuating mechanism for control of liquid (saline) flow and a pin and spring construction that prevents line crimping when liquid flow is blocked. FIG. 10 further illustrates an embodiment of a gas burst mechanism which is formed of a bulb chamber that permits either a burst of gas or continuous gas feed to offset lag in gas flow during insufflator cycling.

Figure 11:
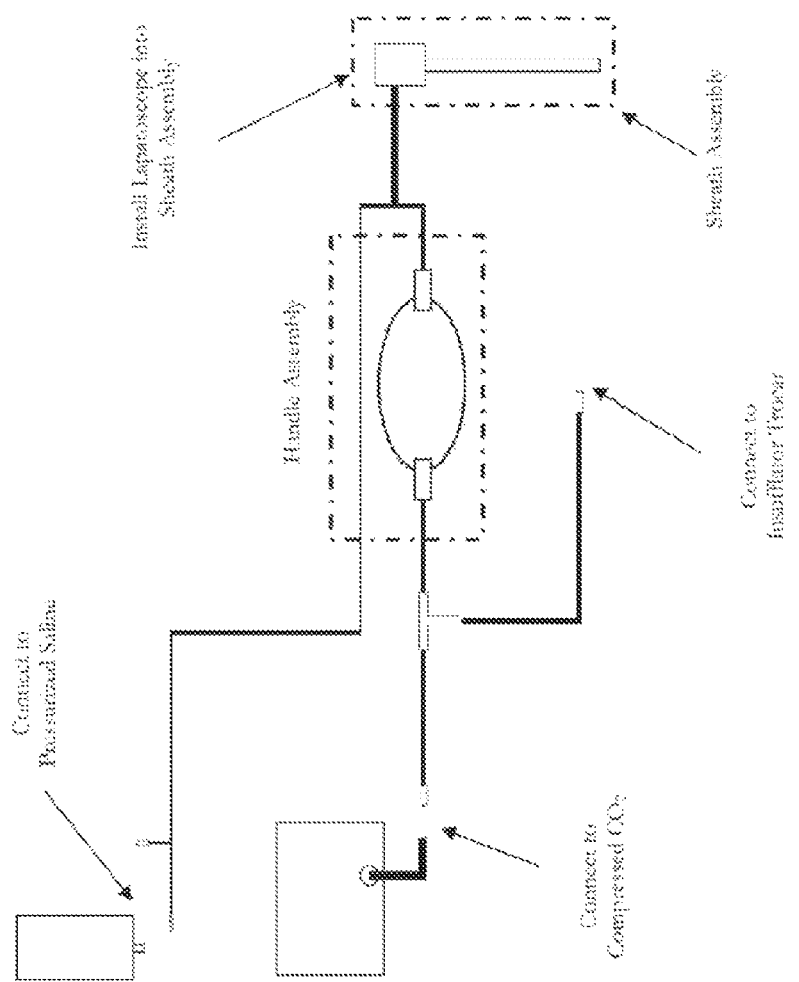
FIG. 11 shows a schematic of an embodiment of the view optimizer detailing the connectivity of the flow controller (marked handle assembly) with sources of saline and $CO_2$ and the insufflator trocar, and with the and guard tube (marked sheath assembly) which is adapted to receive the surgical scope.

Referring to FIG. 11, a schematic shows one possible configuration for interconnection of the flow optimizer components with the saline, gas, trocar and surgical scope devices in a conventional surgical suite. Of course it will be appreciated that other possible configurations may be achieved using the inventive devices and methods described herein.

Figure 12:
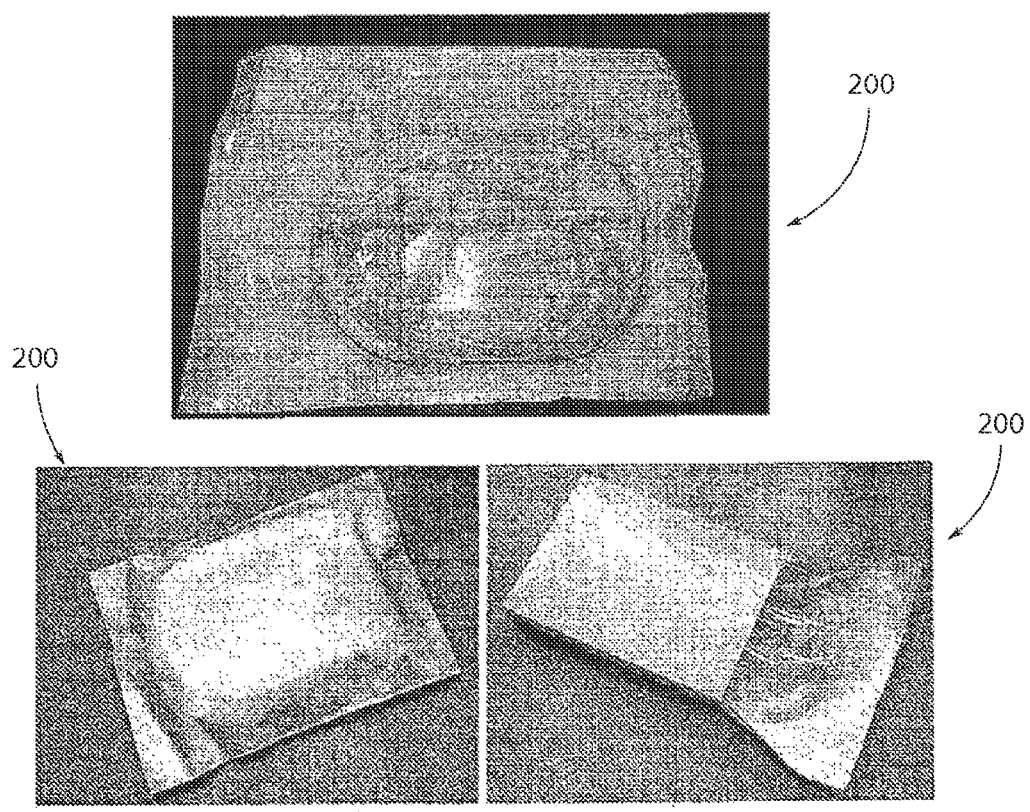
FIG. 12 shows three views of the exemplary embodiment of the view optimizer shown in FIG. 2C as packaged.
Figure 13:
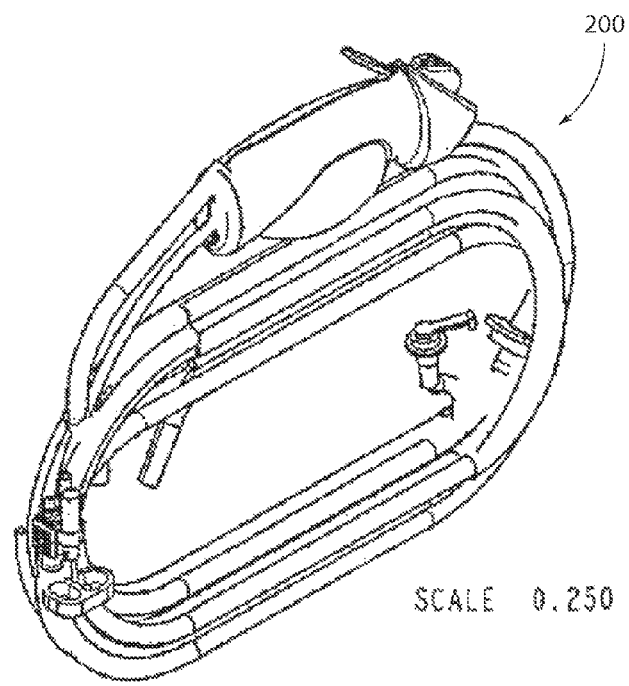
FIG. 13 shows a scaled drawing (0.250) of the exemplary embodiment of the view optimizer shown in FIG. 12, coiled for packaging.
Figure 14:
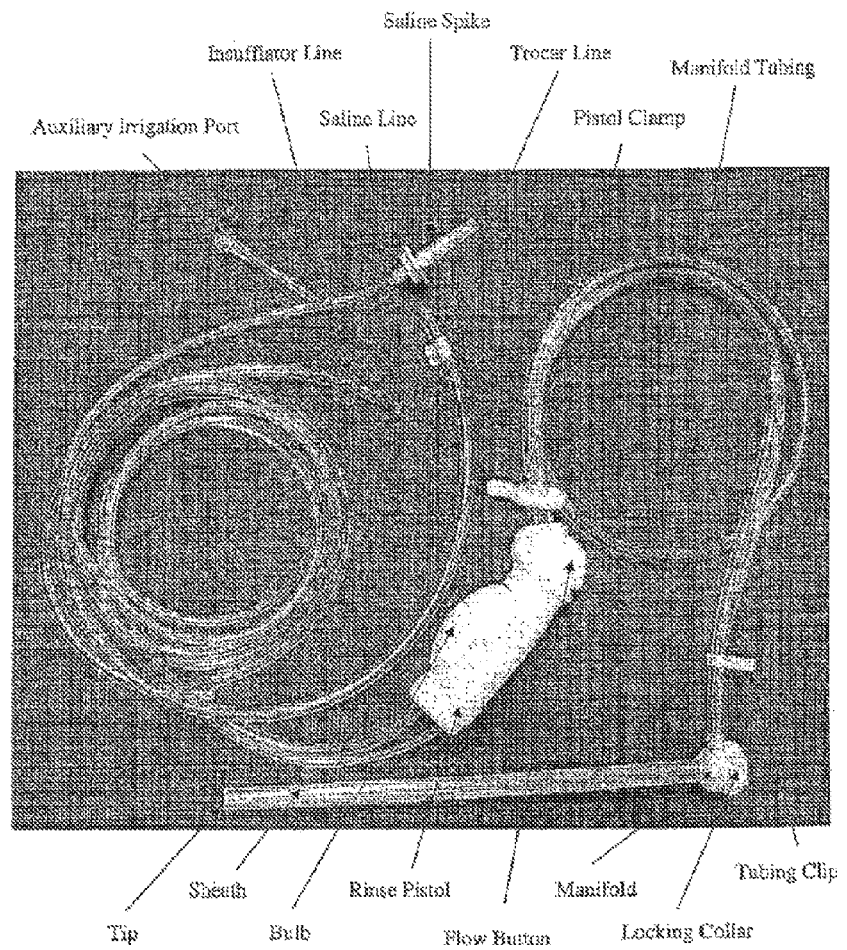
FIG. 14 is a photograph of the view optimizer embodiment of FIG. 2C and FIGS. 3A-3D with annotations identifying kit components and alternate descriptors for view optimizer components.

Referring to FIGS. 12-14, view optimizer devices corresponding with FIG. 2C and FIGS. 3A-3D are shown. FIG. 12 shows alternate photographic images of the lens guard and flow controllers connected via tubing as packaged for use. FIG. 13 shows the coiled device as it is packaged. FIG. 14 is a photograph of the device of FIG. 2 and FIGS. 3A-3D annotated to show the various connections between the view optimizer components and to conventional surgical equipment.

View Optimizer Stabilization: Scope Grip

Figure 16:
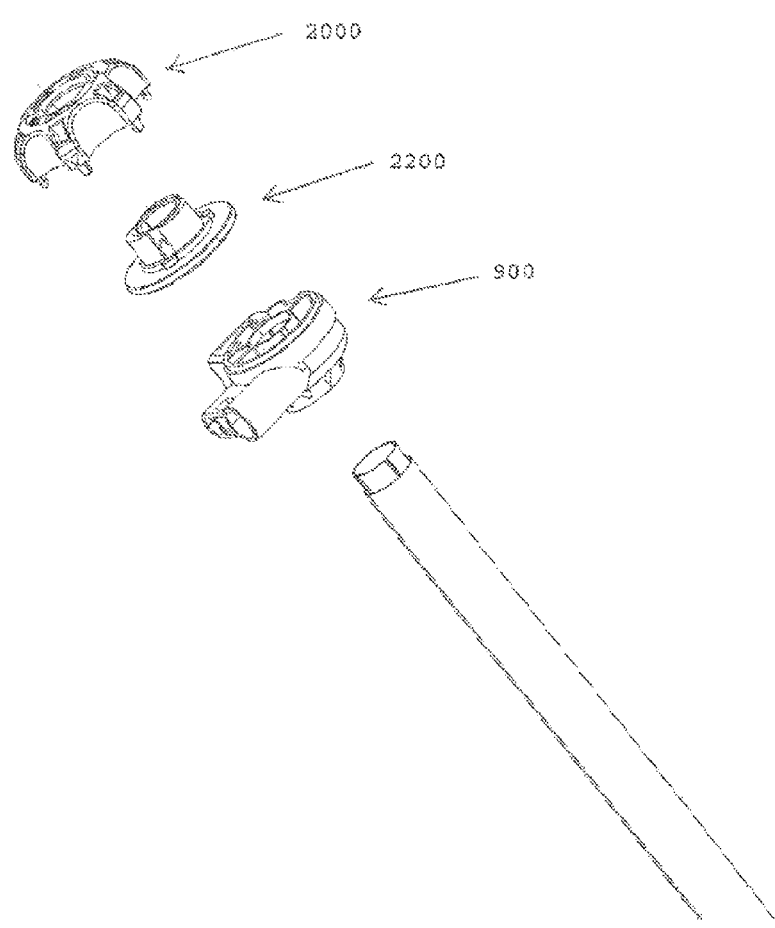
FIG. 16 shows an exploded perspective view of the components of the scope locking mechanism, which include a locking knob, cam grip, manifold and sheath.

Referring now to FIG. 16, an exploded perspective view of several components of the lens guard 210 of FIGS. 4J and 4K is shown. As depicted, the locking knob 2000, cam grip 2200, manifold cap 2400, manifold 900 and sheath are shown substantially along the axis of their orientation in the assembled lens guard 210. It will be appreciated that the locking components as depicted represent one embodiment of the components of the lens guard 210, and that the specific device components and features may vary as otherwise described in connection with the invention, and are not intended to be limited to the depicted embodiment. The locking knob 2000 is located at the proximal end 214 of the lens guard 210 and functions in part to mount the lens guard 210 to the main body of the scope.

Figure 17A:
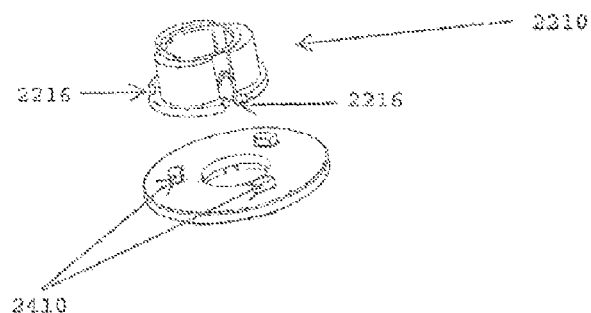
FIG. 17A shows an alternate perspective view of the components of the cam grip shown in FIG. 16.
Figure 17B:
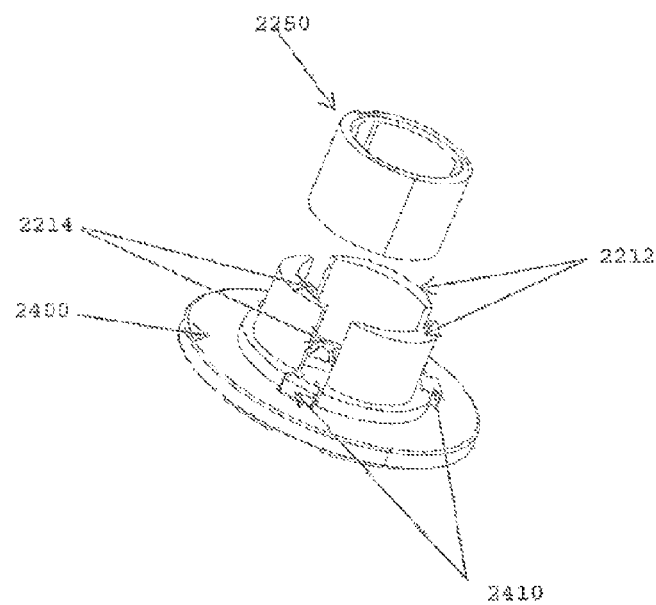
FIG. 17B shows an alternate perspective view of the components of the cam grip shown in FIG. 16.

Referring now to FIGS. 17A and 17B, the cam grip 2200 of FIG. 16 is shown in an enlarged side perspective view. FIG. 17B shows a collet 2210 associated with a manifold cap 2400 and a grommet 2250 displaced from the collet 2210; FIG. 17A shows the collet 2210 associated with the grommet 2250 and the manifold cap 2400 dissociated therefrom. While the collet 2210 serves to enhance and fix the contact between the lens guard 210 and the scope, the manifold cap 2400 serves to fix the cam grip 2200 relative to the body of the lens guard 210 so as to prevent its rotation around the axis shared by the scope and the lens guard 210. Thus, the upper surface of the manifold cap 2400 includes means for engagement with the collet 2210 so as to prevent its axial rotation. In the embodiment depicted in FIGS. 17A and 17B, the manifold cap 2400 includes a plurality tabs 2410, in this case three, that engage with slots 2216 formed between adjacent collet lobes 2212. The tabs 2410 serve to prevent axial rotation of the collet 2210 and also serve to limit the extent to which the collet 2210 is compressed when in use, as further described herein. The manifold cap 2400 includes engagement means on its lower surface (see FIG. 178A for engagement with and positional fixation relative to the manifold 900.)

Referring again to FIG. 17B, as depicted, the cam grip 2200 includes a plurality, in this case three, collet lobes 2212 that are attached to form the substantially ring-shaped collet 2210, the collet lobes 2212 are connected by three living hinges 2214. Each collet lobe 2212 is attached to an adjacent collet lobe 2212 via a living hinge 2214 attachment means. As depicted, the collet lobes 2212 have a generally crescent-shaped profile and when interconnected form an internal channel that is substantially cylindrical and an outer surface that is contoured. And as depicted, the living hinges 2214 have a generally "U" shaped profile. The collet lobes 2212 and hinges 2214 may be shaped differently. It will be appreciated that the number of collet lobes 2212 and the number of living hinges 2214 may vary, and that in some embodiments there may be as few as two collet lobes 2210 and two living hinges 2214, and in other embodiments a greater number of each may be used, and that they may vary in size, shape and spacing.

Figure 17C:
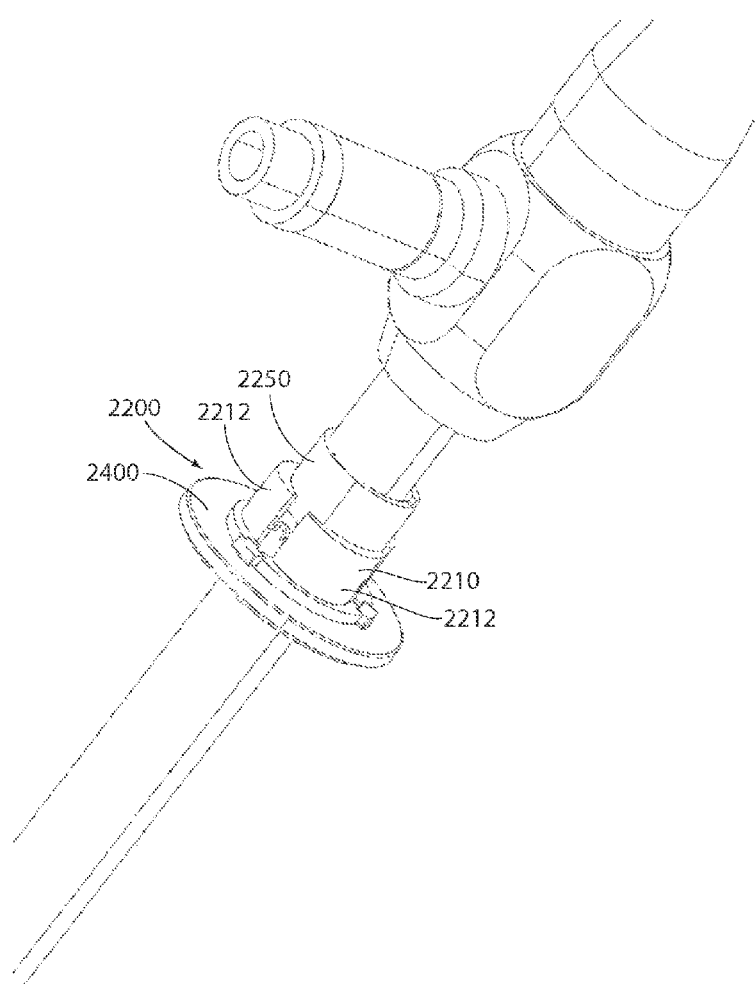
FIG. 17C shows a side perspective view of the cam grip with a laparoscope inserted therethrough.

As will be further described herein, the assembled collet 2210 is actuated by interaction with the locking knob 2000, which has a receiving means that interferes with the collet lobes 2212 when the locking knob 2000 and the cam grip 2200 are engaged so as to compress the collet lobes 2212, which in turn flexes the living hinges 2214, causing the adjacent collet lobes 2212 to move towards one another and to translate radially inward toward the center of the channel such that the circumference of the substantially circular channel through the collet 2210 is reduced. Engagement between the tabs 2410 on the manifold cap 2400 and the collet 2210 limit the extent to which the collet 2210 is compressed. Thus, actuation of the cam lobes 2212 leads to flexion of the living hinges 2214 and reduction of the diameter of the central channel, which serves to compress the grommet 2250, which thereby grips a scope body that it is inserted therethrough. FIG. 17C shows the cam grip 2200 and manifold cap 2400 in association with a surgical scope with the grommet 2250 axially displaced from the collet 2210 to illustrate the relative positioning of the collet 2210 components relative to the scope.

According to the device embodiment depicted in FIGS. 16, and 17A-17C, the collet 2210 components are of unitary construction and each component is formed of the same materials. The materials of construction may be selected from plastics or other composite materials described with respect to other components of the devices disclosed herein. Of course, in other embodiments, the collet 2210 components may be formed as a plurality of pieces that are connected using one or more appropriate means know in the art, such as by snap fit, sonic welding, glue or other adhesive, or other means Likewise, the collet 2210 components may each be formed of different materials. For example, the living hinge 2214 components may be formed of a less rigid and more flexible material as compared with the material of the collet lobes 2212. Thus, in some alternate embodiments the collet 2210 may be of unitary construction but comprise different materials for various subcomponents, and the construction may be achieved by various known methods such as in the molding and injection molding arts. And in other embodiments, the components may be discretely manufactured of the same or different materials having the same or varying properties.

Referring again to FIG. 17B, the grommet 2250 is formed as a cylinder sized to fit within the circular channel through the collet 2210. In some embodiments the grommet 2250 may be formed of the same material as one or more of the collet 2210 parts. In some embodiments the grommet 2250 is formed of a flexible rubber or other elastomeric material. As described above, the grommet 2250 functions to enhance the contact between the collet 2210 and the scope. In some embodiments, the grommet 2250 includes one or more channels that are parallel to the channel and are formed on the inner face of the grommet 2250. As depicted, the grommet 2250 has a plurality of channels, in this case three, that are arrayed at equally spaced intervals on the inner surface of the grommet 2250. The purpose of the channels is to provide a buckling or hinge point for the grommet 2250 to collapse as it is radially compressed by actuation of the collet 2210.

Figure 18A:
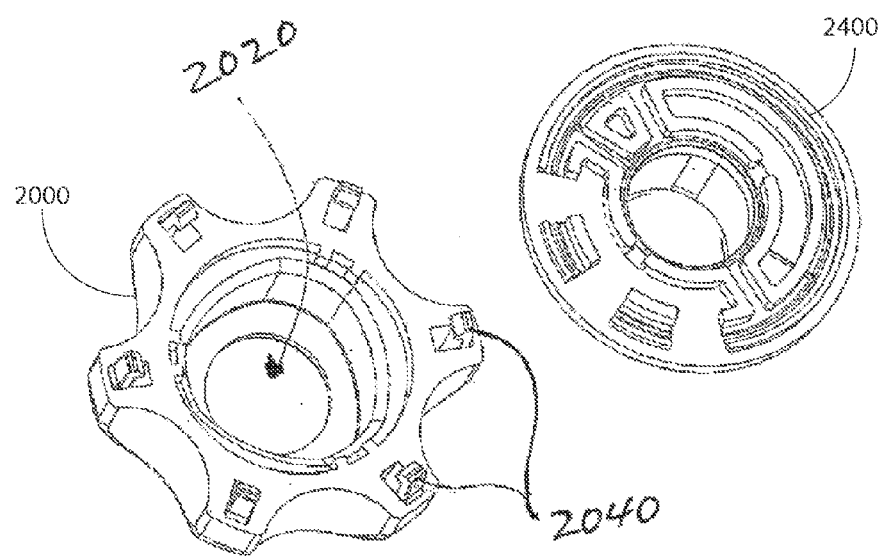
FIG. 18A shows a perspective view of the bottom of the locking knob and cam grip components.
Figure 18B:
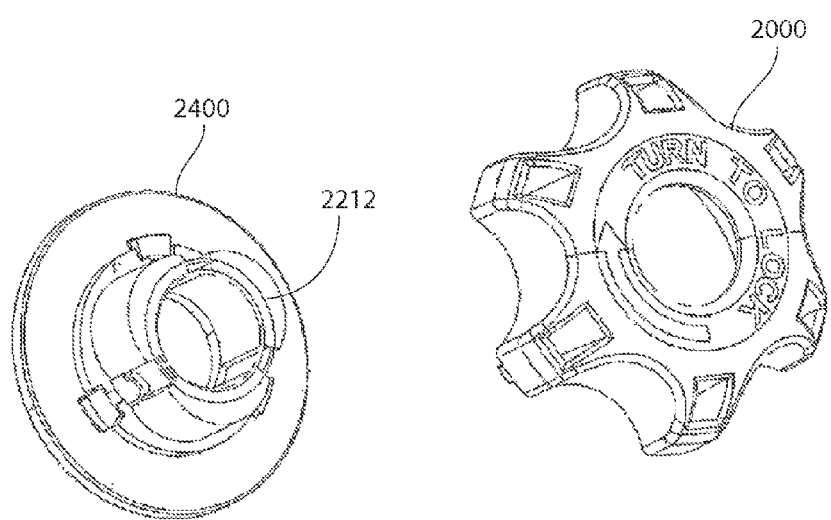
FIG. 18B shows a top perspective view of the of the locking knob and cam grip components.
Figure 18C:
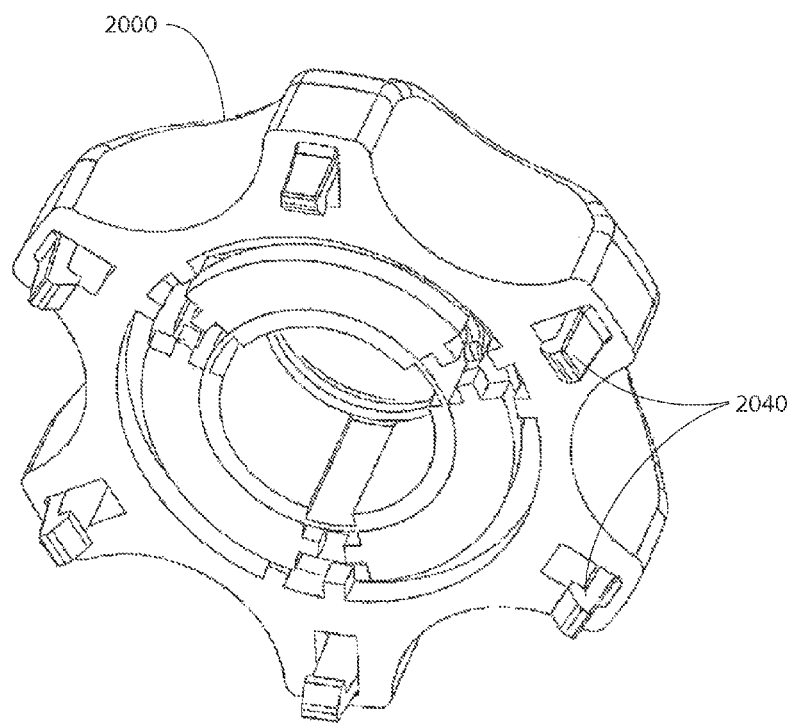
FIG. 18C shows a bottom perspective view of the locking knob and cam grip engaged.

Referring now to FIGS. 18A-18C, various views and configurations of the locking knob 2000 and the cam grip 2200 are shown. FIG. 18A shows a lower perspective view of the locking knob 2000 and the cam grip 2200 engaged with the manifold cap 2400, detailing the features of the underside of the manifold cap 2400 that are engageable with the manifold 900, and the features on the underside of the locking knob 2000. FIG. 18B shows a top perspective view of the locking knob 2000 and the cam grip 2200 engaged with the manifold cap 2400, detailing the features of the grip portion of the locking knob 2000 and the components of the cam grip 2200. As previously described, the locking knob 2000 engages with the collet 2210 to compress the cam grip 2200 and thus grip the lens guard 210 to the surgical scope. Referring to FIG. 18A, the underside of the locking knob 2000 includes a cam engagement cavity 2020 that is contoured so as to interfere with the collet lobes 2212. Thus. when the locking knob 2000 is advanced along the length of the scope body into contact with the cam grip 2200 the collet lobes 2212 are radially displaced inwardly to effectively close the collet channel against the grommet 2250 and thereby grip the scope. Referring again to FIG. 18A, the rim of the cam engagement 2020 cavity of the locking knob 2000 includes snap tabs 2040 that project radially into the cavity and are arrayed to engage with the manifold cap 2400 which is in turn coupled with the manifold 900. FIG. 18C shows the cam grip 2200 engaged with the locking knob 2000.

Figure 19A:
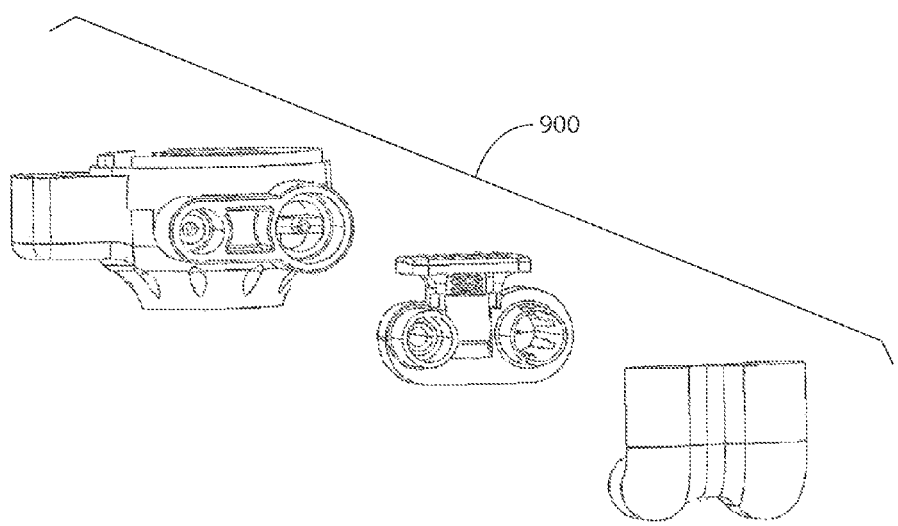
FIG. 19A shows a side perspective view of the manifold partially disassembled.
Figure 19B:
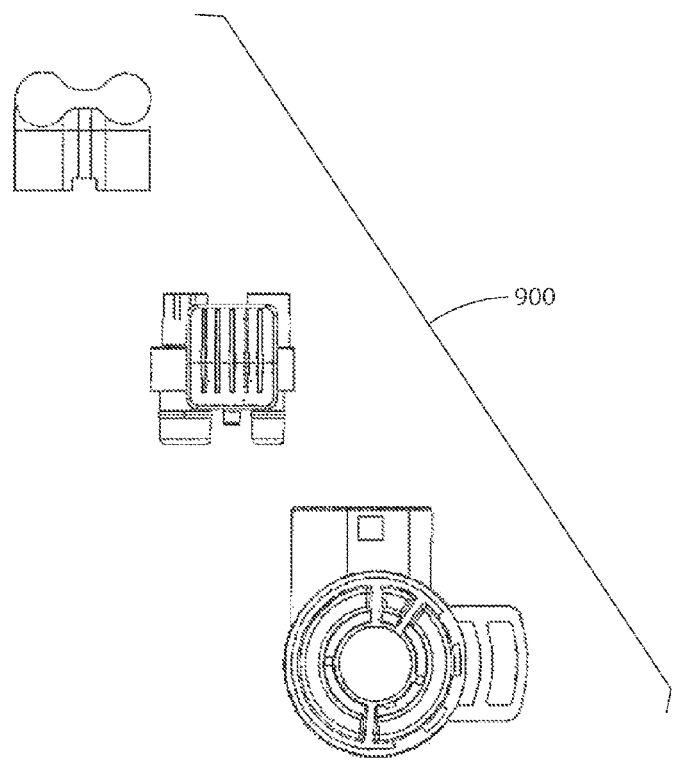
FIG. 19B shows a top plan view of the partially disassembled manifold shown in FIG. 19A.
Figure 19C:
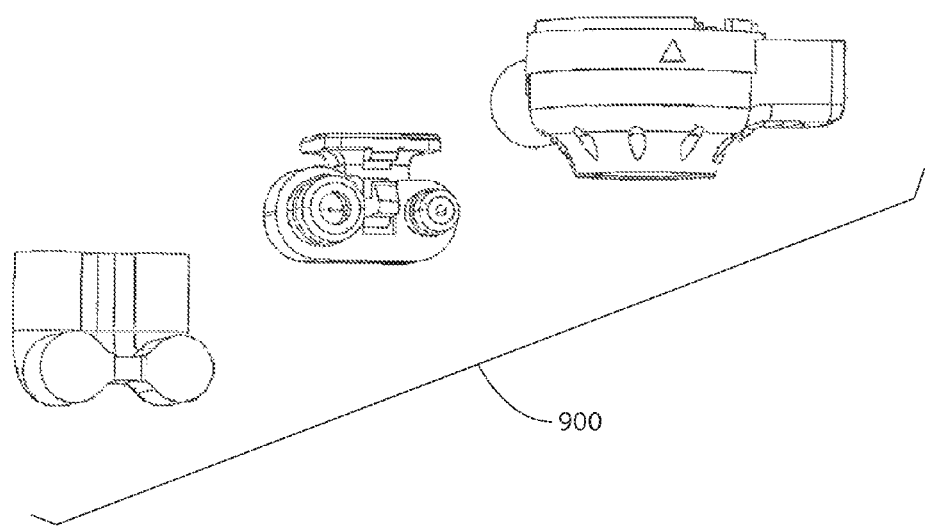
FIG. 19C shows an alternate side perspective view of the partially disassembled manifold shown in FIG. 19A.

Referring now to FIGS. 19A, 19B and 19C, these figures depict embodiments of the lens guard 210 manifold 900 that interfaces on its upper surface with the manifold cap 2400 and receives and distributes the flow of fluids from external sources through the lens guard 210 and to its tip. The device components shown in these various figures provide the same functionalities as described in connection with alternate unitary construction devices, namely delivery of continuous or intermittent fluid flow at the distal end of a surgical scope, venting, and delivery of user actuated liquid and gas flow. The flow controller 220 and lens guard 210 components according to these illustrated and pictured embodiments are connected via one or more fluid flow conduits 270, as illustrated in the drawings, with engagement between the flow controller and lens guard 210 achieved using tubing connections to the flow manifold 900 on the lens guard. The manifold 900 is adapted to receive fluid flow from one or more of liquid and gas sources that are interconnected with the flow controller 220 through tubing and in fluid connection with actuators on the flow controller 220.

Function of the View Optimizer

As mentioned previously, the gas/liquid actuator/regulator 250 of the illustrated embodiment is biased towards the gas flow state and delivers a generally continuous flow of gas from the insufflator when in this state. Accordingly, when the view optimizer 200 of the illustrated embodiment is in the normal operation state, a generally continuous flow of gas is directed across the face of the objective lens of the laparoscope 100 through passageways 528, 530 of the end ring 308. As set forth above, this gas flows in a path that is generally parallel to the objective lens of the laparoscope.

This generally continuous flow of gas across the face of the objective lens of the laparoscope 100 serves to prevent the objective lens from fogging, particularly under circumstances when there is a significant temperature and/or humidity differential between the operating room environment and the body cavity of the patient. The generally continuous flow of gas across the objective lens of the laparoscope also serves to deflect away from the objective lens any blood, bodily fluids, pieces of tissue, fat or other bodily material that may be encountered by the objective lens of the laparoscope 100 during an operative procedure. If blood, bodily fluids, pieces of tissue, fat or other bodily material is contacted by and sticks to the objective lens of the laparoscope 100, the gas flow from passageways 528, 530 serves to remove the material from the objective lens of the laparoscope 100 and to prevent the material from obstructing the view of the surgeon or medical technician through the scope.

The view optimizer 200 of the illustrated embodiment is adapted for use with conventional insufflators that typically provide gas at a flow rate of between zero (0) and fifteen (15) liters per minute when cycling during normal operation. Of course, other insufflators may deliver gas at flow rates that are considerably higher or lower, and may still be useful with the view optimizers disclosed herein. Thus, the view optimizer 200 of this detailed description can be adapted to be used with insufflators having a variety of flow rates. When in the gas flow state during normal operation, the view optimizer 200 of the illustrated embodiment is adapted to divert approximately 9% to 18% of this gas provided from the insufflator for delivery to the objective lens of the laparoscope 100 through the lens guard 210. Accordingly, the remainder of the gas provided by the insufflator continues to be delivered to the patient's body cavity through one or more of the trocars and not pass through the view optimizer 200. For example, if the insufflator produces 1 liter per minute (L/min), then 0.1 L/min (10%) would go through the view optimizer 200 to the patient and 0.9 L/min would go through the insufflator trocar to the patient Additional embodiments of the view optimizer 200 may divert more or less of the flow from the insufflator to the view optimizer 200. Accordingly, in various embodiments, the view optimizer 200 may divert about 8, 9, 10, 11, 12, 13, 14, 15, 16, 17, or 18,% of the gas provided from the insufflator. However it should be understood that additional embodiments of the view optimizer 200 may divert gas from the insufflator in excess of 19, 20, 25, 30, 40, 50, 60, 70, 80, 90% or more. And it will be appreciated that in yet other embodiments, the source of the gas may be from other than the insufflator, in which case there is no diversion of gas from direct delivery to the patient's body cavity.

When in the gas flow state during normal operation, the view optimizer 200 of the illustrated embodiment delivers a generally continuous flow of gas across the objective lens of the laparoscope 100 at a flow rate between zero (0) and ten (10) liters per minute. In some embodiments, the view optimizer 200 delivers a flow of gas at a flow rate between 0.01 and five (5) liters per minute, and in yet other embodiments the view optimizer 200 delivers a flow of gas at a flow rate between two and a half (2.5) and five (5) liters per minute. This generally continuous flow of gas across the objective lens of the laparoscope 100 forms a gas "screen," or "shield." This gas "screen" or "shield" of continuous gas flow across the objective lens of the laparoscope 100 is delivered at a velocity of between zero (0) and about forty (40) meters per second. In some embodiments, the velocity of gas is from about nineteen (19) to thirty eight (38) meters per second. Accordingly, in various embodiments, the flow rate of the gas across the lens is about 0, 0.01, 00.2, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 3, 4, 5, 6, 7, 8, 9 or 10 L/min, or increments thereof. And the velocity of the gas screen is about 1, 2, 3, 4, 5, 6, 7, 8, 9, 10, 11, 12, 13, 14, 15, 16, 17 18, 19, 20, 21, 22, 23, 24, or 25 m/s. However it should be understood that additional embodiments of the view optimizer 200 may deliver gas to the objective lens of the laparoscope at a variety of different flow rates and velocities, in which case such flow rates may exceed 10 L/min or greater and the velocities may exceed 25, 30, 40, 50, 60, 70, 80, 90 or 100 m/s or greater.

During a surgical procedure, blood, bodily fluids, pieces of tissue, fat or other bodily material may become lodged upon the objective lens of the laparoscope and effectively resist deflection or removal by the gas flow provided by the view optimizer in normal operation state. To help facilitate the removal of such adherent material, the view optimizer 200 of the illustrated embodiment provides a burst flow feature. An operator may activate the burst flow feature of the illustrated embodiment of the view optimizer 200 through the use of the burst actuator/regulator 260. As mentioned previously, the burst actuator/regulator 260 of the illustrated embodiment is a manually operated, pneumatic bulb. To activate the burst flow feature of the illustrated embodiment of the view optimizer 200, an operator squeezed the pneumatic bulb of the burst actuator/regulator 260. When the burst actuator/regulator 260 is activated, the view optimizer 200 of the illustrated embodiment delivers a burst or bolus of gas from the insufflator to the objective lens of the laparoscope 100. During the burst flow state, the view optimizer 200 of the illustrated embodiment delivers a burst or bolus of gas at a flow rate between zero (0) and twenty (20) liters per minute at a velocity of between zero (0) and one hundred and forty five (145)

meters per second. Accordingly, in various embodiments, the gas burst flow rate of the gas across the lens is about 0, 1, 2, 3, 4, 5, 6, 7, 8, 9, 10, 11, 12, 13, 14, 15, 16, 17, 18, 19, and 20 L/min, or increments thereof. And the velocity of the gas burst flow is about 1, 2, 3, 4, 5, 6, 7, 8, 9, 10, 11, 12, 13, 14, 15, 16, 17 18, 19, 20, 25, 30, 35, 40, 45, 50, 55, 60, 65, 70, 75, 80, 85, 90, 95, 100, 115, 130, or 145 m/s, or increments thereof. However it should be understood that additional embodiments of the view optimizer 200 may deliver gas burst flow to the objective lens of the laparoscope at a variety of different flow rates and velocities, in which case such flow rates may exceed 20, 25, 30, 35, 40, 45, 50 L/min or greater and such velocities may exceed 150, 155, 160, 165, 170 m/s or greater. The burst or bolus of gas serves to remove blood, bodily fluids, pieces of tissue, fat or other bodily material lodged upon the objective lens of the laparoscope that is resistant to the gas flow provided by the view optimizer in the normal operation state.

As mentioned previously, when the gas/liquid actuator/regulator 250 of the view optimizer 200 of the illustrated embodiment is in the liquid flow state, liquid is delivered to the objective lens of the laparoscope 100 and the delivery of gas ceases. When the gas/liquid actuator/regulator 250 is in the liquid flow state, liquid flows from the liquid source into the liquid inlet 240 of the flow controller 220, through the gas/liquid actuator/regulator 250, through a piece or series of tubing into a fluid connector 313 of the connector plate 310, through opening 642 of the adapter ring 302, through a channel 630 of the adapter ring 302, through a corresponding channel 512 of the guard tube 304, through channel 518 of the exhaust ring 306, and is directed across the lens of the laparoscope 100 by passageway 526 of the end ring 308. Accordingly, when the view optimizer 200 of the illustrated embodiment is in the liquid flow state, a generally continuous flow of liquid is directed across the face of the objective lens of the laparoscope 100 through passageway 526 in a path that is generally parallel to the objective lens. As shown in FIG. 4C, the passageway 526 of the end ring 308 that delivers the fluid to the objective lens is located in a position which directs the flow of the liquid in a path which is generally perpendicular to the flow of the gas provided by channels 528, 530 of the end ring 308. However, it should be understood that the view optimizer 200 of the illustrated embodiment is not limited to this configuration of the flow of liquid and gas and additional embodiments of the view optimizer 200 may provide a different configuration of gas and/or liquid flow. In addition, the gas and/or liquid flow of additional embodiments of the view optimizer may be angled towards or away from the objective lens of the laparoscope 100.

When the gas/liquid actuator is in the liquid flow state, the view optimizer 200 of the illustrated embodiment delivers liquid at a volume of generally between zero (0) and 0.4 liters per minute at a velocity of generally between zero (0) to 0.0075 meters per second. However, it should be understood that additional embodiments of the view optimizer 200 may deliver liquid at various other flow rate and velocities. Accordingly, in various embodiments, the flow rate of the liquid across the lens is about 0, 0.1, 0.2, 0.3, or 0.4 L/min. And the velocity of the liquid flow is about 0 to about 0.0075 m/s. However it should be understood that additional embodiments of the view optimizer 200 may deliver liquid to the objective lens of the laparoscope at a variety of different flow rates and velocities, in which case such flow rates may exceed 0.4, 0.5, 0.6, 0.7, 0.8, 0.9, 1.0 or greater and such velocities may exceed 0.0075 m/s or greater. This delivery of liquid to the objective lens of the laparoscope 100 serves to defog or clean the objective lens.

The burst actuator/regulator 260 of the additional embodiments of the view optimizer 200 may be adapted to serve as a gas accumulator (not shown) that accumulates pressurized gas from the insufflator, or from one or more other or additional gas sources. In the event that the insufflator cycles into the static, non insufflating state, the gas within the gas accumulator of such additional embodiments is delivered to the objective lens of the laparoscope via the view optimizer 200. This delivery of gas from the gas accumulator ensures that the view optimizer 200 is supplied with a generally steady supply of gas even when the insufflator cycles into the static state. In this manner, the gas accumulator would act as a damping mechanism to smooth out the cyclic on/off of the insufflator and ensure that a generally steady, continuous flow of gas is delivered to the objective lens of the laparoscope 100.

As an example, the burst actuator/regulator 260 of some additional embodiments may be an elastic, compliant chamber that expands to accumulate gas from the insufflator. In this manner, the burst actuator/regulator 260 could be used to actuate the delivery of a burst or bolus of gas and or liquid to the objective lens as well as serving as a gas accumulator. A backflow valve may be provided with such burst actuators 260 of additional embodiments to prevent gas from returning to the insufflator from the burst actuator/regulator 260. Such gas accumulators are adapted to accumulate gas from the insufflator until a predetermined, threshold pressure of gas within the gas accumulator is reached. Once the threshold pressure is reached, the gas accumulator would not accumulate any additional gas from the insufflator. This threshold pressure could be maintained within the accumulator either by the use of a valve or similar control mechanism or simply be maintained by the pressure of the flow of gas supplied by the insufflator.

The gas accumulator of such embodiments is adapted to maintain a pressure that is equal to or greater than the predetermined pressure at which the patient's body cavity is desired to be maintained. Once the pressure within the patient's body cavity drops below the predetermined pressure, due to the cycling off of the insufflator or some other reason, the gas accumulator would deliver gas to the objective lens of the laparoscope 100, thereby, also delivering gas to the patient's body cavity. In instances where an elastic, compliant chamber is supplied as the gas accumulator, the chamber will elastically contract in response to a pressure differential between the gas accumulator and the patient's body cavity. This contraction of the gas accumulator would serve to deliver gas to the objective lens of the laparoscope 100 and the patient's body cavity. The delivery of gas by such a gas accumulator could be controlled by the utilization of a valve or similar control mechanism. The delivery of such gas could also be delivered in a manner that is not capable of being controlled by the user.

It should be understood that the gas accumulator described above could be provided as a single chamber or multiple chambers. The gas accumulator could be incorporated with the burst actuator/regulator 260 as described above or could be provided separately from the burst actuator/regulator 260. In embodiments in which the burst actuator/regulator 260 and the accumulator function are provided separately from one another, they could each be connected to the insufflator in series or in parallel with respect to one another. Once all or a portion of the gas contained within the gas accumulator has been delivered to the objective lens of the laparoscope, the gas accumulator must be refilled with gas. If the gas accumulator is connected in series with the burst actuator/regulator 260, or other component of the view optimizer 200 that delivers gas to the objective lens, all or a portion of the flow of gas from the insufflator will first fill the gas accumulator to capacity prior to being delivered to the objective lens of the laparoscope. Due to this phenomenon, a decreased amount of flow will be delivered to the objective lens during the filling of the gas accumulator. Upon the initial startup of the insufflator or the cycling of the insufflator to an insufflation state from a static state, this can result in a time period during which little or no gas is delivered to the objective lens of the laparoscope during the filling of the gas accumulator. To prevent this from occurring, in some embodiments of the view optimizer, the gas accumulator is connected to the insufflator in parallel with relation to the burst actuator/regulator 260 or other components of the view optimizer 200 that deliver gas to the objective lens of the laparoscope to ensure that an effective flow of gas to the objective lens is maintained while the gas accumulator is being filled. In such embodiments, a portion of the gas from the insufflator can be diverted to refill the accumulator only if this diverted flow will not cause the flow of gas that is being delivered to the objective lens to drop below an effective amount. In various embodiments, the flow being diverted to the accumulator can be controlled by a valve or other similar control means.

It should be understood that the gas accumulator of additional embodiments could be adapted to accommodate a variety of different volumes of pressurized gas. In yet additional embodiments, the gas accumulator could be a non-compliant chamber that is activated by a control switch or other actuation means to deliver gas to the objective lens of the laparoscope 100 when the insufflator ceases insufflating. Such a gas accumulator could be electronically controlled and connected to the insufflator via electronic circuitry so as to be responsive to the cycling of the insufflator. Finally, it should be understood that additional embodiments of the view optimizer 200 may not be supplied with gas from an insufflator, but, rather, may include a gas supplying device incorporated within the view optimizer 200 that is comparable to the insufflator.

According to some embodiments, vibration of the objective lens of the laparoscope is utilized as an additional means for removing moisture and debris from the objective lens and/or preventing moisture and debris from adhering to the objective lens. According to some such embodiments, the view optimizer 200 is adapted to utilize the flow of gas from the insufflator to vibrate the objective lens. For example, the end ring 308 is structured in such embodiments in such a way that the flow of gas over or through the end ring 308 vibrates the end ring 308 and, thus, vibrate the objective lens as well. One such embodiment includes an end ring 308 including flexible flaps that are adapted to vibrate the end ring 308 as gas from the insufflator flows over the flaps. Additional embodiments of the view optimizer 200 include mechanical means for vibrating the objective lens that do not utilize the flow of gas from the insufflator. For example, some embodiments utilize a piezoelectric end ring 308 or one or more eccentric weights to vibrate the objective lens. It should be understood that in additional embodiments of the view optimizer 200, vibration of the objective lens may be provided in combination with one or more of the cleaning and/or defogging methods previously described or may be provided alone.

The leak of the illustrated embodiment is created by a vent or vents defined within the lens guard 210. The leak of the illustrated embodiment of the view optimizer 200 is a controlled leak that can be controlled by a user of the scope through the use of a valve or other control mechanism. The valve provided to control the leak could be a simple two-state, on/off valve or it could be a multi-state, variable valve that allows the flow rate of the leak to be adjusted. The valve or other control mechanism could be either manually operated or automated, or under electronic control. Thus, it should be understood that the leak created by the view optimizer 200 could be provided in a manner that is not controlled by a user.

The view optimizer 200 of the illustrated embodiment provides a leak that has a flow rate that is generally between zero (0) and eight (8) liters per minute, and approximately 7.8 liters per minute, wherein two of the six channels are for exhaust venting (as discussed further herein in connection with FIG. 4. Accordingly, in various embodiments, the flow rate of the leak is about 0, 0.5, 1, 1.5, 2.0, 2.5, 3.0, 3.5, 4.0, 4.5, 5.0, 5.5, 6.0, 6.5, 7.0, 7.5, 8.0 liters per minute. However it should be understood that additional embodiments of the view optimizer 200 may provide a leak having a variety of different flow rates, in which case such flow rates may exceed 8, 9, 10, 12, 14, 16, 18, or more liters per minute, or increments thereof. As a way of illustrating the effect of the leak provided by the view optimizer 200 of the illustrated embodiment on the insufflator, the following information was collected regarding the cycling intervals of a conventional insufflator during an operative procedure when a leak was provided by the view optimizer as compared to the insufflator operating without a leak being provided.

In addition, while the leak created by the view optimizer 200 of the illustrated embodiment is a passive leak that relies on the pressure within the patient's body cavity to expel gas from within the cavity, alternative embodiments of the view optimizer could be augmented by the utilization of a vacuum or other suction means to create a suction force that actively draws gas out from within the patient's body cavity. In such embodiments, the leak could likewise be under the control of the user, or otherwise under the control of an automated source or an electronic control.

Such embodiments that provide a vacuum or other suction means, may provide a suction force between zero (0) inches of mercury (in. Hg) and twenty six (26) inches of mercury (in. Hg). Accordingly, in various embodiments, the suction force provided is about 0, 1, 2, 3, 4, 5, 6, 7, 8, 9, 10, 11, 12, 13, 14, 15, 16, 17, 18, 19, 20, 21, 22, 23, 24, 25 or 26 inches of mercury (in. Hg). In some embodiments the suction force provided by the vacuum or other suction means of such embodiments is between twelve (12) inches of mercury (in. Hg) and fourteen (14) inches of mercury (in. Hg). However it should be understood that additional embodiments of the view optimizer 200 may provide a suction force having a variety of values that exceed 26 inches of mercury.

In additional embodiments of the view optimizer 200, the controlled leak could be created in alternative ways other than vents defined within the lens guard 210. For example, the leak could be created by a vent defined within the interface between the view optimizer 200 and the trocar that receives the view optimizer 200. For instance, the outer diameter of the lens guard 210 could be adapted to create a gap between the outer diameter of the lens guard 210 and the inner diameter of the trocar opening, thus, creating a leak. In addition, one or more notches, indentations or other openings could be defined within the portion of the view optimizer 200 that interfaces with the trocar, or, alternatively, within a portion of the trocar that interfaces with the view optimizer 200, to create a gap through which gas could escape. Additional embodiments may include one or more notches, indentations or openings that extend along the entire length of the lens guard 210, thereby, creating a leak between the lens guard 210 and the trocar. As discussed previously, it should be understood that this leak located at the interface between the view optimizer 200 or lens guard 210 and the trocar could be controlled with the use of a valve or other control mechanism. Thus, in one example, referring to FIG. 1B, the leak may be achieved using the stopcock valve 810 of a conventional trocar, whereby an operator opens or "cracks" the vacuum within the surgical system by actuating the valve. In addition, this leak could be a passive leak or could utilize a vacuum or other pumping means to actively draw gas out from within the patient's body cavity. It will be appreciated that the construction of the lens guard 210 may be adapted such that whether it is formed as continuous sheath, or is formed of two or more portions, it is nevertheless adapted to allow for the introduction and control of a leak according to the various embodiments described herein, whether relying on conventional venting means in the trocar system, or other structures or features of the trocar or the inventive devices herein.

While the creation of a leak helps to ensure that the insufflator provides the view optimizer 200 with a generally continuous supply of gas, the leak can also serve to remove moisture from within the patient's body cavity, thereby, decreasing the humidity within the cavity. Humidity levels in a laparoscopic surgical field can range from below 50% to close to 100% relative humidity; in most cases, the range is from about 75% to 99%, and most typically from about 85% to about 95%. Thus, the humidity within the abdomen can exist from less than 50%, to 55, 60, 65, 70, 75, 80, 85, 90, 95 and 100%, and increments thereof. Reduction of the humidity within the patient's body cavity serves to diminish the likelihood that the objective lens of the laparoscope 100 will become fogged when it is within the patient's body cavity. In addition, the leak can also help to remove smoke and mist generated from the use of a harmonic scalpel, and/or other particulate matter that is suspended in the gas within the patient's body cavity. This removal of airborne matter from within the patient's body cavity serves to ensure that the visibility through the objective lens of the laparoscope 100 is maintained.

It should be understood that the gas exiting the patient's body cavity via the leak created by the view optimizer 200 could be filtered in various embodiments. This filtering process could serve to remove blood, bodily fluids, or other matter from the gas exiting the patients body cavity, thus, preventing these potential contaminants from entering the air within the operating room. It is beneficial to remove such matter from the escaping gas to prevent anyone in the operating room from inhaling such matter. It should also be understood that the gas exiting the patient's body cavity via the leak could be recycled for re-delivery into the patient's body cavity by the insufflator or the view optimizer 200. In addition, baffles or other muffling means could be incorporated with the vents provided by additional embodiments to muffle the sound of gas exiting the vents. Finally, it will be understood that in other embodiments, wherein the supply of fluid is to be intermittent, that there is not a need for a leak.

EXAMPLES

Example 1

Effect of Venting and Incidence of Scope Removal

Evaluation of effect of venting on insufflator function was evaluated during a laparoscopic surgical procedure. The ambient surgical room temperature was 67*F, the temperature of the carbon dioxide supply was 60 F, and the room humidity was 74%. The following general observations of insufflator function were recorded: after establishing constant pressure in the abdomen sufficient to shut off insufflator operation, followed by a sudden pressure drop in the surgical cavity, there was a 2-3 sec lag before the insufflator restarted. During the standard laparoscopic procedure, the insufflator was in inflation mode ~60% of time, and cycled off for a maximum time of about 11 sec.

During a hand assisted laparoscopic procedure, the insufflator was in inflation mode ~75% of time, and cycled off for a maximum time of about 5 sec. During the standard laparoscopic procedure, with a slow continuous leak at the stop cock, with the insufflator set at a flow of 5-6 liters per minute and 12-13 mm HG, the insufflator remained in inflation mode 100% of time. During the standard laparoscopic procedure, with a slow continuous leak through a 16 G angiocath, with the insufflator set at a flow of 5 liters per minute and 12-17 mm HG, the insufflator remained in inflation mode 100% of time.

During the standard surgical procedure, without hand assist, the scope was removed from the patient several times, for the reasons and durations as follows: Fog 40 sec; Fog 40 sec; Blood 40 sec; Fog 30 sec; Cautery 25 sec; Cautery 30 sec; Fog 30 sec; and Fog 25 sec. During the standard surgical procedure, with hand assist, the scope was removed from the patient several times, for the reasons and durations as follows: Fog 30 sec; Fog 60 sec; Cautery 25 sec; Cautery 25 sec; Debris 25 sec; Fog 60 sec; Fog 45 sec; Fog 30 sec; and Fog 30 sec.

Example 2

Evaluation of Fogging

Figure 8:
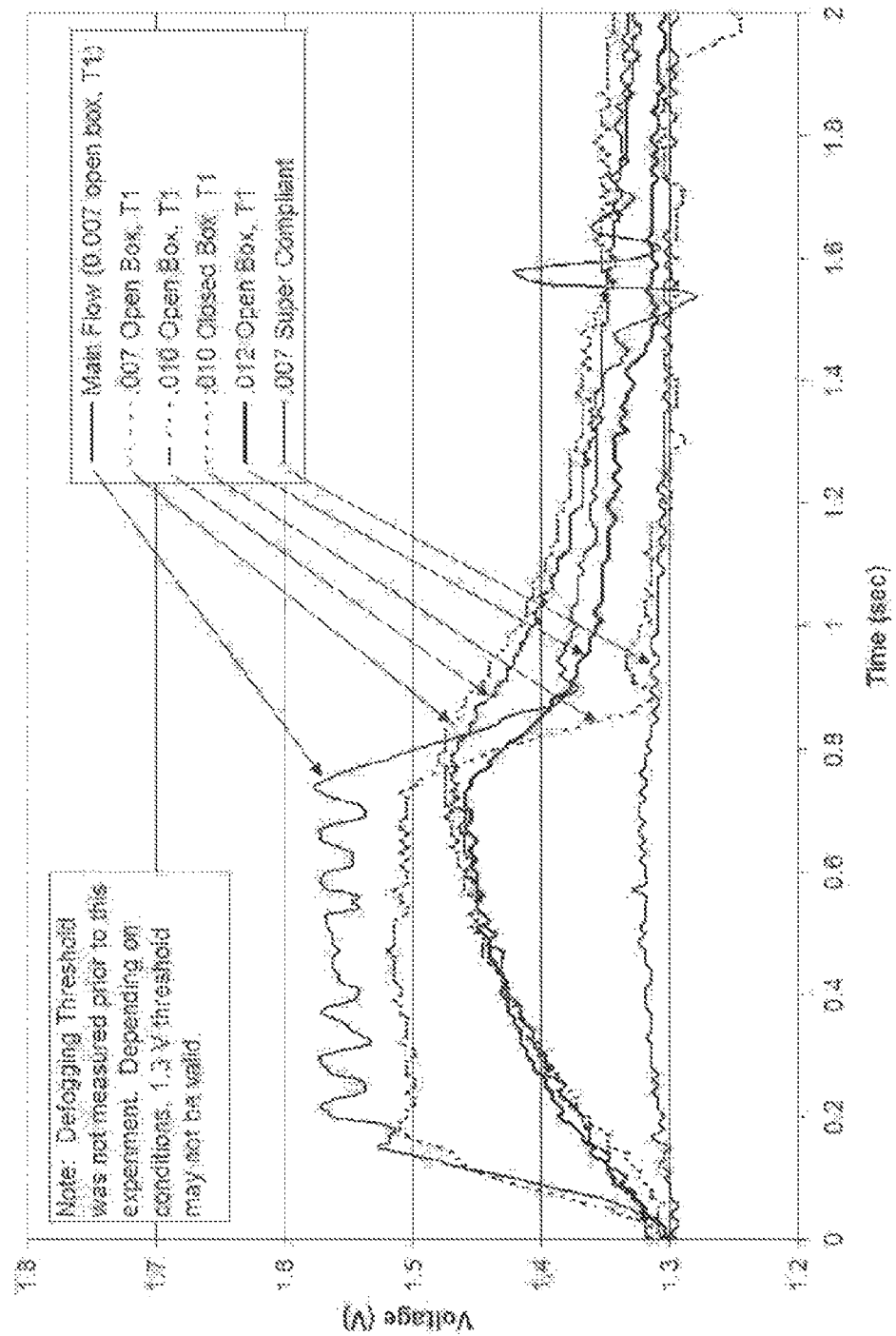
FIG. 8 shows results of evaluation of effect of introduction of compliant accumulator on flow across laparoscope lens.

In a device that simulates the humidity and temperature conditions of an animal abdominal cavity during a laparoscopic procedure, the effects of fogging on a laparoscopic lens was evaluated. Chamber temperature of 99.4-99.7° F., and an initial scope lens temperature of 70.1-72.1° F., humidity was 75-77% RH. FIG. 8 shows the change in scope temperature at the lens and various locations along its length at various times at the chambers humidity.

Relative humidity is understood as the Ratio of water vapor (dew point). Above the line corresponding to the relative humidity in the chamber, no condensation is observed; below the line, condensation is observed. The principle was observed in the study, wherein, upon initial insertion of the scope into the chamber, fogging immediately occurred and visualization of an object in the chamber was obscured. It was observed that visualization of the object improved as the scope heated up above dew point temperature, and condensation dissipated.

Example 3

Evaluation of Accumulator Reservoir Function

Testing was performed in a simulator as described in EXAMPLE 2 to compare insufflator function with and without an accumulator. The conditions of testing were similar for each trial, with chamber temperature of 99.4-99.7° F., and an initial scope lens temperature of 70.1-72.1° F., humidity was 75-77% RH.

The defogging threshold was determined in later testing. A valve was placed inline with an embodiment of the view optimizer described herein and attached to a compliant reservoir. This valve was slowly closed until the airflow was restricted to the point where de-fogging did not occur. Two trials were performed with the chamber temperature being 102.9-103.9° F. with an initial scope lens temperature of 70.5-70.9° F., humidity was 75-76% RH. Observation of the data recorder showed that at steady state, the maximum peak flow was registered at 1.3V during this time. The voltage of the sensor at 0 flow was measured pretest at 1.228V. FIG. 8 shows the resulting data, wherein the use of an accumulator reservoir compensated for the insufflator to deliver a continuous stream of air when the insufflator was shut-off, and a shift in flow was observed upon re-initiation of insufflator function until the complaint reservoir was replenished with gas.

Example 4

Use of the View Optimizer

SET UP. In use, the view optimizer is removed from packaging (example of one embodiment of packaged device is shown in FIG. 12, and as removed from the package as shown in FIG. 13).

Referring now to FIG. 14, the view optimizer is uncoiled for connection to the systems in the operating suite. The sequence of the following steps 2-6 may be modified to suit operating room practice.

Spike the view optimizer's Saline Line which is tagged & labeled (see FIG. 14) into the port of a pressurized irrigation bag. Insure that a proper connection is made and that no leaks are visible. If desired, spike the water line of a suction/irrigation system into the view optimizer's Auxiliary Irrigation Port provided via the Y-connector (see FIG. 14). If connection cannot be made, use an additional irrigation bag. Connect the view optimizer's Insufflator Line which is tagged & labeled (see FIG. 14) to the insufflator output or to the line that would formerly have been connected to the stopcock on the insufflation trocar. The Insufflator Line comes with an attached luer connector. This can be removed to accommodate a different style connection if desired. Connect the view optimizer's Trocar Line (tagged & labeled) to the stopcock on the insufflation trocar once the trocar has been properly introduced through the abdominal wall. It is recommended that the optical trocar NOT be used as the insufflation trocar. (Note: The Trocar Line remains on the sterile field after the connection is made.) Clip the view optimizer's Rinse Pistol assembly (also referred to as flow controller) to an accessible place on the sterile field of the surgical table. Use the attached Pistol Clamp (see FIG. 14) to properly secure it to the surgical drape to prevent it from inadvertently falling off the sterile field. The Rinse Pistol only needs to be accessed when a saline flush to the laparoscopic lens is needed. There is no need to constantly grasp or otherwise tend to the Rinse Pistol throughout the course of surgery.

While gently pressing the Tip of the view optimizer's Sheath assembly (also referred to as lens guard) against one hand or finger-tip, carefully insert the laparoscope down into the Sheath until the lens and distal rim of the scope is seated on the back of the view optimizer's Tip. The scope will "bottom out" inside the device. Caution: Do not use excessive force when inserting the scope into the sheath, or "slam" the laparoscope into the back of the view optimizer's Tip. The scope should slide smoothly through the shaft of the device.

While holding the laparoscope fully inserted into the Sheath, and supporting the Manifold of the Sheath by hand (see FIG. 14), rotate the Locking Collar on the Sheath assembly clockwise approximately one-third (⅓) of a turn until a firm stop is felt (see FIG. 14). This locks the scope to the view optimizer device. Note: Once locked, any rotation or up/down movement of the laparoscope inside the Sheath will not be possible without potentially stripping the locking mechanism. Be certain to unlock the scope before attempting to rotate or otherwise move it within the sheath. Before locking, check to see if any part of the Tip is present in the view of the scope (as projected on the monitor). If so, simply rotate the shaft of the scope inside the Sheath and Manifold assembly until the image of the Tip is eliminated. It may be considered useful to align the view optimizer's Manifold Tubing (air & saline line, see FIG. 14) in parallel with the cord of the laparoscope's light source before locking. Use the supplied Tubing Clip to attach the tubing to the cord and maintain this alignment. Once locked into place, examine the tip end of the view optimizer and scope assembly. To ensure proper function, the view optimizer's Tip should be securely fastened to its Sheath and no space or visible gap should be observed between the distal rim of the scope's shaft and the Tip of the device.

Operating the Device

With the insufflating trocar in place and the Trocar Line properly connected, switch on the insufflator to inflate the abdominal cavity as usual. Insert the scope and the attached the view optimizer Sheath through a 12 mm optical trocar and acquire visualization of the surgical site as usual. Caution: Do not use excessive force when inserting the Sheath and scope assembly into the trocar. The assembly should slide smoothly down the trocar. During the normal course of surgery, the view optimizer device will operate automatically to prevent fogging. Operate the laparoscope as normal. No user intervention is required.

As intra-operative visualization may be impaired due to the adherence of blood or surgical debris on the laparoscopic lens, depress the Flow Button (see FIG. 14) on the Rinse Pistol to activate a pressurized flow of saline across the lens. The saline flow will continue as long as the Flow Button is depressed, and will stop when the Flow Button is released. Typically, only a momentary flow (2-3 seconds) of saline will be sufficient to effectively rinse the lens of the laparoscope. Multiple rinses may be necessary.

To blow off any residual saline which may be present on the lens after rinsing, squeeze the Bulb (see FIG. 14) on the Rinse Pistol with a firm, sudden force creating an air burst. Several bursts may be required to remove all droplets of saline. Another flush of saline, followed by another burst from the Bulb may also prove useful in the case of a stubborn water droplet interfering with visualization. Due to the continuous laminar flow across the lens, small droplets will disappear spontaneously after a few seconds. For fatty substances, external cleaning of the lens may sometimes be required. In this case, carefully withdraw the scope/Sheath assembly from the trocar and clean the lens with a wet 4×4 gauze pad. Before re-insertion, re-examine the assembly to ensure that there is no visible gap between the end of the scope and the Tip of the device. Excessive movement of the Rinse Pistol and/or tubing lines may cause a small droplet of saline to appear on the lens without depressing the Flow Button. Should this occur, squeeze the Bulb to remove this droplet.

Removal/Disassembly

At the conclusion of surgery, withdraw the scope/the view optimizer assembly from the trocar. Unlock the assembly by rotating the Locking Collar counterclockwise approximately ⅓ of a turn. Slide the laparoscope out of the Sheath. Caution: Care should be taken not to inadvertently drop and damage the laparoscope once the assembly has been unlocked. Disconnect the tubing set from the insufflating trocar, the insufflator output circuit, and the saline reservoir. Dispose of the entire the view optimizer device and ancillary tubing set. Caution: The used view optimizer device should be treated as bio-hazardous waste and disposal should be in accordance with established institutional protocols.

Troubleshooting

If insufflation of the abdomen has been achieved and the laparoscopic view fogs and fails to clear within several seconds after insertion of the scope/the view optimizer assembly, try one or more of the following: Withdraw the scope/the view optimizer assembly from the trocar and examine the Tip. No visible gap should exist between the Tip and the lens/distal rim of the scope. If a gap does exist, unlock the assembly by rotating the Locking Collar counter-clockwise, pull the scope back several inches within the view optimizer Sheath, and reseat it by repeating steps above. Check to make sure there are no kinks or obstructions in the $CO_2$ line from the insufflator to the view optimizer device. Add additional venting to the system by slightly opening the stopcock of an adjacent trocar so as to create an air leak. Withdraw the assembly from the trocar and wipe the lens with a clean 4×4. If operation of the Rinse Pistol and depression of the Flow Button fails to produce a flow of saline across the laparoscope's lens, try one or more of the following: Check that the spike connection to the saline reservoir/bag is made properly. Check that there are no apparent leaks in the water circuit. Check that the tubing is not kinked or obstructed. Check that the saline reservoir/bag is adequately pressurized. Ensure that the laparoscope's lens is properly seated behind the Tip of the device, per the description herein above.

If insufflation of the abdomen cannot be achieved and the insufflator is operating properly, check to make sure there that the proper connection has been made between the Insufflator Line and the insufflator, that there are no kinks or obstructions in the $CO_2$ line from the insufflator to the view optimizer device, and that the proper connection has been made between the Trocar Line and the insufflating trocar.

The embodiments and examples of the view optimizer 200 described herein are representative of aspects of the invention and are provided as examples and not an exhaustive description of implementations of an aspect of the invention. While various aspects of the view optimizer 200 are described and illustrated herein as embodied in combination in the exemplary embodiments, these various aspects may be realized in many alternative embodiments, either individually or in various combinations and sub-combinations thereof. Unless expressly excluded herein all such combinations and sub-combinations are intended to be within the scope of the present application. Still further, while various alternative embodiments as to the various aspects and features of the invention, such as alternative materials, structures, configurations, methods, devices, such descriptions are not intended to be a complete or exhaustive list of available alternative embodiments, whether presently known or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated.

We claim:

1. A view optimizer for use with a surgical scope, the view optimizer comprising:
a lens guard configured to hold a surgical scope with an angled distal lens, the lens guard including:
an elongate body having a distal end, a proximal end, and a longitudinal axis extending from the proximal end to the distal end, and
a distal tip at the distal end of the elongate body, the distal tip including a distal edge that is positioned at an angle of greater than 90 degrees relative to the longitudinal axis;
a manifold attached to the lens guard and having a gas inlet configured to connect to a source of gas;
a first passageway, at least a portion of the first passageway defined within the lens guard, the first passageway having a proximal end and a distal end, the proximal end configured to be connected to the source of gas through the gas inlet of the manifold, the distal end configured to deliver gas through the distal tip to an outer surface of the angled lens of the surgical scope when the surgical scope is held by the lens guard;
a fork stabilizing feature integrated with the manifold and configured to engage with one or more components of the surgical scope to align the angled lens of the surgical scope with the angled edge of the distal tip of the lens guard and prevent rotational movement between the lens guard and the surgical scope; and
a locking mechanism coupled with the manifold, the locking mechanism including a locking knob and a collet, the collet fixed to the manifold and configured to radially compress to longitudinally fix the distal tip relative to the angled lens when activated by the locking knob.

2. The view optimizer according to claim 1 wherein the fork stabilizing feature includes one extension that engages the lens guard and two opposing extensions that are parallel to one another and are adapted to receive a portion of the surgical scope therebetween.

3. The view optimizer of claim 1, wherein the locking mechanism is a cam lock.

4. The view optimizer of claim 1, wherein the one or more components of the surgical scope comprise a light post of the surgical scope.

5. The view optimizer of claim 1, wherein a longitudinal axis of the fork stabilizing feature extends substantially parallel with the longitudinal axis of the elongate body.

6. The view optimizer of claim 1, wherein the distal edge of the distal tip is positioned at an angle of approximately 120 degrees relative to the longitudinal axis.

7. The view optimizer of claim 1, wherein the distal edge of the distal tip is positioned at an angle of approximately 135 degrees relative to the longitudinal axis.

8. The view optimizer of claim 1, wherein the fork stabilizing feature is configured to engage with the lens guard through a tab and slot attachment mechanism.

9. The view optimizer of claim 1, wherein the collet includes a plurality of collet lobes connected together by living hinges.

10. The view optimizer of claim 1, wherein the manifold further includes a fluid inlet configured to attach to a source of fluid, and wherein the view optimizer further includes a second passageway, at least a portion of the second passageway defined within the lens guard, a proximal end of the second passageway configured to be connected to the source of fluid through the fluid inlet of the manifold, and a distal end of the second passageway configured to deliver fluid through the distal tip to the outer surface of the angled lens of the surgical scope when the surgical scope is held by the lens guard.

* * * * *